(12) United States Patent
Spies et al.

(10) Patent No.: US 7,959,916 B2
(45) Date of Patent: Jun. 14, 2011

(54) NEGATIVE IMMUNOMODULATION OF IMMUNE RESPONSES BY ERP5

(75) Inventors: Thomas Spies, Seattle, WA (US); Veronika Groh-Spies, Seattle, WA (US)

(73) Assignee: Fred Hutchinson Cancer Research Center, Seattle, WA (US)

( * ) Notice: Subject to any disclaimer, the term of this patent is extended or adjusted under 35 U.S.C. 154(b) by 183 days.

(21) Appl. No.: 12/108,069

(22) Filed: Apr. 23, 2008

(65) Prior Publication Data

US 2009/0169552 A1 Jul. 2, 2009

Related U.S. Application Data

(60) Provisional application No. 60/913,467, filed on Apr. 23, 2007.

(51) Int. Cl.
*A61K 39/395* (2006.01)
(52) U.S. Cl. .................................................. 424/130.1
(58) Field of Classification Search ........................ None
See application file for complete search history.

(56) References Cited

U.S. PATENT DOCUMENTS

| | | | | |
|---|---|---|---|---|
| 6,605,278 | B1 | 8/2003 | Aggarwal | 424/145.1 |
| 2005/0233391 | A1* | 10/2005 | Spies et al. | 435/7.23 |

FOREIGN PATENT DOCUMENTS

| | | |
|---|---|---|
| WO | WO 98/19167 | 5/1998 |
| WO | WO 2007/055926 | 5/2007 |

OTHER PUBLICATIONS

Doubrovina et al., "Evasion from NK cell immunity by MHC class I chain-related molecules expressing colon adenocarcinoma," *The Journal of Immunology*, 171:6891-6899, 2003.
Bauer et al., "Activation of NK cells and T cells by NKG2D, a receptor for stress-inducible MICA," *Science*, 285(5428):727-729, 1999.
Cosman et al., "ULBPs, novel MHC class I-related molecules, bind to CMV glycoprotein UL16 and stimulate NK cytotoxicity through the NKG2D receptor," *Immunity*, 14:123-133, 2001.
Das et al., "MICA engagement by human Vgamma2Vdelta2 T cells enhances their antigen-dependent effector function," *Immunity*, 15(1):83-93, 2001.
Ellgaard and Ruddock, "The human protein disulphide isomerase family: substrate interactions and functional properties," *EMBO Rep.*, 6:28-32, 2005.
Gonzalez et al., "Immunobiology of human NKG2D and its ligands," *Curr. Topics Microbiol. Immunol.*, 298:121-138, 2006.
Groh et al., "Costimulation of CD8alphabeta T cells by NKG2D via engagement by MIC induced on virus-infected cells," *Nat. Immun.*, 2(3): 255-260, 2001.
Groh et al., "Broad tumor-associated expression and recognition by tumor-derived gamma delta T cells of MICA and MICB," *Proc. Natl. Acad. Sci. USA*, 96(12):6879-6884, 1999.
Groh et al., "Cell stress-regulated human major histocompatibility complex class I gene expressed in gastrointestinal epithelium," *Proc. Natl. Acad. Sci. USA*, 93:12445-12450, 1996.
Groh et al., "Fas-ligand-mediated paracrine T cell regulation by the receptor NKG2D in tumor immunity," *Nat. Immunol.*, 7:755-762, 2006.
Groh et al., "Stimulation of T cell autoreactivity by anomalous expression of NKG2D and its MIC ligands in rheumatoid arthritis," *Proc. Natl. Acad. Sci. USA*, 100(16):9452-9457, 2003.
Groh et al., "Tumour-derived soluble MIC ligands impair expression of NKG2D and T-cell activation," *Nature*, 419(6908):734-738, 2002.
Haridas et al., "TRANK, a novel cytokine that activates NF-kappa B and c-Jun N-terminal kinase," *The Journal of Immunology*, 161: 1-6, 1998.
Jordan and Gibbins, "Extracellular disulfide exchange and the regulation of cellular function," *Antioxid. Redox Signal*, 8:312-324, 2006.
Kikuchi et al., "Functional analysis of human P5, a protein disulfide isomerase homologue," *J. Biochem.*, 132:451-455, 2002.
Li et al., "Complex structure of the activating immunoreceptor NKG2D and its MHC class I-like ligand MICA," *Nat. Immunol.*, 2: 443-451, 2001.
Li et al., "Crystal structure of the MHC class I homolog MIC-A, a gammadelta T cell ligand," *Immunity*, 10: 577-584, 1999.
Steinle et al., "Interactions of human NKG2D with its ligands MICA, MICB, and homologs of the mouse RAE-1 protein family," *Immunogenetics*, 53(4):279-87, 2001.
Tieng et al., "Binding of *Escherichia coli* adhesin AfaE to CD55 triggers cell-surface expression of the MHC class I-related molecule MICA," *Proc. Natl. Acad. Sci. USA*, 99(5):2977-82, 2002.
Turano et al., "Proteins of the PDI family: unpredicted non-ER locations and functions," *J. Cell Physiol.*, 193:154-163, 2002.
Office Communication, issued in International Application No. PCT/US2008/061236, dated Sep. 2, 2008.
Kaiser et al., "Disulphide-isomerase-enabled shedding of tumour-associated NKG2D ligands," *Nature*, 447(7143):482, 2007.
Mou et al., "The selective inhibition of beta 1 and beta 7 integrin-mediated lymphocyte adhesion by bacitracin," *Journal of Immunology*, 161(11):6323-6329, 1998.
Zhang et al., "Imbalance of NKg2D and its inhibitory counterparts: How does tumor escape from innate immunity?," *International Immunopharmacology*, 5(7-8):1099-1111, 2005.

\* cited by examiner

*Primary Examiner* — Ilia Ouspenski
(74) *Attorney, Agent, or Firm* — Fulbright & Jaworski L.L.P.

(57) ABSTRACT

The present invention relates to methods of treating immune disorders and cancers. In particular the invention provides methods of inhibiting the negative immunomodulatory effects of ERp-5 on T cells and dendritic cells, in conjunction with other surface receptors.

4 Claims, 18 Drawing Sheets

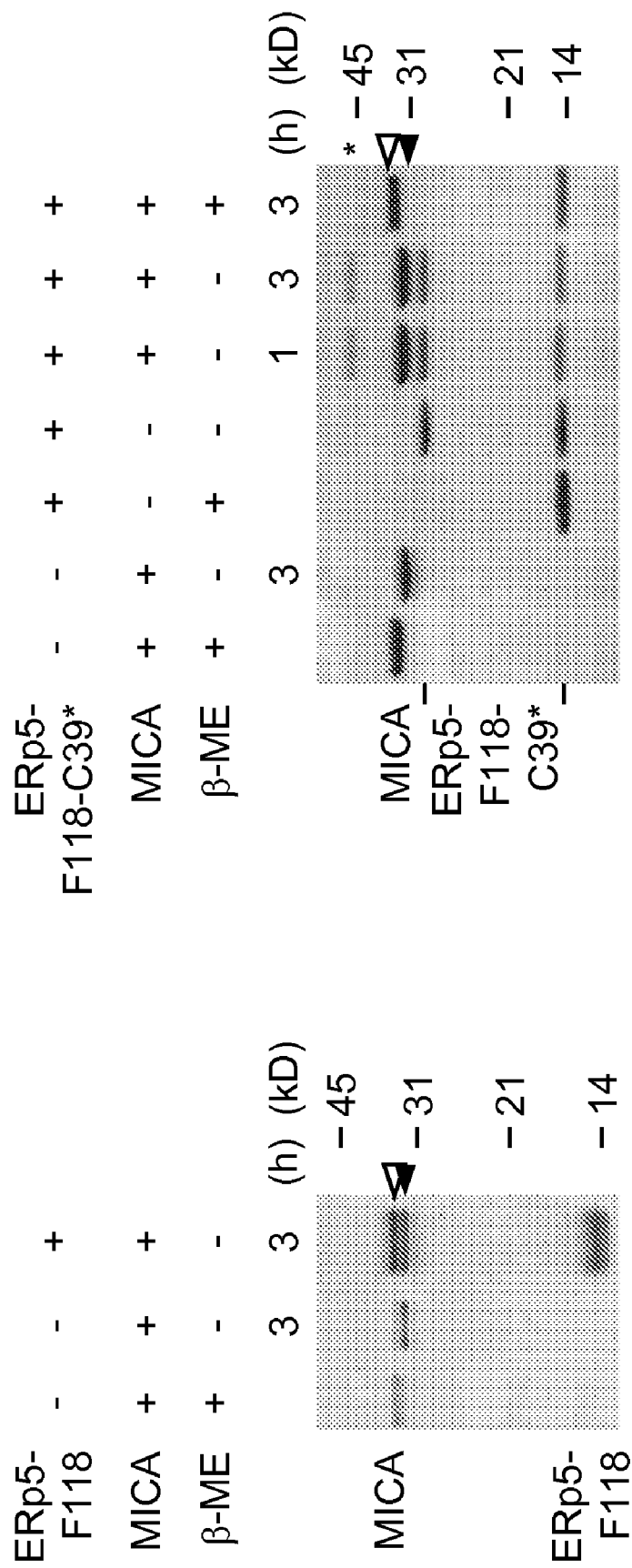

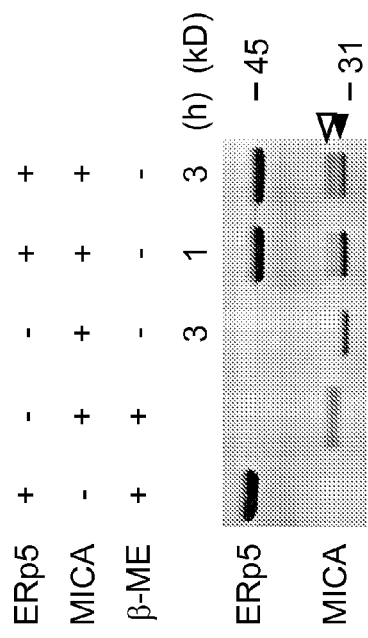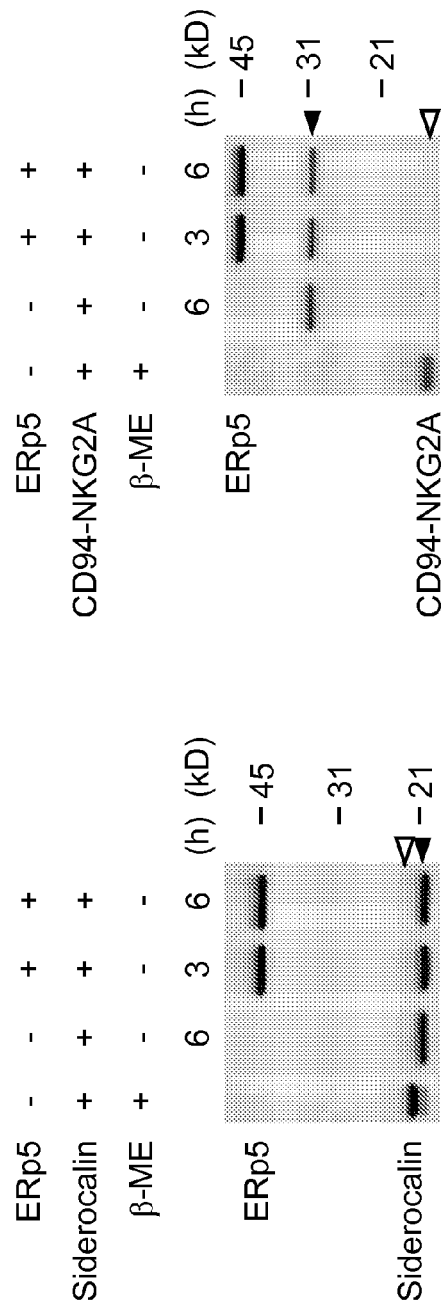

SEQUENCE LISTING

```
<160> NUMBER OF SEQ ID NOS: 20

<210> SEQ ID NO 1
<211> LENGTH: 1365
<212> TYPE: DNA
<213> ORGANISM: Homo sapiens
<220> FEATURE:
<221> NAME/KEY: CDS
<222> LOCATION: (40)..(1191)

<400> SEQUENCE: 1
cactgcttga gccgctgaga gggtggcgac gtcggggcc atg ggg ctg ggc ccg         54
                                           Met Gly Leu Gly Pro
                                             1               5 gtc ttc ctg ctt ctg gct ggc atc ttc cct ttt gca cct ccg gga gct        102
Val Phe Leu Leu Leu Ala Gly Ile Phe Pro Phe Ala Pro Pro Gly Ala
             10                  15                  20 gct gct gag ccc cac agt ctt cgt tat aac ctc acg gtg ctg tcc tgg        150
Ala Ala Glu Pro His Ser Leu Arg Tyr Asn Leu Thr Val Leu Ser Trp
         25                  30                  35 gat gga tct gtg cag tca ggg ttt ctc act gag gta cat ctg gat ggt        198
Asp Gly Ser Val Gln Ser Gly Phe Leu Thr Glu Val His Leu Asp Gly
     40                  45                  50 cag ccc ttc ctg cgc tgt gac agg cag aaa tgc agg gca aag ccc cag        246
Gln Pro Phe Leu Arg Cys Asp Arg Gln Lys Cys Arg Ala Lys Pro Gln
 55                  60                  65 gga cag tgg gca gaa gat gtc ctg gga aat aag aca tgg gac aga gag        294
Gly Gln Trp Ala Glu Asp Val Leu Gly Asn Lys Thr Trp Asp Arg Glu
 70                  75                  80                  85 acc aga gac ttg aca ggg aac gga aag gac ctc agg atg acc ctg gct        342
Thr Arg Asp Leu Thr Gly Asn Gly Lys Asp Leu Arg Met Thr Leu Ala
                 90                  95                 100 cat atc aag gac cag aaa gaa ggc ttg cat tcc ctc cag gag att agg        390
```

```
                His Ile Lys Asp Gln Lys Glu Gly Leu His Ser Leu Gln Glu Ile Arg
                                105                 110                 115 gtc tgt gag atc cat gaa gac aac agc acc agg agc tcc cag cat ttc        438
Val Cys Glu Ile His Glu Asp Asn Ser Thr Arg Ser Ser Gln His Phe
            120                 125                 130 tac tac gat ggg gag ctc ttc ctc tcc caa aac ctg gag act aag gaa        486
Tyr Tyr Asp Gly Glu Leu Phe Leu Ser Gln Asn Leu Glu Thr Lys Glu
135                 140                 145 tgg aca atg ccc cag tcc tcc aga gct cag acc ttg gcc atg aac gtc        534
Trp Thr Met Pro Gln Ser Ser Arg Ala Gln Thr Leu Ala Met Asn Val
150                 155                 160                 165 agg aat ttc ttg aag gaa gat gcc atg aag acc aag aca cac tat cac        582
Arg Asn Phe Leu Lys Glu Asp Ala Met Lys Thr Lys Thr His Tyr His
                170                 175                 180 gct atg cat gca gac tgc ctg cag gaa cta cgg cga tat cta aaa tcc        630
Ala Met His Ala Asp Cys Leu Gln Glu Leu Arg Arg Tyr Leu Lys Ser
                185                 190                 195 ggc gta gtc ctg agg aga aca gtg ccc ccc atg gtg aat gtc acc cgc        678
Gly Val Val Leu Arg Arg Thr Val Pro Pro Met Val Asn Val Thr Arg
                200                 205                 210 agc gag gcc tca gag ggc aac att acc gtg aca tgc agg gct tct ggc        726
Ser Glu Ala Ser Glu Gly Asn Ile Thr Val Thr Cys Arg Ala Ser Gly
215                 220                 225 ttc tat ccc tgg aat atc aca ctg agc tgg cgt cag gat ggg gta tct        774
Phe Tyr Pro Trp Asn Ile Thr Leu Ser Trp Arg Gln Asp Gly Val Ser
230                 235                 240                 245 ttg agc cac gac acc cag cag tgg ggg gat gtc ctg cct gat ggg aat        822
Leu Ser His Asp Thr Gln Gln Trp Gly Asp Val Leu Pro Asp Gly Asn
                250                 255                 260 gga acc tac cag acc tgg gtg gcc acc agg att tgc caa gga gag gag        870
Gly Thr Tyr Gln Thr Trp Val Ala Thr Arg Ile Cys Gln Gly Glu Glu
                265                 270                 275 cag agg ttc acc tgc tac atg gaa cac agc ggg aat cac agc act cac        918
Gln Arg Phe Thr Cys Tyr Met Glu His Ser Gly Asn His Ser Thr His
                280                 285                 290 cct gtg ccc tct ggg aaa gtg ctg gtg ctt cag agt cat tgg cag aca        966
Pro Val Pro Ser Gly Lys Val Leu Val Leu Gln Ser His Trp Gln Thr
295                 300                 305 ttc cat gtt tct gct gtt gct gct gct gct att ttt gtt att att att       1014
Phe His Val Ser Ala Val Ala Ala Ala Ala Ile Phe Val Ile Ile Ile
310                 315                 320                 325 ttc tat gtc cgt tgt tgt aag aag aaa aca tca gct gca gag ggt cca       1062
Phe Tyr Val Arg Cys Cys Lys Lys Lys Thr Ser Ala Ala Glu Gly Pro
                330                 335                 340 gag ctc gtg agc ctg cag gtc ctg gat caa cac cca gtt ggg acg agt       1110
Glu Leu Val Ser Leu Gln Val Leu Asp Gln His Pro Val Gly Thr Ser
                345                 350                 355 gac cac agg gat gcc aca cag ctc gga ttt cag cct ctg atg tca gat       1158
Asp His Arg Asp Ala Thr Gln Leu Gly Phe Gln Pro Leu Met Ser Asp
                360                 365                 370 ctt ggg tcc act ggc tcc act gag ggc gcc tag actctacagc caggcagctg    1211
Leu Gly Ser Thr Gly Ser Thr Glu Gly Ala
    375                 380 ggattcaatt ccctgcctgg atctcacgag cactttccct cttggtgcct cagtttcctg    1271
acctatgaaa cagagaaaat aaaagcactt atttattgtt gttggaggct gcaaatgtt     1331 agtagatatg aggcgtttgc agctgtacca tatt                                 1365

<210> SEQ ID NO 2
<211> LENGTH: 383
```

```
<212> TYPE: PRT
<213> ORGANISM: Homo sapiens

<400> SEQUENCE: 2

Met Gly Leu Gly Pro Val Phe Leu Leu Leu Ala Gly Ile Phe Pro Phe
1               5                   10                  15

Ala Pro Pro Gly Ala Ala Ala Glu Pro His Ser Leu Arg Tyr Asn Leu
            20                  25                  30

Thr Val Leu Ser Trp Asp Gly Ser Val Gln Ser Gly Phe Leu Thr Glu
        35                  40                  45

Val His Leu Asp Gly Gln Pro Phe Leu Arg Cys Asp Arg Gln Lys Cys
    50                  55                  60

Arg Ala Lys Pro Gln Gly Gln Trp Ala Glu Asp Val Leu Gly Asn Lys
65                  70                  75                  80

Thr Trp Asp Arg Glu Thr Arg Asp Leu Thr Gly Asn Gly Lys Asp Leu
                85                  90                  95

Arg Met Thr Leu Ala His Ile Lys Asp Gln Lys Glu Gly Leu His Ser
            100                 105                 110

Leu Gln Glu Ile Arg Val Cys Glu Ile His Glu Asp Asn Ser Thr Arg
        115                 120                 125

Ser Ser Gln His Phe Tyr Tyr Asp Gly Glu Leu Phe Leu Ser Gln Asn
    130                 135                 140

Leu Glu Thr Lys Glu Trp Thr Met Pro Gln Ser Ser Arg Ala Gln Thr
145                 150                 155                 160

Leu Ala Met Asn Val Arg Asn Phe Leu Lys Glu Asp Ala Met Lys Thr
                165                 170                 175

Lys Thr His Tyr His Ala Met His Ala Asp Cys Leu Gln Glu Leu Arg
            180                 185                 190

Arg Tyr Leu Lys Ser Gly Val Val Leu Arg Arg Thr Val Pro Pro Met
        195                 200                 205

Val Asn Val Thr Arg Ser Glu Ala Ser Glu Gly Asn Ile Thr Val Thr
    210                 215                 220

Cys Arg Ala Ser Gly Phe Tyr Pro Trp Asn Ile Thr Leu Ser Trp Arg
225                 230                 235                 240

Gln Asp Gly Val Ser Leu Ser His Asp Thr Gln Gln Trp Gly Asp Val
                245                 250                 255

Leu Pro Asp Gly Asn Gly Thr Tyr Gln Thr Trp Val Ala Thr Arg Ile
            260                 265                 270

Cys Gln Gly Glu Glu Gln Arg Phe Thr Cys Tyr Met Glu His Ser Gly
        275                 280                 285

Asn His Ser Thr His Pro Val Pro Ser Gly Lys Val Leu Val Leu Gln
    290                 295                 300

Ser His Trp Gln Thr Phe His Val Ser Ala Val Ala Ala Ala Ala Ile
305                 310                 315                 320

Phe Val Ile Ile Ile Phe Tyr Val Arg Cys Cys Lys Lys Lys Thr Ser
                325                 330                 335

Ala Ala Glu Gly Pro Glu Leu Val Ser Leu Gln Val Leu Asp Gln His
            340                 345                 350

Pro Val Gly Thr Ser Asp His Arg Asp Ala Thr Gln Leu Gly Phe Gln
        355                 360                 365

Pro Leu Met Ser Asp Leu Gly Ser Thr Gly Ser Thr Glu Gly Ala
    370                 375                 380

<210> SEQ ID NO 3
<211> LENGTH: 2385
```

```
<212> TYPE: DNA
<213> ORGANISM: Homo sapiens
<220> FEATURE:
<221> NAME/KEY: CDS
<222> LOCATION: (6)..(1157)

<400> SEQUENCE: 3 gggcc atg ggg ctg ggc cgg gtc ctg ctg ttt ctg gcc gtc gcc ttc cct      50
      Met Gly Leu Gly Arg Val Leu Leu Phe Leu Ala Val Ala Phe Pro
      1               5                   10                  15 ttt gca ccc ccg gca gcc gcc gct gag ccc cac agt ctt cgt tac aac        98
Phe Ala Pro Pro Ala Ala Ala Ala Glu Pro His Ser Leu Arg Tyr Asn
                20              25                  30 ctc atg gtg ctg tcc cag gat gga tct gtg cag tca ggg ttt ctc gct       146
Leu Met Val Leu Ser Gln Asp Gly Ser Val Gln Ser Gly Phe Leu Ala
        35                  40                  45 gag gga cat ctg gat ggt cag ccc ttc ctg cgc tat gac agg cag aaa       194
Glu Gly His Leu Asp Gly Gln Pro Phe Leu Arg Tyr Asp Arg Gln Lys
    50                  55                  60 cgc agg gca aag ccc cag gga cag tgg gca gaa gat gtc ctg gga gct       242
Arg Arg Ala Lys Pro Gln Gly Gln Trp Ala Glu Asp Val Leu Gly Ala
65                  70                  75 gag acc tgg gac aca gag acc gag gac ttg aca gag aat ggg caa gac       290
Glu Thr Trp Asp Thr Glu Thr Glu Asp Leu Thr Glu Asn Gly Gln Asp
80                  85                  90                  95 ctc agg agg acc ctg act cat atc aag gac cag aaa gga ggc ttg cat       338
Leu Arg Arg Thr Leu Thr His Ile Lys Asp Gln Lys Gly Gly Leu His
                100                 105                 110 tcc ctc cag gag att agg gtc tgt gag atc cat gaa gac agc agc acc       386
Ser Leu Gln Glu Ile Arg Val Cys Glu Ile His Glu Asp Ser Ser Thr
            115                 120                 125 agg ggc tcc cgg cat ttc tac tac aat ggg gag ctc ttc ctc tcc caa       434
Arg Gly Ser Arg His Phe Tyr Tyr Asn Gly Glu Leu Phe Leu Ser Gln
        130                 135                 140 aac ctg gag act caa gaa tcg aca gtg ccc cag tcc tcc aga gct cag       482
Asn Leu Glu Thr Gln Glu Ser Thr Val Pro Gln Ser Ser Arg Ala Gln
    145                 150                 155 acc ttg gct atg aac gtc aca aat ttc tgg aag gaa gat gcc atg aag       530
Thr Leu Ala Met Asn Val Thr Asn Phe Trp Lys Glu Asp Ala Met Lys
160                 165                 170                 175 acc aag aca cac tat cgc gct atg cag gca gac tgc ctg cag aaa cta       578
Thr Lys Thr His Tyr Arg Ala Met Gln Ala Asp Cys Leu Gln Lys Leu
                180                 185                 190 cag cga tat ctg aaa tcc ggg gtg gcc atc agg aga aca gtg ccc ccc       626
Gln Arg Tyr Leu Lys Ser Gly Val Ala Ile Arg Arg Thr Val Pro Pro
            195                 200                 205 atg gtg aat gtc acc tgc agc gag gtc tca gag ggc aac atc acc gtg       674
Met Val Asn Val Thr Cys Ser Glu Val Ser Glu Gly Asn Ile Thr Val
        210                 215                 220 aca tgc agg gct tcc agc ttc tat ccc cgg aat atc aca ctg acc tgg       722
Thr Cys Arg Ala Ser Ser Phe Tyr Pro Arg Asn Ile Thr Leu Thr Trp
    225                 230                 235 cgt cag gat ggg gta tct ttg agc cac aac acc cag cag tgg ggg gat       770
Arg Gln Asp Gly Val Ser Leu Ser His Asn Thr Gln Gln Trp Gly Asp
240                 245                 250                 255 gtc ctg cct gat ggg aat gga acc tac cag acc tgg gtg gcc acc agg       818
Val Leu Pro Asp Gly Asn Gly Thr Tyr Gln Thr Trp Val Ala Thr Arg
                260                 265                 270 att cgc caa gga gag gag cag agg ttc acc tgc tac atg gaa cac agc       866
Ile Arg Gln Gly Glu Glu Gln Arg Phe Thr Cys Tyr Met Glu His Ser
            275                 280                 285
```

| | | | | | | | | | | | | | | | |
|---|---|---|---|---|---|---|---|---|---|---|---|---|---|---|---|
| ggg | aat | cac | ggc | act | cac | cct | gtg | ccc | tct | ggg | aag | gcg | ctg | gtg | ctt | 914
| Gly | Asn | His | Gly | Thr | His | Pro | Val | Pro | Ser | Gly | Lys | Ala | Leu | Val | Leu |
| | 290 | | | | 295 | | | | 300 | | | | | | |

| cag | agt | caa | cgg | aca | gac | ttt | cca | tat | gtt | tct | gct | gct | atg | cca | tgt | 962
| Gln | Ser | Gln | Arg | Thr | Asp | Phe | Pro | Tyr | Val | Ser | Ala | Ala | Met | Pro | Cys |
| 305 | | | | | 310 | | | | | 315 | | | | | |

| ttt | gtt | att | att | att | att | ctc | tgt | gtc | cct | tgt | tgc | aag | aag | aaa | aca | 1010
| Phe | Val | Ile | Ile | Ile | Ile | Leu | Cys | Val | Pro | Cys | Cys | Lys | Lys | Lys | Thr |
| 320 | | | | | 325 | | | | | 330 | | | | | 335 |

| tca | gcg | gca | gag | ggt | cca | gag | ctt | gtg | agc | ctg | cag | gtc | ctg | gat | caa | 1058
| Ser | Ala | Ala | Glu | Gly | Pro | Glu | Leu | Val | Ser | Leu | Gln | Val | Leu | Asp | Gln |
| | | | | 340 | | | | | 345 | | | | | 350 | |

| cac | cca | gtt | ggg | aca | gga | gac | cac | agg | gat | gca | gca | cag | ctg | gga | ttt | 1106
| His | Pro | Val | Gly | Thr | Gly | Asp | His | Arg | Asp | Ala | Ala | Gln | Leu | Gly | Phe |
| | | | 355 | | | | | 360 | | | | | 365 | | |

| cag | cct | ctg | atg | tca | gct | act | ggg | tcc | act | ggt | tcc | act | gag | ggc | gcc | 1154
| Gln | Pro | Leu | Met | Ser | Ala | Thr | Gly | Ser | Thr | Gly | Ser | Thr | Glu | Gly | Ala |
| | | | 370 | | | | | 375 | | | | | 380 | | | tag actctacagc caggcggcca ggattcaact ccctgcctgg atctcaccag    1207
cactttccct ctgtttcctg acctatgaaa cagaaaataa catcacttat ttattgttgt    1267
tggatgctgc aaagtgttag taggtatgag gtgtttgctg ctctgccacg tagagagcca    1327
gcaaagggat catgaccaac tcaacattcc attggaggct atatgatcaa acagcaaatt    1387
gtttatcatg aatgcaggat gtgggcaaac tcacgactgc tcctgccaac agaaggtttg    1447
ctgagggcat tcactccatg gtgctcattg gagtttatcta ctgggtcatc tagagcctat    1507
tgtttgagga atgcagtctt acaagcctac tctggaccca gcagctgact ccttcttcca    1567
cccctcttct tgctatctcc tataccaata aatacgaagg gctgtggaag atcagagccc    1627
ttgttcacga gaagcaagaa gcccctgac cccttgttcc aaatatactc ttttgtcttt    1687
ctctttattc ccacgttcgc cctttgttca gtccaataca gggttgtggg gcccttaaca    1747
gtgccatatt aattggtatc attatttctg ttgttttttgt ttttgttttt gttttgttt    1807
ttgagacaga gtctcactct gtcacccagg ctgcagttca ctggtgtgat ctcagctcac    1867
tgcaacctct gcctcccagg ttcaagcact tctcgtacct cagactcccg aatagctggg    1927
attacagaca ggcaccacca cacccagcta attttgtat ttttttgtaga acgggggttt    1987
cgccaagttg accagcccag tttcaaactc ctgacctcag gtgatctgcc tgccttggca    2047
tcccaaagtg ctgggattac aagaatgagc caccgtgcct ggcctatttt attatattgt    2107
aatatatttt attatattag ccaccatgcc tgtcctattt tcttatgttt taatatattt    2167
taatatatta catgtgcagt aattagatta tcatgggtga actttatgag tgagtatctt    2227
ggtgatgact cctcctgacc agcccaggac cagctttctt gtcaccttga ggtcccctcg    2287
ccccgtcaca ccgttatgca ttactctgtg tctactatta tgtgtgcata atttataccg    2347
taaatgttta ctctttaaat agaaaaaaaa aaaaaaaa    2385

<210> SEQ ID NO 4
<211> LENGTH: 383
<212> TYPE: PRT
<213> ORGANISM: Homo sapiens

<400> SEQUENCE: 4

Met Gly Leu Gly Arg Val Leu Leu Phe Leu Ala Val Ala Phe Pro Phe
1               5                   10                  15

Ala Pro Pro Ala Ala Ala Ala Glu Pro His Ser Leu Arg Tyr Asn Leu
            20                  25                  30

-continued

Met Val Leu Ser Gln Asp Gly Ser Val Gln Ser Gly Phe Leu Ala Glu
            35                  40                  45

Gly His Leu Asp Gly Gln Pro Phe Leu Arg Tyr Asp Arg Gln Lys Arg
 50                  55                  60

Arg Ala Lys Pro Gln Gly Gln Trp Ala Glu Asp Val Leu Gly Ala Glu
 65                  70                  75                  80

Thr Trp Asp Thr Glu Thr Glu Asp Leu Thr Glu Asn Gly Gln Asp Leu
                 85                  90                  95

Arg Arg Thr Leu Thr His Ile Lys Asp Gln Lys Gly Gly Leu His Ser
            100                 105                 110

Leu Gln Glu Ile Arg Val Cys Glu Ile His Glu Asp Ser Ser Thr Arg
            115                 120                 125

Gly Ser Arg His Phe Tyr Tyr Asn Gly Glu Leu Phe Leu Ser Gln Asn
130                 135                 140

Leu Glu Thr Gln Glu Ser Thr Val Pro Gln Ser Ser Arg Ala Gln Thr
145                 150                 155                 160

Leu Ala Met Asn Val Thr Asn Phe Trp Lys Glu Asp Ala Met Lys Thr
                165                 170                 175

Lys Thr His Tyr Arg Ala Met Gln Ala Asp Cys Leu Gln Lys Leu Gln
            180                 185                 190

Arg Tyr Leu Lys Ser Gly Val Ala Ile Arg Arg Thr Val Pro Pro Met
            195                 200                 205

Val Asn Val Thr Cys Ser Glu Val Ser Glu Gly Asn Ile Thr Val Thr
            210                 215                 220

Cys Arg Ala Ser Ser Phe Tyr Pro Arg Asn Ile Thr Leu Thr Trp Arg
225                 230                 235                 240

Gln Asp Gly Val Ser Leu Ser His Asn Thr Gln Gln Trp Gly Asp Val
                245                 250                 255

Leu Pro Asp Gly Asn Gly Thr Tyr Gln Thr Trp Val Ala Thr Arg Ile
            260                 265                 270

Arg Gln Gly Glu Glu Gln Arg Phe Thr Cys Tyr Met Glu His Ser Gly
            275                 280                 285

Asn His Gly Thr His Pro Val Pro Ser Gly Lys Ala Leu Val Leu Gln
290                 295                 300

Ser Gln Arg Thr Asp Phe Pro Tyr Val Ser Ala Ala Met Pro Cys Phe
305                 310                 315                 320

Val Ile Ile Ile Ile Leu Cys Val Pro Cys Cys Lys Lys Lys Thr Ser
                325                 330                 335

Ala Ala Glu Gly Pro Glu Leu Val Ser Leu Gln Val Leu Asp Gln His
            340                 345                 350

Pro Val Gly Thr Gly Asp His Arg Asp Ala Ala Gln Leu Gly Phe Gln
            355                 360                 365

Pro Leu Met Ser Ala Thr Gly Ser Thr Gly Ser Thr Glu Gly Ala
370                 375                 380

<210> SEQ ID NO 5
<211> LENGTH: 66
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 5
gatcttgttg tcaaagttgg tgcagttgtc ttcttctcaa ctgcaccaac tttgacaaca      60
tttttg                                                                66

<210> SEQ ID NO 6
<211> LENGTH: 66
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 6
aattcaaaaa tgttgtcaaa gttggtgcag ttgagaagaa gacaactgca ccaactttga    60
caacaa                                                              66

<210> SEQ ID NO 7
<211> LENGTH: 66
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 7
gatcttgata gttcaagtaa gaaggatgtc ttcttctcat ccttcttact tgaactatca    60
tttttg                                                              66

<210> SEQ ID NO 8
<211> LENGTH: 66
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 8
aattcaaaaa tgatagttca agtaagaagg atgagaagaa gacatccttc ttacttgaac    60
tatcaa                                                              66

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 9
tgcggcacgc tgcagggct                                                19

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 10
ttgacagtga ccacaccatg gagcata                                       27

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence:
      Synthetic Primer

```
<400> SEQUENCE: 11
ggaacggaaa ggacctcagg atg                                            23

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 12
ctgggagctc ctggtgctgt tg                                             22

<210> SEQ ID NO 13
<211> LENGTH: 1790
<212> TYPE: DNA
<213> ORGANISM: Homo sapiens

<400> SEQUENCE: 13
ggcgcggggg cgcggcgtgc ggcacgctgc agggctgaag cggcggcggc ggtggggact    60
gcacgtagcc cggcgctcgg catggctctc ctggtgctcg gtctggtgag ctgtaccttc   120
tttctggcag tgaatggtct gtattcctct agtgatgatg tgatcgaatt aactccatcg   180
aatttcaacc gagaagttat tcagagtgat agtttgtggc ttgtagaatt ctatgctcca   240
tggtgtggtc actgtcaaag attaacacca gaatggaaga agcagcaac tgcattaaaa   300 gatgttgtca agttggtgc agttgatgca gataagcatc attccctagg aggtcagtat   360
ggtgttcagg gatttcctac cattaagatt tttggatcca acaaaaacag accagaagat   420
taccaaggtg gcagaactgg tgaagccatt gtagatgctg cgctgagtgc tctgcgccag   480
ctcgtgaagg atcgcctcgg gggacggagc ggaggataca gttctggaaa acaaggcaga   540
agtgatagtt caagtaagaa ggatgtgatt gagctgacag acgacagctt tgataagaat   600
gttctggaca gtgaagatgt ttggatggtt gagttctatg ctccttggtg tggacactgc   660
aaaaacctag agccagagtg ggctgccgca gcttcagaag taaaagagca gacgaaagga   720
aaagtgaaac tggcagctgt ggatgctaca gtcaatcagg ttctggcctc ccgatacggg   780
attagaggat ttcctacaat caagatattt cagaaaggcg agtctcctgt ggattatgac   840
ggtgggcgga caagatccga catcgtgtcc cgggcccttg atttgttttc tgataacgcc   900
ccacctcctg agctgcttga gattatcaac gaggacattg ccaagaggac gtgtgaggag   960
caccagctct gtgttgtggc tgtgctgccc catatccttg atactggagc tgcaggcaga  1020
aattcttatc tggaagttct tctgaagttg cagacaaat acaaaaagaa aatgtggggg   1080
tggctgtgga cagaagctgg agcccagtct gaacttgaga ccgcgttggg gattggaggg  1140
tttgggtacc cgccatggc cgccatcaat gcacgcaaga tgaaatttgc tctgctaaaa  1200
ggctccttca gtgagcaagg catcaacgag tttctcaggg agctctcttt tgggcgtggc  1260
tccacggcac ctgtaggagg cggggctttc cctaccatcg ttgagagaga gccttgggac  1320
ggcagggatg gcgagcttcc cgtggaggat gacattgacc tcagtgatgt ggagcttgat  1380
gacttaggga agatgagtt gtgagagcca acagagggc ttcagaccat tttcttttct   1440
tgggagccag tggattttc cagcagtgaa gggacattct ctacactcag atgactctac  1500
cagtggcctt ttaaccaaga agtagtactt gattggtcat tgaaaacac tgcaacagtg   1560 aactttgca tctcaagaaa acattgaaaa attctatgaa ttgttgtagc cggtgaattg  1620
```

```
agtcgtattc tgtcacataa tattttgaag aaaacttggc tgtcgaaaca ttttctctc     1680 tgactgctgc ttgaatgttc ttggaggctg tttcttatgt atgggttttt tttaatgtga    1740
tcccttcatt tgaatattaa tggcttttc cattaaagaa taaaatattt               1790
```

<210> SEQ ID NO 14
<211> LENGTH: 440
<212> TYPE: PRT
<213> ORGANISM: Homo sapiens

<400> SEQUENCE: 14

```
Met Ala Leu Leu Val Leu Gly Leu Val Ser Cys Thr Phe Phe Leu Ala
 1               5                  10                  15

Val Asn Gly Leu Tyr Ser Ser Asp Asp Val Ile Glu Leu Thr Pro
                20                  25                  30

Ser Asn Phe Asn Arg Glu Val Ile Gln Ser Asp Ser Leu Trp Leu Val
            35                  40                  45

Glu Phe Tyr Ala Pro Trp Cys Gly His Cys Gln Arg Leu Thr Pro Glu
        50                  55                  60

Trp Lys Lys Ala Ala Thr Ala Leu Lys Asp Val Val Lys Val Gly Ala
 65                  70                  75                  80

Val Asp Ala Asp Lys His His Ser Leu Gly Gly Gln Tyr Gly Val Gln
                85                  90                  95

Gly Phe Pro Thr Ile Lys Ile Phe Gly Ser Asn Lys Asn Arg Pro Glu
            100                 105                 110

Asp Tyr Gln Gly Gly Arg Thr Gly Glu Ala Ile Val Asp Ala Ala Leu
        115                 120                 125

Ser Ala Leu Arg Gln Leu Val Lys Asp Arg Leu Gly Gly Arg Ser Gly
    130                 135                 140

Gly Tyr Ser Ser Gly Lys Gln Gly Arg Ser Asp Ser Ser Ser Lys Lys
145                 150                 155                 160

Asp Val Ile Glu Leu Thr Asp Asp Ser Phe Asp Lys Asn Val Leu Asp
                165                 170                 175

Ser Glu Asp Val Trp Met Val Glu Phe Tyr Ala Pro Trp Cys Gly His
            180                 185                 190

Cys Lys Asn Leu Glu Pro Glu Trp Ala Ala Ala Ser Glu Val Lys
        195                 200                 205

Glu Gln Thr Lys Gly Lys Val Lys Leu Ala Ala Val Asp Ala Thr Val
    210                 215                 220

Asn Gln Val Leu Ala Ser Arg Tyr Gly Ile Arg Gly Phe Pro Thr Ile
225                 230                 235                 240

Lys Ile Phe Gln Lys Gly Glu Ser Pro Val Asp Tyr Asp Gly Gly Arg
                245                 250                 255

Thr Arg Ser Asp Ile Val Ser Arg Ala Leu Asp Leu Phe Ser Asp Asn
            260                 265                 270

Ala Pro Pro Glu Leu Leu Glu Ile Ile Asn Glu Asp Ile Ala Lys
        275                 280                 285

Arg Thr Cys Glu Glu His Gln Leu Cys Val Val Ala Val Leu Pro His
    290                 295                 300

Ile Leu Asp Thr Gly Ala Ala Gly Arg Asn Ser Tyr Leu Glu Val Leu
305                 310                 315                 320

Leu Lys Leu Ala Asp Lys Tyr Lys Lys Met Trp Gly Trp Leu Trp
                325                 330                 335

Thr Glu Ala Gly Ala Gln Ser Glu Leu Glu Thr Ala Leu Gly Ile Gly
            340                 345                 350
```

-continued

```
Gly Phe Gly Tyr Pro Ala Met Ala Ala Ile Asn Ala Arg Lys Met Lys
            355                 360                 365

Phe Ala Leu Leu Lys Gly Ser Phe Ser Glu Gln Gly Ile Asn Glu Phe
370                 375                 380

Leu Arg Glu Leu Ser Phe Gly Arg Gly Ser Thr Ala Pro Val Gly Gly
385                 390                 395                 400

Gly Ala Phe Pro Thr Ile Val Glu Arg Glu Pro Trp Asp Gly Arg Asp
                405                 410                 415

Gly Glu Leu Pro Val Glu Asp Asp Ile Asp Leu Ser Asp Val Glu Leu
            420                 425                 430

Asp Asp Leu Gly Lys Asp Glu Leu
            435                 440

<210> SEQ ID NO 15
<211> LENGTH: 405
<212> TYPE: DNA
<213> ORGANISM: Homo sapiens

<400> SEQUENCE: 15
atggctgtct tggggctgct cttctgcctg gtgacattcc caagctgtgt tctatcccag      60
gtgcacctga agcagtcagg acctggccta gtgcagccct cacagagcct gtccatcacc     120
tgcacagtct ctggtttctc attaactaac tatggtgtcc actgggttcg ccagtctcca     180
ggaaagggtc tggagtggct gggagtgata tggagtggtg gattcactga ctctactgca     240
gctttcatat ccagactgag catcagcaag gacaattcca agagccaagt tttcttttaa     300
atgaacagtc tgcaaactga tgacacagcc atatattact gtgccagaaa gggcgggtat     360
gctatggact actggggtca aggaacctca gtcaccgtct cctca                    405

<210> SEQ ID NO 16
<211> LENGTH: 135
<212> TYPE: PRT
<213> ORGANISM: Homo sapiens

<400> SEQUENCE: 16

Met Ala Val Leu Gly Leu Leu Phe Cys Leu Val Thr Phe Pro Ser Cys
1               5                   10                  15

Val Leu Ser Gln Val His Leu Lys Gln Ser Gly Pro Gly Leu Val Gln
                20                  25                  30

Pro Ser Gln Ser Leu Ser Ile Thr Cys Thr Val Ser Gly Phe Ser Leu
            35                  40                  45

Thr Asn Tyr Gly Val His Trp Val Arg Gln Ser Pro Lys Gly Leu
    50                  55                  60

Glu Trp Leu Gly Val Ile Trp Ser Gly Gly Phe Thr Asp Ser Thr Ala
65                  70                  75                  80

Ala Phe Ile Ser Arg Leu Ser Ile Ser Lys Asp Asn Ser Lys Ser Gln
                85                  90                  95

Val Phe Phe Lys Met Asn Ser Leu Gln Thr Asp Asp Thr Ala Ile Tyr
            100                 105                 110

Tyr Cys Ala Arg Lys Gly Gly Tyr Ala Met Asp Tyr Trp Gly Gln Gly
        115                 120                 125

Thr Ser Val Thr Val Ser Ser
    130                 135

<210> SEQ ID NO 17
<211> LENGTH: 393
<212> TYPE: DNA
<213> ORGANISM: Homo sapiens
```

<400> SEQUENCE: 17

```
atggattttc aggtgcagat tttcagcttc ctgctaatca gtgcctcagt cttaatgtcc      60
agaggacaaa ttgttctcac ccagtctcca gcaatcatgt ctgcatctct aggggaacgg    120
gtcaccatga cctgcactgc cagctcaagt gtaagttcca gttacttgca ctggtaccag    180
cagaagccag gatcctcccc caaactctgg attttagca catccaacct ggcttctgga     240
gtcccagctc gcttcagtgg cagtgggtct gggacctctt actctctcac aatcagcagc    300
atggaggctg aagatgctgc cacttattac tgccaccagt atcatcgttc cccattcacg    360
ttcggctcgg ggacaaagtt ggaaataaaa cgg                                  393
```

<210> SEQ ID NO 18
<211> LENGTH: 131
<212> TYPE: PRT
<213> ORGANISM: Homo sapiens

<400> SEQUENCE: 18

```
Met Asp Phe Gln Val Gln Ile Phe Ser Phe Leu Leu Ile Ser Ala Ser
  1               5                  10                  15
Val Leu Met Ser Arg Gly Gln Ile Val Leu Thr Gln Ser Pro Ala Ile
             20                  25                  30
Met Ser Ala Ser Leu Gly Glu Arg Val Thr Met Thr Cys Thr Ala Ser
         35                  40                  45
Ser Ser Val Ser Ser Ser Tyr Leu His Trp Tyr Gln Gln Lys Pro Gly
     50                  55                  60
Ser Ser Pro Lys Leu Trp Ile Phe Ser Thr Ser Asn Leu Ala Ser Gly
 65                  70                  75                  80
Val Pro Ala Arg Phe Ser Gly Ser Gly Ser Gly Thr Ser Tyr Ser Leu
                 85                  90                  95
Thr Ile Ser Ser Met Glu Ala Glu Asp Ala Ala Thr Tyr Tyr Cys His
            100                 105                 110
Gln Tyr His Arg Ser Pro Phe Thr Phe Gly Ser Gly Thr Lys Leu Glu
        115                 120                 125
Ile Lys Arg
    130
```

<210> SEQ ID NO 19
<211> LENGTH: 60
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 19

```
gatcttatgt caagttgtat agttattcaa gagataacta tacaacttga catattttg      60
```

<210> SEQ ID NO 20
<211> LENGTH: 60
<212> TYPE: DNA
<213> ORGANISM: Artificial Sequence
<220> FEATURE:
<223> OTHER INFORMATION: Description of Artificial Sequence:
      Synthetic Primer

<400> SEQUENCE: 20

```
aattcaaaaa tatgtcaagt tgtatagtta tctcttgaat aactatacaa cttgacataa      60
```

NEGATIVE IMMUNOMODULATION OF IMMUNE RESPONSES BY ERP5

This application claims priority to U.S. Provisional Patent application Ser. No. 60/913,467 filed Apr. 23, 2007, entitled "Negative Immunomodulation of Immune Responses by ERp5," which is incorporated herein by reference in its entirety.

This invention was made with government support under grant R37 AI30581 awarded by the National Institutes of Health. The government has certain rights in the invention.

BACKGROUND OF THE INVENTION

I. Field of the Invention

The present invention relates to methods of treating disorders having an aberrant immune response component, including cancers and autoimmune disorders. These methods relate in particular to inhibiting or stimulating the immunomodulatory function of ERp5 located on the surface of tumor cells, activated T-cells, dendritic cells, and other cell types.

II. Background

Receptors that inhibit or activate natural killer (NK) cells can be expressed on T cells where they modulate T cell antigen receptor (TCR)-CD3 complex-dependent responses. Among these receptors is NKG2D, which interacts with ligands that are absent from most normal cells but can be transcriptionally induced by generic mechanisms of chromatin remodeling and cellular stress. In humans, NKG2D ligands include the major histocompatibility complex class I-related chain A polypeptide (MICA), which is frequently associated with epithelial tumors, induced by microbial infections, and aberrantly expressed in certain autoimmune disease lesions. Upon ligand engagement, NKG2D conveys directly activating or costimulatory signals via the paired DAP10 adaptor protein. NKG2D may thus promote cancer and infectious disease immunity but worsen autoimmune disease progression.

Consistent with its role in effector responses, NKG2D is present on virtually all NK cells and CD8 T cells but absent on most CD4 T cells. One exception to this rule is seen in rheumatoid arthritis (RA), where the severity of autoimmune and inflammatory joint disease correlates with large numbers of autoreactive CD4 T cells with NKG2D expression that is cytokine (IL-15 and TNF-α) induced (induced NKG2D$^+$ CD4$^+$ T cells). These T cells are cytotoxic, produce inflammatory cytokines, and are stimulated by RA synoviocytes which have aberrant expression of the NKG2D ligand MICA. Thus, NKG2D binding to synoviocyte MICA may promote the self-perpetuating pathology in RA and presumably certain other autoimmune diseases as well (Groh et al., 2003).

Large expansions of NKG2D$^+$CD4$^+$ T cells have also been reported in cancer patients with tumors that express membrane-bound MIC and shed soluble MICA and presumably MICB. As with the NKG2D$^+$CD4$^+$ T cells in RA, these T cells are autoreactive; however, their expression of NKG2D is constitutive and not cytokine induced and they are non-cytotoxic (constitutive NKG2D$^+$CD4$^+$ T cells). Moreover, the NKG2D$^+$CD4$^+$ T cells in cancer patients have suppressor functions and thus resemble regulatory T cells. They produce IL-10 and TGFβ, and secrete Fas ligand (FasL), causing growth arrest of other T cells that lack NKG2D signaling, which protects from Fas/FasL-mediated cell cycle arrest (Groh et al., 2006). The increased frequencies of the NKG2D$^+$CD4$^+$ T cells in cancer patients result from proliferative expansions that are driven by NKG2D costimulation upon binding of membrane-associated or soluble MIC ligands. Thus, shedding of the soluble MIC ligands of NKG2D negatively imprints on immune responses, thus enabling tumor immune evasion. Moreover, soluble MICA induces downmodulation and degradation of NKG2D on NK cells and CD8 T cells, thus diminishing anti-tumor effector responses (Groh et al., 2001).

Central to this application is the mechanism of shedding, which is enabled by endoplasmic reticulum protein 5 (ERp5), a disulphide isomerase family member. ERp5 and MIC form mixed disulphide complexes on the surface of tumor cells, from which soluble MICA (and MICB) is released after proteolytic cleavage near the cell membrane. This mechanism involves reduction of the disulphide bond in the membrane-proximal α3 of MIC proteins, which presumably imposes a large conformational change that enables cleavage. By enabling the shedding of MIC proteins, ERp5 thus promotes expansions of 'immunosuppressive' type NKG2D$^+$CD4$^+$ T cells (constitutive NKG2D$^+$CD4$^+$ T cells), as well as impairment of NK cell and CD8 T cell functions via NKG2D downmodulation and degradation, in cancer patients.

Pertinent to this application, ERp5 is also present on activated T cells and monocyte-derived dendritic cells (DC). Binding of soluble MIC proteins to ERp5 induces a signaling event, presumably through an associated effector protein, which results in altered cytokine production by T cells and DC, and impairs maturation of DC.

SUMMARY OF THE INVENTION

In accordance with the present invention, there is provided a method of preventing ERp5 modulation of immune cell function or immune cell development comprising contacting an immune cell expressing ERp5 with an inhibitor of ERp5 function or expression. The inhibitor may be an inhibitor of MIC binding to ERp5, an inhibitor of ERp5 isomerase function, or an inhibitor of ERp5 expression. The MIC may be MICA and/or MICB. The MIC may be soluble or membrane-bound. In certain aspects, peroxiredoxin-4 can be modulated alone or in combination with ERp5 modulation to modulate the immune function of a cell or subject. The immune cell may be a dendritic cell or a T cell. The immune cell function may comprise cellular proliferation and/or interleukin production or dendritic cell maturation. The immune cell may be a human immune cell, for example, a human immune cell located in a human subject. The human subject may suffer from cancer, such as a MIC-related cancer (i.e., a cancer associated with elevated levels of soluble MIC or a cancer susceptible to treatment by methods modulating MIC activity).

The inhibitor may be an anti-MIC and/or anti-Prx-4 antibody, for example, one that binds to soluble MIC (A or B) or to membrane-bound MIC (A or B), or Prx-4, respectively. The antibody may be a bi-specific antibody comprising (a) one binding region that is specific for soluble MIC, and (b) one binding region that is specific for surface-bound MIC or Prx-4. In particular, the antibody may be directed to a MIC (A or B) α3 domain. The inhibitor may also be an anti-ERp5 antibody, such as one that prevents MIC shedding, that prevents soluble MIC binding to ERp5, or one that is a bi-specific and (a) prevents MIC shedding, and (b) prevents soluble MIC binding to ERp5. The inhibitor may be an antibody that binds a non-ERp5 receptor on said immune cell, wherein said non-ERp5 receptor participates in the binding of MIC to ERp5. The inhibitor may be a MIC mimetic or fragment that binds but does not activate ERp5, or an ERp5 mimetic or fragment that binds soluble MIC.

In another embodiment, there is provided a method of inhibiting immune cell function or immune cell development comprising contacting an immune cell with MIC or MIC mimetic that binds to ERp5. The MIC may be MICA and/or MICB. The immune cell can be a dendritic cell or a T cell. The immune cell function may be proliferation, interleukin production, or dendritic cell maturation. The immune cell may be a human immune cell, for example, a human immune cell located in a human subject. The human subject may suffer from an autoimmune disease. The autoimmune disease may be RA, SLE, sclerodema, MS, Crohn's disease, celiac disease, inflammatory bowel disease, rheumatoid arthritis, insulin-dependent diabetes mellitus (type 1), multiple sclerosis, Wegener's granulomatosis, Sjogren's syndrome, systemic lupus erythematosus, myasthenia gravis, Reiter's syndrome, Grave's disease, Hashimoto's thyroiditis, pernicious anemia, Addison's disease, dermatomyositis, polymyositis, GVHD and Guillain Barré.

In yet another embodiment, there is provided a monoclonal antibody that binds immunologically to a MIC α3 domain. The antibody may be humanized from an animal antibody, such as a murine antibody, or may be human. The antibody may be chimeric. The antibody may be bi-specific for the MIC α3 domain and another determinant. The antibody may be formulated in a pharmaceutical preparation. Also provide is a cell, such as a hybridoma, that produces a monoclonal antibody that binds immunologically to a MIC (A and/or B) α3 domain. Exemplary variable region sequences are shown in SEQ ID NOS:15-18.

Another embodiment comprises a method of screening for an agent that modulates the interaction of ERp5 and MICA/MICB comprising (a) providing isolated ERp5 or MICA/MICB-binding fragment thereof; (b) contacting ERp5 with MICA/MICB or an ERp5-binding fragment thereof in the presence of a candidate substance; and (c) assessing binding of ERp5 to MICA/MICB, wherein altered binding of ERp5 to MICA/MICB, as compared to binding in the absence of the candidate substance, indicates that the candidate substance is an agent that modulates the interaction of ERp5 and MICA/MICB comprising. The candidate substance may be a peptide, protein, an RNA, a DNA, an organopharmaceutical, or a lipid. The candidate substance may be MICA, MICB, and specific antibodies or any other agents that interfere with ERp5-MIC interactions.

Alternatively, the human subject may suffer from an infection, such as with a virus, bacterium, fungus or parasite, wherein the infectious agent has evaded or suppressed the immune response in the subject, and the inhibitor would override or compensate for that evasion or suppression.

It is contemplated that any method or composition described herein can be implemented with respect to any other method or composition described herein.

The use of the word, "a" or "an" when used with the term "comprising" in the specification and/or claims may mean "one," "one or more," "at least one," or "one or more than one."

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

The terms "inhibiting," "reducing," or "prevention," or any variation of these terms, when used in the claims and/or the specification includes any measurable decrease or complete inhibition to achieve a desired result.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed herein can be implemented with respect to any method or composition of the invention, and vice versa. Furthermore, compositions and kits of the invention can be used to achieve methods of the invention.

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 1A) Flow cytometry confirms MICA (filled profiles) and ULBP2 (lightly shaded profiles) tetramer binding to NKL cells and inhibition by anti-NKG2D mAb 1D11 (shaded profiles). MICA but not ULBP2 tetramers bind to NKG2D⁻ U266, Hela, HCT116, Lovo, and A375 tumor cells and binding is inhibited by bacterial rMICA (shaded profiles). U937 cells are negative for MICA tetramer binding. Open profiles are control IgG stainings. (FIG. 1B) Silver staining of U266 and U937 outer cell membrane proteins enriched for binding to MICA beads. Trx, thioredoxin. (FIG. 1C) Probing of MICA bead-purified proteins from surface biotinylated cells with streptavidin-HRP or specific antisera. Two additional bands in the anti-ERp5 lane are cross-reactive. (FIG. 1D) Anti-ERp5 stainings (filled profiles). Open profiles are IgG controls.

(FIG. 2A) Freshly isolated melanoma, breast, and ovarian tumor cells are positive for MICA, tetramer binding, and surface ERp5. Matched patient peripheral blood serum samples contain the indicated amounts of sMICA. Data are representative of five matched sample pairs. (FIG. 2B) DTNB and PAO reduce shedding of sMICA by Hela and A375 cells in a dose-dependent manner as determined by ELISA. Similar results were obtained with HCT116 and Lovo cells. (FIG. 2C) PAO interferes with MICA tetramer binding.

(FIG. 3A) Expression of siRNA constructs 17 or 19 in A375 cells results in ~70-80% reductions of ERp5 mRNA by real-time RT-PCR. (FIG. 3B) Knock-down of ERp5 mRNA decreases MICA tetramer binding and ERp5 surface expression (filled profiles in center and right columns; shaded profiles represent negative controls). MICA expression (filled profiles in left column) is unchanged; open profiles represent IgG control stainings. (FIG. 3C) Knock-down of ERp5 mRNA diminishes sMICA shedding as determined by ELISA. Control bars (Ctrl) in (FIG. 3A) and (FIG. 3C) and control profiles in (FIG. 3B) represent mock-transduced cells or cells expressing irrelevant siRNA.

(FIG. 4A) Treatment of surface biotinylated Hela cells with TCA before lysis, MICA immunoprecipitation, SDS-PAGE and membrane transfer reveals MICA-ERp5 complexes (lane 1). Protein identities are confirmed by secondary precipitations (lanes 7, 8, 10), primary precipitations of ERp5 (lanes 5, 6) and by rERp5 (lane 11). After cell culture in the presence of dRNase, co-immunoprecipitated ERp5 increases (lanes 2-4), full-length MICA disappears and sMICA emerges (lanes 3, 4). sMICA identity is confirmed by secondary precipitation (lane 9) and comparison to sMICA from cell culture media (lane 12). (FIG. 4B) Control experiment with cells grown in the presence of native RNase. (FIG. 4C) dRNase promotes sMICA shedding. Error bars represent deviations among 3 experiments.

FIGS. 5A-5E—ERp5 exhibits specificity for the MICA α3 domain. (FIG. 5A) ERp5 organisation with CGHC motifs within thioredoxin domains (open boxes). Upper numbers identify amino acid positions at domain boundaries; lower numbers identify cysteine positions and truncation sites of expressed ERp5 fragments. (FIG. 5B) MICA is partially reduced by ERp5$_{1-118}$. (FIG. 5C) MICA and the C39S mutant (C39*) of ERp5$_{1-118}$ form mixed disulfide heterodimers (asterisk) which are resolved by β-ME. C39*ERp5$_{1-118}$ partially forms homodimers (see also FIG. 5E). (FIG. 5D) ERp5 has no effect on the MICA α1α2 domain. Partial reduction in lane 2 is due to bleeding of β-ME from lane 1. (FIG. 5E) C39*ERp5$_{1-118}$ reduces the MICA α3 disulfide bond as indicated by unresolved heterodimers (asterisk). Filled and open arrow heads on the right of FIGS. 5B-D mark positions of non-reduced and reduced forms, respectively, of MICA substrates.

FIGS. 6A-6C—Specific reduction of MICA by ERp5 in vitro. (FIG. 6A) ERp5 and MICA run at their expected molecular weights when analysed under reducing conditions (β-ME). Unreduced MICA displays increased electrophoretic mobility consistent with stable intrachain disulfide linkages. Co-incubation of MICA and ERp5 for 1 h or 3 h reveals progressive MICA reduction. (FIGS. 6B-C) No reduction by ERp5 is apparent in Siderocalin and CD94-NKG2A.

FIG. 7D: PHA (or anti-CD3)-activated NKG2D$^+$CD4$^+$ T cells are stimulated by anti-NKG2D and soluble MICA to produce similar quantities of IL-10 and TGFβ. But the amounts of IL-1β, granulocyte colony-stimulating factor (G-CSF) and monocyte chemoattractant protein 1 (MCP1) are increased in the presence of soluble MICA but not of anti-NKG2D. FIG. 7C: Similarly increased amounts of IL-1β, G-CSF, and MCP1 were also produced by NKG2D$^-$CD4$^+$ T cells, thus precluding an effect of NKG2D, in the presence of soluble MICA. This effect of soluble MICA is thus presumably mediated by ERp5 upon binding of soluble MICA.

FIG. 8A shows IgG negative control staining. Expression of DC maturation markers (CD83 and CD80, as well as an IgG control) is diminished on mDC matured in the presence of soluble MICA (not shown). FIG. 8C: IL-6 secretion by matured DC is impaired by the additional presence of MICA on irradiated C1R-MICA cell transfectants but not C1R-ULBP1 transfectants. ULBP1 is another ligand of NKG2D. Results from 4 experiments are shown; quantitative differences between experiments are due to differences in cell numbers and donor variation. Untransfected C1R cells serve as negative control. The ability of mDC to present alloantigen and stimulate T cells in the presence of soluble MICA, as measured by standard T cell thymidine incorporation proliferation assay was also reduced (not shown).

DETAILED DESCRIPTION OF THE INVENTION

Figure 1A:
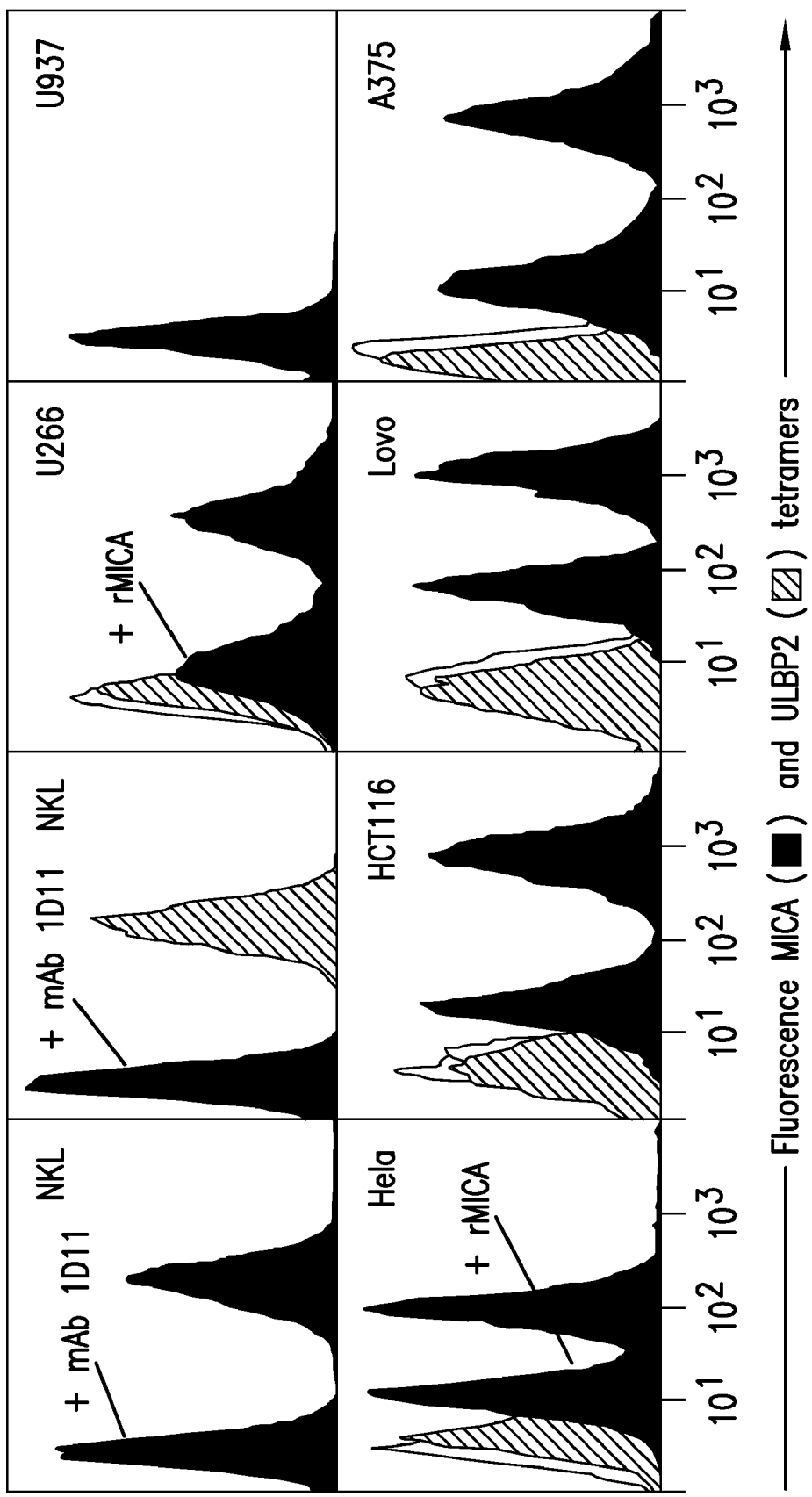
FIGS. 1A-1D—Surface interactions of MICA with ERp5 and GRP78.

The present invention addresses the function of ERp5, an endoplasmic reticulum protein of the protein disulphide isomerase (PDI) family with which MICA specifically associates. The inventors have previously shown that pharmacological inhibition of thioreductase catalytic activities and siRNA-mediated silencing of ERp5 expression profoundly reduce shedding of soluble MICA and thus prevent its negative effects on the immune system, i.e., down-modulation of NKG2D and down-modulation of population expansions of 'suppressor' type NKG2D$^+$CD4$^+$ T cells (constitutive NKG2D$^+$CD4$^+$ T cells) in cancer patients. The inventors have also shown that ERp5-mediated reduction of an intradomain disulphide bond of MICA causes a conformational destabilization that is a necessary prerequisite for proteolytic cleavage (by a distinct proteolytic entity) within the peptide sequence that connects the proximal α3 domain to the cell membrane.

The inventors now show that ERp5 has an impact on immune cells, such as T cells and dendritic cells, that express it. Not only is ERp5 associated in the release of MICA, but it is also involved in the downstream signaling process of MICA on target cells. MICA (and presumably MICB) binds to ERp5 on activated T cells and dendritic cells, altering their function and/or inhibiting maturation. By targeting the interaction of MICA with ERp5 on T cells and dendritic cells, and the cell signaling associated with MICA interaction with ERp5 and other molecules that exist on T cells and dendritic cells, the immunomodulatory functions of ERp5 can be modulated positively or negatively, e.g., inhibited or stimulated.

As used herein, the following terms have the meanings ascribed to them unless specified otherwise.

As used herein, "T cells" refers to a sub-population of lymphocytes that mature in the thymus, and which display, among other molecules, T cell receptors on their surface. T cells can be identified by virtue of certain characteristics and biological properties, such as the expression of specific surface antigens including the TCR, CD3, CD4 or CD8, the ability of certain T cells to kill tumor or infected cells, the ability of certain T cells to activate other cells of the immune system, and the ability to release protein molecules called cytokines or other soluble mediators that stimulate or inhibit the immune response. Any of these characteristics and activities can be used to identify T cells using methods well known in the art.

The term "NKG2D" refers to an activating cell surface molecule that is found consistently on all or a fraction of numerous types of immune cells, particularly NK cells, $CD8^+$ T cells, some $CD4^+$ T cells, and γ/δ T cells. NKG2D is also referred to as natural killer group 2, member D; also called KLRK1, receptor (see, e.g., OMIM 602893, the entire disclosure of which is herein incorporated by reference in its entirety). As used herein NKG2D refers to any NKG2D isoform. In NK and T cells, NKG2D forms hexameric complexes in which a NKG2D homodimer is paired with four DAP10 signaling polypeptides (see, e.g., OMIM 604089). It will be appreciated that any activity attributed herein to NKG2D, e.g., cell activation, recognition by antibodies, etc., can also refer to NKG2D-including complexes such as NKG2D-DAP10 and other associated molecules.

"Autoimmune" disorders include any disorder, condition, or disease in which the immune system mounts a reaction against self cells or tissues, due to a breakdown in the ability to distinguish self from non-self or otherwise. Examples of autoimmune disorders include Hashimoto's thyroiditis, pernicious anemia, Addison's disease, type I diabetes, rheumatoid arthritis, systemic lupus erythematosus, dermatomyositis, Crohn's disease, celiac disease, inflammatory bowel disorder, Sjogren's syndrome, lupus erythematosus, multiple sclerosis, myasthenia gravis, Reiter's syndrome, Grave's disease, polymyositis, Guillain Barré, Wegener's granulomatosus, polyarteritis nodosa, polymyalgia rheumatica, temporal arteritis, Bechet's disease, Churg-Strauss syndrome, Takayasu's arteritis, and others. Autoimmune disorders can involve any component of the immune system, and can target any cell or tissue type in the body.

"Cancer" refers to any hyperproliferative disorder, but in particular, it refers to malignancies involving almost any tissue, including brain, head & neck, esophagus, mouth & gums, trachea, lung, breast, stomach, colon, liver, pancreas, kidney, rectum, ovary, uterus, cervix, testes, prostate, bladder, penis, vagina or blood. Cancer also refers to cancers that are primary, metastatic, recurrent and drug resistant. An "epithelial cancer" is one that is derived from an epithelial tissue and may occur in any location of the body, including ovarian cancer, squamous cell carcinoma, thyroid cancer, mammary neoplasia, and basal cell carcinoma. A "MIC-related cancer" is one that is characterized by MIC production by the cancer cell/tumor.

"Dendritic cells" are immune cells that form part of the mammalian immune system. Their main function is to process antigen material and present it on their surface to other cells of the immune system. Dendritic cells are present in small quantities in tissues that are in contact with the external environment, mainly the skin (where they are often called Langerhans cells) and the inner lining of the nose, lungs, stomach and intestines. They can also be found at an immature state in the blood. Once activated, they migrate to the lymphoid tissues where they interact with T cells to initiate and shape the immune response. At certain development stages they grow branched projections, the dendrites, that give the cell its name, but do not have any special relation with neurons, which also possess similar appendages. Immature dendritic cells are also called veiled cells, in which case they possess large cytoplasmic 'veils' rather than dendrites.

The terms "reducing," "interfering," "inhibiting," "down-modulating," "antagonize," and "down-regulating," with respect to NKG2D or NKG2D-expressing cells means a process, method, or compound that can slow, reduce, reverse, or in any way negatively affect the activity or number of NKG2D receptors or the number of cells expressing NKG2D. These terms can refer to compounds that inhibit the activation of NKG2D by a ligand, that act antagonistically in the absence of a ligand to decrease the activity of the receptor, that decrease the expression level of the receptor, that block NKG2D-triggered signaling and/or gene expression, or that block any other activity of the cell that results from NKG2D activation. In a particular embodiment, the inhibiting compound or method targets the binding of the receptor by a ligand, e.g., by binding to the receptor and preventing ligand access. Alternatively, the inhibiting compound may interference with the production, processing or secretion of MICA and/or MICB.

The term "antibody," as used herein, refers to polyclonal and monoclonal antibodies. Depending on the type of constant domain in the heavy chains, antibodies are assigned to one of five major classes: IgA, IgD, IgE, IgG, and IgM. Several of these are further divided into subclasses or isotypes, such as IgG1, IgG2, IgG3, IgG4, and the like. An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids that is primarily responsible for antigen recognition. The terms variable light chain ($V_L$) and variable heavy chain ($V_H$) refer to these light and heavy chains respectively. The heavy-chain constant domains that correspond to the different classes of immunoglobulins are termed "alpha," "delta," "epsilon," "gamma" and "mu," respectively. The subunit structures and three-dimensional configurations of different classes of immunoglobulins are well known. IgG and/or IgM are the preferred classes of antibodies employed in this invention, with IgG being particularly preferred, because they are the most common antibodies in the physiological situation and because they are most easily made in a laboratory setting. In certain aspects, the antibody of this invention is a monoclonal antibody. In still further aspects the antibodies are humanized, bispecific, chimeric, human, or otherwise-human-suitable antibodies. "Antibodies" also includes any fragment or derivative of any of the herein described antibodies.

The term "specifically binds to" means that a ligand that can bind preferably in a competitive binding assay to the binding partner, as assessed using either recombinant forms of the proteins, epitopes therein, or native proteins present on the surface of isolated T or NK or other target cells. Competitive binding assays and other methods for determining specific binding (e.g., antibody masking) are further described below and are well known in the art.

A "human-suitable" or "humanized" antibody refers to any antibody, derivatized antibody, or antibody fragment that can be safely used in humans for, e.g., the therapeutic methods described herein. Human-suitable antibodies include all types of chimeric or fully human antibodies, or any antibodies in which at least a portion of the antibodies is derived from humans or otherwise modified so as to avoid the immune response that is generally provoked when native non-human antibodies are used.

For the purposes of the present invention, a "humanized" antibody refers to an antibody in which the constant and variable framework region of one or more human immunoglobulins is fused with the binding region, e.g., the CDR, of an animal immunoglobulin. Such humanized antibodies are designed to maintain the binding specificity of the non-human antibody from which the binding regions are derived, but to avoid an immune reaction against the non-human antibody.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

A "humanized" antibody is an antibody obtained from transgenic mice or other animals that have been "engineered" to produce specific human antibodies in response to antigenic challenge (see, e.g., Green et al., 1994; Lonberg et al., 1994; Taylor et al., 1994, the entire teachings of which are herein incorporated by reference). A fully human antibody also can be constructed by genetic or chromosomal transfection methods, as well as phage display technology, all of which are known in the art (see, e.g., McCafferty et al., 1990). Human antibodies may also be generated by in vitro activated B cells (see, e.g., U.S. Pat. Nos. 5,567,610 and 5,229,275, which are incorporated in their entirety by reference).

Within the context of this invention, "active" or "activated" T cells designate biologically active T cells, more particularly T cells having the capacity of cytolysis or of stimulating an immune response by, e.g., secreting cytokines.

The terms "isolated", "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified.

The term "biological sample" as used herein includes but is not limited to a biological fluid (for example serum, lymph, blood), cell sample or tissue sample (for example bone marrow, tumor biopsy).

The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under expressed or not expressed at all.

I. PROTEIN DISULFIDE ISOMERASE ERP5 AND ERP5 AGONISTS AND ANTAGONISTS

Formation and rearrangement of disulfide bonds during the correct folding of nascent proteins is modulated by a family of enzymes known as thiol isomerases, which include protein disulfide isomerase (PDI), endoplasmic reticulum protein 5 (ERp5) and ERp57. Recent evidence supports an alternative role for this family of proteins on the surface of cells, where they are involved in receptor remodeling and recognition. The nucleic acid and protein sequences for ERp5 can be found in SEQ ID NOS:13 and 14. The inventors have discovered that ERp5 is associated with perioxiredoxin-4 (Prdx-4 or Prx-4) on the surface of some cells including tumor cells and activated T cells. Peroxiredoxins are novel peroxidases that exhibit divergent biological functions. The fourth member, Prx-4, is synthesized with a signal sequence and, after processing, secreted as a 27-kDa form in most tissues. The active site is the redox-active Cys-124 oxidized to Cys-SOH. Cys-SOH rapidly reacts with Cys-245-SH of the other subunit to form an intermolecular disulfide with a concomitant homodimer formation. The enzyme may be subsequently regenerated by reduction of the disulfide by thioredoxin. Prx-4 activates NF-κB and induces the degradation of the inhibitory subunit of NF-κB. In addition, Prx-4 up-regulates the expression of NF-κB-dependent gene products, ICAM-1, and inducible nitric oxide synthase. Prx-4 also activates c-Jun N-terminal kinase and induces the proliferation of normal human foreskin fibroblasts. Its homology with antioxidant proteins, wide distribution in tissues, and ability to activate NF-κB and c-Jun N-terminal kinase suggest that Prx-4 plays an important role in inflammation (Haridas et al., 1998; U.S. Pat. No. 6,605,278, each of which is incorporated herein by reference in their entirety).

In platelets, blocking PDI with inhibitory antibodies inhibits a number of platelet activation pathways, including aggregation, secretion, and fibrinogen binding. Analysis of human platelet membrane fractions identified the presence of the thiol isomerase protein ERp5. Further study showed that ERp5 is resident mainly on platelet intracellular membranes, although it is rapidly recruited to the cell surface in response to a range of platelet agonists. Blocking cell-surface ERp5 using inhibitory antibodies leads to a decrease in platelet aggregation in response to agonists, and a decrease in fibrinogen binding and P-selectin exposure. It is possible that this is based on the disruption of integrin function, as the authors observed that ERp5 becomes physically associated with the integrin β(3) subunit during platelet stimulation (Jordan et al., 2005). Precedent for other biological functions of surface thiol isomerases further includes CD4 homodimer formation by interchain disulfide exchange, which enables HIV-1 T cell infection (Matthias et al., 2002), and switching of cell surface tissue factor functional states between activation of coagulation and G-protein-coupled signaling (Ahamed et al., 2006).

A. ERp5 Agonists

Agonists for ERp5 are primarily considered to be the natural ligands for ERp5—MICA/MICB—and ERp5-binding mimetics thereof. However, small molecules that stimulate the expression of ERp5 or enhance its function, also are contemplated. The term agonist as used in the context of ERp5 includes regulation of ERp5 association with other proteins and factors that may be sequestered by ERp5 or otherwise released when ERp5 interacts with an "agonist." In other words an agonist binding ERp5 stimulates further signaling directly or indirectly from ERp5, typically by the release of additional factors that stimulate a cellular response.

B. ERp5 Antagonism

1. Targeting ERp5 Expression

Inhibitors of ERp5 may comprise an inhibitor of ERp5 expression. Inhibitors of ERp5 expression include antisense, ribozyme, and siRNA molecules that target ERp5 coding sequences and/or transcription/translation signals. Drugs (organopharmaceuticals) may be provided that down-regulate the expression of ERp5 either directly, by interfering with ERp5 transcription or translation, or by acting upstream and downregulating an agent that promotes ERp5 transcription or translation.

2. Targeting ERp5 Function

Other antagonists include binding agents for ERp5, such as antibodies to or fragments of MICA and MICB. Drugs (organopharmaceuticals) may be provided that down-regulate the intracellular processing or cell-surface transport of the ERp5.

MIC Fragments. As discussed above, MIC and fragments thereof may be considered as agonists of ERp5. However, MIC derivatives and fragments that bind but do not activate ERp5 would be considered antagonists as they (a) would not activate ERp5 and (b) would prevent activation of ERp5 by MIC by preventing interaction of these molecules. One such agonist is a fragment comprising or consisting of the α3 domain of MICA or MICB, or a portion thereof. Various MIC fragments can be engineered that inhibit the proper function of ERp5. Such fragments would bind ERp5 yet not trigger significant release or activation of any down stream modulators thus blocking wild type MIC from asserting any significant effect on a target cell. In general, such MIC fragments may comprise 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 90, 100 or more consecutive residues of MICA or MICB. The fragments may be fused to other peptide sequences, and may be produced recombinantly or using automated chemical peptide synthesis procedures that are well known in the art.

Anti-MIC Antibodies. Of particular interest in the present invention are antibodies directed to the α1, α2, and/or α3 domain of MICA or MICB. The inventors have generated antibodies having such specificity, the variable sequences for such being provided as SEQ ID NOS:15-18. Such sequences may be cloned into appropriate antibody "framework" expression cassettes, transferred into suitable host cells, and the resulting MIC α3 domain-specific antibodies obtained.

II. NKG2D

NKG2D, a homodimeric C-type lectin-like receptor, is a unique stimulatory molecule that is found on natural killer (NK) cells CD8 αβ T cells and γδ T cells. Typically, it is associated with an adaptor protein, designated DAP10, through oppositely charged amino acid residues in their transmembrane domains. DAP10 signals similarly to the CD28 co-stimulatory receptor by activation of phosphatidylinositol 3-kinase (PI3K) upon phosphorylation of a YxxM motif in its cytoplasmic domain. The deglycosylated NKG2D polypeptide chain is of 28 kilodalton (kD). It is encoded by a gene in the NK complex (NKC) on human chromosome 12. Despite its name, NKG2D shares no significant sequence homology with the NKG2A and NKG2C/H receptors that associate with CD94. NKG2D homodimers form stable complexes with monomeric MICA in solution. Soluble NKG2D also binds to cell surface MICB, which has structural and functional properties similar to those of MICA (Steinle et al., 2001).

The inventors have shown that NKG2D functions as a receptor for MICA and MICB using biochemical and genetic methods (Bauer et al., 1999). Prior to this finding, the function of NKG2D was unknown. The inventors determined that NKG2D has a very broad distribution on lymphocyte subsets, being expressed on most NK cells, CD8 α/β T cells and γ/δ T cells. Functional experiments showed that engagement of NKG2D activates cytolytic responses of γ-delta T cells and NK cells against transfectants and epithelial tumor cells expressing MIC (Groh et al., 1999; Bauer et al., 1999). These results define an activating immunoreceptor-MHC ligand interaction that may promote antitumor NK and T cell responses. Furthermore, the inventors showed that interactions of MIC with NKG2D potently augment cytolytic responses of antigen-specific CD8 α/β T cell responses and co-stimulate cytokine production and T cell proliferation (Groh et al., 2001).

NKG2D interacts with the MHC class I-related MICA and MICB glycoproteins (discussed below) among other ligands (Bauer et al., 1999). These have no role in antigen presentation, have a restricted tissue distribution in intestinal epithelium, and can be stress-induced in permissive types of cells by viral and bacterial infections, malignant transformation and proliferation (Groh et al., 1996; Groh et al., 1998; Das et al., 2001; Groh et al., 2001; Tieng et al., 2002). Ligand engagement of NKG2D activates NK cells and potently costimulates effector T cells (Bauer et al., 1999; Das et al., 2001; Groh et al., 2001). NKG2D lacks a paired antagonist receptor. However, the expression of NKG2D is controlled by ligand-induced down-modulation, which can be transient and reversed by interleukin-15 in some cells (Groh et al., 2002).

III. MHC CLASS I RELATED CHAINS A AND B

MICA and MICB

Ligands for NKG2D include MICA and MICB, distant relatives of MHC class I molecules that play no role in antigen presentation. Rather, they function as signals of cellular distress. These proteins have a highly restricted tissue distribution in intestinal epithelium and are frequently expressed in epithelial tumors (Groh et al., 1996; Groh et al., 1999) and in synovial tissues of patients with rheumatoid arthritis (Groh et al., 2003).

MICA and MICB proteins (SEQ ID NO: 2 and SEQ ID NO: 4, respectively) are MHC class I related Chains A and B. They are closely related and are encoded by genes 40 and 110 kilobases (kb) centromeric of HLA-B, respectively (Bahram et al., 1994). Sequences directly homologous to MIC are conserved in most mammals except rodents, and thus probably originated at an early stage in mammalian evolution. The translation product of MICA is only distantly similar to mammalian MHC class I chains, but it shares the same domain organization and predictably a similar tertiary structure. An average of 25% of the MICA amino acids in the extracellular α1, α2, and α3 domains match residues in diverse human and mouse, or in any other mammalian MHC class I sequences (Bahram et al., 1994). A further characteristic of MICA is the complete absence of all of the residues implicated in the binding of CD8 and the presence of eight N-linked glycosylation sites in the α1-α3 domain sequences. Moreover, transcription of MICA is restricted to various epithelial cell lines and is not regulated by γ-interferon. MICB mRNA is present in the same cell lines, albeit at very low levels. In epithelial cell lines, transcription of both MICA and MICB can be induced by heat shock in a manner similar to heat shock protein 70 (hsp70), presumably owing to the presence of putative heat shock elements (HSE) in the 5' flanking regions of both MICA and MICB (Groh et al., 1996; Groh et al, 1998). Because of this property, MICA and MICB are cell stress response genes.

The inventors have reported the complete nucleotide sequence of the MICA gene comprising 11,722 basepairs (bp) of DNA 40 kilobases (kb) centromeric of HLA-B. The sequence was obtained from single-stranded (M13) and double-stranded (pUC19) templates of mapped or randomly shot-gun subcloned DNA fragments that were derived from the cosmid M32A (Spies et al., 1989). The first exon encoding the leader peptide is followed by an intron of 6840 bp, which is unusually large for a class I gene. The remainder of the MICA gene shows an organization quite similar to that of conventional class I genes, except for the presence of a relatively long intron following the transmembrane exon and the fusion of the cytoplasmic tail and 3' untranslated sequence in a single last exon.

The MICB gene has been mapped in cloned cosmids by DNA blot hybridizations using a MICA cDNA probe. It corresponds to mRNA of about 2.4 kb, distinct from MICA mRNA, which is 1.4 kb in size (Bahram et al., 1994). A partial 2304 base pairs (bp) MICB cDNA clone lacking the leader peptide sequence was isolated from an IMR90 human lung fibroblast library by screening with the MICA cDNA probe. The missing 5' end sequence was cloned by a 5' Rapid Amplification of cDNA ends polymerase chain reaction (RACE-PCR) procedure after reverse transcription (RT) of poly(A)$^+$ HeLa cell mRNA. A cDNA including the complete MICB coding sequence was subsequently generated by RT-PCR and cloned. The full-length MICB cDNA sequence of 2380 bp encodes a polypeptide of 383 amino acids that begins with a probable translation initiation codon (ATG) at nucleotide position 6 (Bahram and Spies, 1996). The stop codon is followed by a relatively long 3' untranslated region, which accounts for the size difference of the MICB and MICA mRNAs. A consensus polyadenylation signal near the 3' end of the MICB cDNA is missing; the nearest AATAAA sequence is located 772 bp upstream and an appropriately positioned alternative polyadenylation signal is not readily discernible.

The MICB translation product is identical to the MICA chain in length and domain organization and is highly similar, with 83% matching amino acid residues. Of the total of 65 amino acid substitutions, 18 are clustered within a segment of 24 amino acids in the putative transmembrane segment of MICB, which represents the sole highly disparate portion of the aligned sequences. In the $\alpha 1$-$\alpha 3$ domains, MICB and MICA share 86% amino acid sequence similarity, with 15, 14, and 8 amino acid substitutions in the $\alpha 1$, $\alpha 2$, and $\alpha 3$ domains, respectively, which show no notable preferential distribution. Like MICA, the putative MICB chain may be heavily glycosylated, owing to the presence of five potential N-linked glycosylation sites, of which four in the $\alpha 3$ domain are common to both sequences. None of the three N-linked glycosylation motifs in MICA $\alpha 1$ and $\alpha 2$ are conserved in MICB, which has one such motif in the $\alpha 2$ domain. The highly conserved glycosylation site at amino acid position 86 in MHC class I chains is missing in MICB and MICA. Both sequences include the two pairs of cysteines in the $\alpha 2$ and $\alpha 3$ domains, which form intradomain disulfide bonds in class I chains, and several extra cysteine residues.

Common to MICB and MICA is a gap in the $\alpha 1$ domain, which corresponds to the peptide side chain-binding pocket B ("45" pocket) in many MHC class I chains, and an insertion of 6 amino acids at position 147 in the $\alpha 2$ domain (Bahram et al., 1994). Overall, MICB shows the same degree of divergence from mammalian MHC class I chains as MICA, with most of the amino acid residues that are invariant among vertebrate class I sequences being conserved (Grossberger and Parham, 1992; Bahram et al., 1994). Thus, altogether, MICB and MICA are very closely related and were probably derived by a relatively recent gene duplication.

The inventors have studied the expression of MIC polypeptides using specific antibodies, transfected mutant cell lines, and epithelial tumor cell lines. The results from these and other experiments established that, contrary to MHC class I molecules, MIC are not associated with $\beta$2-microglobulin and peptides (Groh et al., 1996; Groh et al, 1998). Both MICA and MICB are highly glycosylated; the deglycosylated polypeptides are of 43 kilodalton (kD). The crystal structure of MICA shows rearranged domain interfaces precluding binding of $\beta$2-microglobulin and the absence of a peptide binding groove (Li et al., 1999). The interaction of MICA with NKG2D homodimers has been refined by the complex crystal structure of these molecules (Li et al., 2001).

IV. PURIFICATION METHODS

Within certain embodiments of the present invention, one may wish to express and/or purify MICA, MICB, ERp5, complexes thereof, fragments thereof, antibodies thereto, related polypeptides or peptide products. Protein purification techniques are well known to those of skill in the art. These techniques tend to involve the fractionation of the cellular milieu to separate the peptides or polypeptides from other components of the mixture. Having separated peptides or polypeptides from the other plasma components, the peptide or polypeptide sample may be purified using chromatographic and electrophoretic techniques to achieve complete purification. Analytical methods particularly suited to the preparation of a pure peptide are ion-exchange chromatography, exclusion chromatography; polyacrylamide gel electrophoresis; isolectric focusing. A particularly efficient method of purifying peptides is fast protein liquid chromatography or even HPLC.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater-fold purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed elsewhere in the specification.

V. CANCER THERAPIES

Epithelial tumors are those that arise from surface or lining tissues. Epithelial cells cover surfaces and line internal passage ways. As such, epithelial tissue is found in 3 major places: outer surfaces of the body; surfaces of organs and internal surface lining of tubules, vessels and hollow organs. Most glands are composed primarily of epithelial cells. Therefore, epithelial tumors may be found on any surface or lining of the body that fits the above description. An "epithelial cancer" is one that is derived from an epithelial tissue and may occur in any location of the body, including ovarian cancer, squamous cell carcinoma, thyroid cancer, mammary neoplasia, and basal cell carcinoma As discussed above, the present inventors propose to modulate the previously unknown function of ERp5 on T cells and dendritic cells that express it. In the context of cancers, where ERp5 can down-regulate the anti-cancer immune response when bound by MICA/MICB, applicants propose interfering with the expression and/or function ERp5. The inhibitor may alter ERp5 binding to MICA/MICB, ERp5 transcription or translation or cell surface expression, ERp5 interaction with other receptors or effectors. Alternatively, the modulator may be a competing substrate for MICA/MICA, such as a MICA/MICB mimetic or an antibody that binds ERp5, an ERp5 complex, or an effector or ERp5.

In some methods of the invention, the cancer cell is a tumor cell. Furthermore, the cell may be administered compositions of the invention in vitro, in vivo, or ex vivo. Thus, the cancer cell may be in a patient. The patient may have a solid tumor. In such cases, embodiments may further involve performing surgery on the patient, such as by resecting all or part of the tumor. Viral compositions may be administered to the patient before, after, or at the same time as surgery. In additional embodiments, patients may also be administered directly, endoscopically, intratracheally, intratumorally, intravenously, intralesionally, intramuscularly, intraperitoneally, regionally, percutaneously, topically, intraarterially, intravesically, or subcutaneously. Viral compositions may be administered 1, 2, 3, 4, 5, 6, 7, 8, 9, 10, 11, 12, 13, 14, 15, 16, 17, 18, 19, 20 or more times, and they may be administered every 1, 2, 3, 4, 5, 6, 7, 8, 9, 10, 11, 12, 13, 14, 15, 16, 17, 18, 19, 20, 21, 22, 23, 24 hours, or 1, 2, 3, 4, 5, 6, 7 days, or 1, 2, 3, 4, 5 weeks, or 1, 2, 3, 4, 5, 6, 7, 8, 9, 10, 11, 12 months.

In addition, tumor cell resistance to DNA damaging agents represents a major problem in clinical oncology. One goal of current cancer research is to find ways to improve the efficacy of chemo- and radiotherapy. To kill cells, inhibit cell growth, inhibit metastasis, inhibit angiogenesis or otherwise reverse or reduce the malignant phenotype of tumor cells, using the methods and compositions of the present invention, one would generally contact a cancer cell with one of the modulators described herein and at least one other agent. These compositions would be provided in a combined amount effective to kill or inhibit proliferation of the cell. This process may involve contacting the cells with the expression construct and the agent(s) or factor(s) at the same time. This may be achieved by contacting the cell with a single composition or pharmacological formulation that includes both agents, or by contacting the cell with two distinct compositions or formulations, at the same time, wherein one composition includes one agent and the other includes the other agent.

Alternatively, one therapy may precede or follow the other by intervals ranging from minutes to weeks. In embodiments where the agents are applied separately to the cell, one would generally ensure that a significant period of time did not expire between the time of each delivery, such that the agents would still be able to exert an advantageously combined effect on the cell. In such instances, it is contemplated that one would contact the cell with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either agent will be desired. Various combinations may be employed, where the modulator described above "A" and the other cancer therapy is "B", as exemplified below:

| | | | | | | |
|---|---|---|---|---|---|---|
| A/B/A | B/A/B | B/B/A | A/A/B | B/A/A | A/B/B | B/B/B/A | B/B/A/B |
| A/A/B/B | A/B/A/B | A/B/B/A | B/B/A/A | B/A/B/A | B/A/A/B | B/B/B/A |
| A/A/A/B | B/A/A/A | A/B/A/A | A/A/B/A | A/B/B/B | B/A/B/B | B/B/A/B |

Other combinations are contemplated. Again, to achieve cell killing, both agents/treatments are delivered to a cancer cell in a combined amount effective to treat the cell.

Agents or factors suitable for use in a combined therapy are any chemical compound or treatment method that induces DNA damage when applied to a cell. Such agents and factors include radiation and waves that induce DNA damage such as, γ-irradiation, X-rays, UV-irradiation, microwaves, electronic emissions, and the like. A variety of chemical compounds, also described as "chemotherapeutic agents," function to induce DNA damage, all of which are intended to be of use in the combined treatment methods disclosed herein. Chemotherapeutic agents contemplated to be of use, include, e.g., adriamycin, 5-fluorouracil (5FU), etoposide (VP-16), camptothecin, actinomycin-D, mitomycin C, cisplatin (CDDP) and even hydrogen peroxide. The invention also encompasses the use of a combination of one or more DNA damaging agents, whether radiation-based or actual compounds, such as the use of X-rays with cisplatin or the use of cisplatin with etoposide. In certain embodiments, the use of cisplatin in combination with a Killin expression construct is particularly preferred as this compound.

In treating cancer according to the invention, one would contact the tumor cells with an agent in addition to the modulator of the present invention. This may be achieved by irradiating the localized tumor site with radiation such as X-rays, UV-light, γ-rays or even microwaves. Alternatively, the tumor cells may be contacted with the agent by administering to the subject a therapeutically effective amount of a pharmaceutical composition comprising a compound such as, adriamycin, 5-fluorouracil, etoposide, camptothecin, actinomycin-D, mitomycin C, or more preferably, cisplatin.

Agents that directly cross-link nucleic acids, specifically DNA, are envisaged to facilitate DNA damage leading to a synergistic, antineoplastic combination with Killin. Agents such as cisplatin, and other DNA alkylating agents may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25-75 mg/m$^2$ at 21 day intervals for adriamycin, to 35-50 mg/m$^2$ for etoposide intravenously or double the intravenous dose orally.

Agents that disrupt the synthesis and fidelity of nucleic acid precursors and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage DNA, on the precursors of DNA, the replication and repair of DNA, and the assembly and maintenance of chromosomes. Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The inventors propose that the local or regional delivery of modulators of the present invention to patients with cancer will be a very efficient method for treating the clinical disease. Similarly, the chemo- or radiotherapy may be directed to a particular, affected region of the subjects body. Alternatively, systemic delivery of either agent may be appropriate in certain circumstances, for example, where extensive metastasis has occurred.

In addition, it will be useful to screen for MICA/MICB-expressing cancers. This information is contained in previously published documents (PCT/US03/12299), which are hereby incorporated by reference. It is contemplated that both surface bound and soluble MIC may be detected by assaying for MIC polypeptides, including MICA (2C10 and 3H5) and MICA & MICB (6D4 and 6G6).

VI. AUTOIMMUNE DISEASE THERAPIES

In another embodiment, the inhibitory aspect of ERp5 will be stimulated to interfere with unwanted immune responses, such as in autoimmune disease and transplant rejection. An autoimmune disease or condition is characterized by an underlying defect in which there is an immune response against the body's own organs and/or tissues. By augmenting ERp5's function, it is believed that the autoimmume functions will be down-regulated, thereby lessening the attack by the host's immunity against the host's own tissues and cells.

There are believed to be at least 80 such conditions and diseases, which include, but are not limited to, the following: Alopecia Areata, Ankylosing Spondylitis, Antiphospholipid Syndrome, Autoimmune Addison's Disease, Autoimmune Hemolytic Anemia, Autoimmune Hepatitis, Behcet's Disease, Bullous Pemphigoid, Cardiomyopathy, Celiac Sprue-Dermatitis, Chronic Fatigue Immune Dysfunction Syndrome (CFIDS), Chronic Inflammatory Demyelinating Polyneuropathy, Churg-Strauss Syndrome, Cicatricial Pemphigoid, CREST Syndrome, Cold Agglutinin Disease, Crohn's Disease, Discoid Lupus, Essential Mixed Cryoglobulinemia, Fibromyalgia-Fibromyositis, Graves' Disease, Guillain-Barré, Hashimoto's Thyroiditis, Idiopathic Pulmonary Fibrosis, Idiopathic Thrombocytopenia Purpura (ITP), IgA Nephropathy, Insulin-dependent Diabetes, Juvenile Arthritis, Lichen Planus, Ménière's Disease, Mixed Connective Tissue Disease, Multiple Sclerosis, Myasthenia Gravis, Pemphigus Vulgaris, Pernicious Anemia, Polyarteritis Nodosa, Polychondritis, Polyglandular Syndromes, Polymyalgia Rheumatica, Polymyositis and Dermatomyositis, Primary Agammaglobulinemia, Primary Biliary Cirrhosis, Psoriasis, Raynaud's Phenomenon, Reiter's Syndrome, Rheumatic Fever, Rheumatoid Arthritis (RA), Sarcoidosis, Scleroderma, Sjögren's Syndrome, Stiff-Man Syndrome, Systemic Lupus Erythematosus (SLE), pediatric SLE, Takayasu Arteritis, Temporal Arteritis/Giant Cell Arteritis, Ulcerative Colitis, Uveitis, Vasculitis, Vitiligo, and Wegener's Granulomatosis. Also contemplated are transplant scenarios (bone marrow transplant, solid organ allografting), where T-cell mediated responses give rise to, e.g., graft-versus-host disease. Methods and compositions of the invention are specifically contemplated for use with respect to RA.

The modulator may mimic the signaling of MICA/MICB through ERp5, such as by providing a mimetic of MICA/MICB or an antibody to ERp5. Another mode of therapy is to increase ERp5 expression or signaling, for example, by providing a drug having such effects. The treatment may involve multiple rounds of the therapeutic agent. For example, following an initial round of administration, an additional round of administration can be performed. In this way, multiple rounds of administration can be performed until the disorder is adequately treated.

Combination therapies with additional agents also are contemplated. Corticosteroid drugs, analgesics, non-steroidal anti-inflammatory drugs (NSAIDs) or more powerful immunosuppressant drugs such as cyclophosphamide, methotrexate and azathioprine that suppress the immune response and stop the progression of autoimmune diseases. Radiation of the lymph nodes and plasmapheresis (a procedure that removes the diseased cells and harmful molecules from the blood circulation) are sometimes employed.

In addition, it will be useful to screen for MICA/MICB-expressing cells in autoimmune patients. This information is contained in previously published documents (PCT/US03/12299), which are hereby incorporated by reference. It is contemplated that both surface bound and soluble MIC may be detected by assaying for MIC polypeptides, including MICA (2C10 and 3H5) and MICA & MICB (6D4 and 6G6).

A. Inflammatory Diseases

The present invention also permits the treatment of various inflammatory diseases, where the inflammation is mediated by dendritic and or T cells that express ERp5, and that can be inhibited in a fashion analogous to that discussed above with respect to autoimmune disease. Some of these disease states are discussed below.

Psoratic Arthritis. Psoriasis is an inflammatory and proliferative skin disorder with a prevalence of 1.5-3%. Approximately 20% of patients with psoriasis develop a characteristic form of arthritis that has several patterns (Gladman, 1992; Moll & Wright, 1973; Jones et al., 1994; Gladman et al., 1995). Some individuals present with joint symptoms first but in the majority, skin psoriasis presents first. About one-third of patients have simultaneous exacerbations of their skin and joint disease (Gladman et al., 1987) and there is a topographic relationship between nail and distal interphalangeal joint disease (Jones et al., 1994; Wright, 1956). Although the inflammatory processes which link skin, nail and joint disease remain elusive, an immune-mediated pathology is implicated.

Psoriatic arthritis (PsA) is a chronic inflammatory arthropathy characterized by the association of arthritis and psoriasis and was recognized as a clinical entity distinct from rheumatoid arthritis (RA) in 1964 (Blumberg et al., 1964). Subsequent studies have revealed that PsA shares a number of genetic, pathogenic and clinical features with other spondyloarthropathies (SpAs), a group of diseases that comprise ankylosing spondylitis, reactive arthritis and enteropathic arthritis (Wright, 1979). The notion that PsA belongs to the SpA group has recently gained further support from imaging studies demonstrating widespread enthesitis in the, including PsA but not RA (McGonagle et al., 1999; McGonagle et al., 1998). More specifically, enthesitis has been postulated to be one of the earliest events occurring in the SpAs, leading to bone remodeling and ankylosis in the spine, as well as to articular synovitis when the inflamed entheses are close to peripheral joints. However, the link between enthesitis and the clinical manifestations in PsA remains largely unclear, as PsA can present with fairly heterogeneous patterns of joint involvement with variable degrees of severity (Marsal et al., 1999; Salvarani et al., 1998). Thus, other factors must be posited to account for the multifarious features of PsA, only a few of which (such as the expression of the HLA-B27 molecule, which is strongly associated with axial disease) have been identified. As a consequence, it remains difficult to map the disease manifestations to specific pathogenic mechanisms, which means that the treatment of this condition remains largely empirical.

Family studies have suggested a genetic contribution to the development of PsA (Moll & Wright, 1973). Other chronic inflammatory forms of arthritis, such as ankylosing spondylitis and rheumatoid arthritis, are thought to have a complex genetic basis. However, the genetic component of PsA has been difficult to assess for several reasons. There is strong evidence for a genetic predisposition to psoriasis alone that may mask the genetic factors that are important for the development of PsA. Although most would accept PsA as a distinct disease entity, at times there is a phenotypic overlap with rheumatoid arthritis and ankylosing spondylitis. Also, PsA itself is not a homogeneous condition and various subgroups have been proposed. Although not all these confounding factors were overcome in the present study, the inventors concentrated on investigating candidate genes in three broad categories of patients with PsA that cover the disease spectrum.

Polymorphisms in the promoter region of the TNFA region are of considerable interest as they may influence levels of TNF-α secretion (Jacob et al., 1990; Bendzen et al., 1988). Increased amounts of TNF-α have been reported in both psoriatic skin (Ettehadi et al., 1994) and synovial fluid (Partsch et al., 1997).

Recent trials have shown a positive benefit of anti-TNF treatment in both PsA (Mease et al., 2000) and ankylosing spondylitis (Brandt et al., 2000). Furthermore, the locus for TNF-α resides within the class III region of the MHC and thus may provide tighter associations with PsA than those provided by flanking class I and class II regions. There were relatively weak associations with the TNFA alleles in our total PsA group. The uncommon TNFA-238A allele was increased in frequency in the group with peripheral polyarthritis and absent in those patients with spondylitis, although this finding may be explained by linkage disequilibrium with HLA-Cw*0602. Whether there are functional consequences associated with polymorphisms at the TNFA-238 allele is unclear (Pociot et al., 1995). Nonetheless, it is possible that the pattern of arthritis that develops in patients with psoriasis may be linked directly or indirectly to this particular allele.

Hohler et al. (1997) found an increase in the frequency of the TNFA-238A allele in patients with PsA as well as in juvenile onset psoriasis. The association of TNFA-238A with both juvenile onset psoriasis and PsA was stronger than that with HLA-Cw6. Similarly, there were strong associations between juvenile onset psoriasis and both HLA-Cw*0602 and TNFA-238A, although neither allele had any relationship to the age of onset of arthritis. All patients with PsA who had at least one TNFA-238A allele were HLA-Cw6-positive, emphasizing the close linkage between these alleles in PsA. However, in contrast to the study by Hohler et al. (1997), and explainable by close linkage to HLA-Cw*0602, the TNFA-238A allele was only increased in patients with peripheral arthritis. It is also of interest that, in a separate study of ankylosing spondylitis, the same group found the uncommon TNFA-308A and -238A alleles to have a protective effect on the development of spondylitis (Hohler et al., 1998).

Reactive Arthritis. In reactive arthritis (ReA) the mechanism of joint damage is unclear, but it is likely that cytokines play critical roles. A more prevalent Th1 profile high levels of interferon gamma (IFN-γ) and low levels of interleukin 4 (IL-4) has been reported (Lahesmaa et al., 1992; Schlaak et al., 1992; Simon et al., 1993; Schlaak et al., 1996; Kotake et al., 1999; Ribbens et al., 2000), but several studies have shown relative predominance of IL-4 and IL-10 and relative lack of IFN-γ and tumor necrosis factor alpha (TNF-α) in the synovial membrane (Simon et al., 1994; Yin et al., 1999) and fluid (SF) (Yin et al., 1999; Yin et al., 1997) of reactive arthritis patients compared with rheumatoid arthritis (RA) patients. A lower level of TNF-α secretion in reactive arthritis than in RA patients has also been reported after ex vivo stimulation of peripheral blood mononuclear cells (PBMC) (Braun et al., 1999).

It has been argued that clearance of reactive arthritis-associated bacteria requires the production of appropriate levels of IFN-γ and TNF-α, while IL-10 acts by suppressing these responses (Autenrieth et al., 1994; Sieper & Braun, 1995). IL-10 is a regulatory cytokine that inhibits the synthesis of IL-12 and TNF-γ by activated macrophages (de Waal et al., 1991; Hart et al., 1995; Chomarat et al., 1995) and of IFN-γ by T cells (Macatonia et al., 1993).

Enteropathic Arthritis. Enteropathic arthritis (EA) occurs in combination with inflammatory bowel diseases (IBD) such as Crohn's disease or ulcerative colitis. It also can affect the spine and sacroiliac joints. Enteropathic arthritis involves the peripheral joints, usually in the lower extremities such as the knees or ankles. It commonly involves only a few or a limited number of joints and may closely follow the bowel condition. This occurs in approximately 11% of patients with ulcerative colitis and 21% of those with Crohn's disease. The synovitis is generally self-limited and non-deforming.

Enteropathic arthropathies comprise a collection of rheumatologic conditions that share a link to GI pathology. These conditions include reactive (i.e., infection-related) arthritis due to bacteria (e.g., *Shigella, Salmonella, Campylobacter, Yersinia* species, *Clostridium difficile*), parasites (e.g., *Strongyloides stercoralis, Taenia saginata, Giardia lamblia, Ascaris lumbricoides, Cryptosporidium* species), and spondyloarthropathies associated with inflammatory bowel disease (IBD). Other conditions and disorders include intestinal bypass (jejunoileal), arthritis, celiac disease, Whipple disease, and collagenous colitis.

The precise causes of enteropathic arthropathies are unknown. Inflammation of the GI tract may increase permeability, resulting in absorption of antigenic material, including bacterial antigens. These arthrogenic antigens may then localize in musculoskeletal tissues (including entheses and synovium), thus eliciting an inflammatory response. Alternatively, an autoimmune response may be induced through molecular mimicry, in which the host's immune response to these antigens cross-reacts with self-antigens in synovium.

Of particular interest is the strong association between reactive arthritis and HLA-B27, an HLA class I molecule. A potentially arthrogenic, bacterially derived antigen peptide could fit in the antigen-presenting groove of the B27 molecule, resulting in a CD8+ T-cell response. HLA-B27 transgenic rats develop features of enteropathic arthropathy with arthritis and gut inflammation.

Familial Mediterranean Fever. Familial Mediterranean Fever is an inherited disorder usually characterized by recurrent episodes of fever and peritonitis (inflammation of the abdominal membrane). In 1997, researchers identified the gene for FMF and found several different gene mutations that cause this inherited rheumatic disease. The gene, found on chromosome 16, codes for a protein that is found almost exclusively in granulocytes—white blood cells important in the immune response. The protein is likely to normally assist in keeping inflammation under control by deactivating the immune response—without this 'brake,' an inappropriate full-blown inflammatory reaction occurs: an attack of FMF. To explore whether a molecular diagnostic cytokine characteristic exists, serum samples from six patients with clinically diagnosed FMF were examined and the concentration of cytokines were quantified.

Irritable Bowel Syndrome. Irritable bowel syndrome (IBS) is a functional disorder characterized by abdominal pain and altered bowel habits. This syndrome may begin in young adulthood and can be associated with significant disability. This syndrome is not a homogeneous disorder. Rather, subtypes of IBS have been described on the basis of the predominant symptom—diarrhea, constipation, or pain. In the absence of "alarm" symptoms, such as fever, weight loss, and gastrointestinal bleeding, a limited workup is needed. Once a diagnosis of IBS is made, an integrated treatment approach can effectively reduce the severity of symptoms. IBS is a common disorder, although its prevalence rates have varied. In general, IBS affects about 15% of US adults and occurs about three times more often in women than in men (Jailwala et al., 2000).

IBS accounts for between 2.4 million and 3.5 million visits to physicians each year. It not only is the most common condition seen by gastroenterologists but also is one of the most common gastrointestinal conditions seen by primary care physicians (Everhart et al., 1991; Sandler, 1990).

IBS is also a costly disorder. Compared with persons who do not have bowel symptoms, persons with IBS miss three times as many workdays and are more likely to report being too sick to work (Drossman et al., 1993; Drossman et al., 1997). Moreover, those with IBS incur hundreds of dollars more in medical charges than persons without bowel disorders (Talley et al., 1995).

No specific abnormality accounts for the exacerbations and remissions of abdominal pain and altered bowel habits experienced by patients with IBS. The evolving theory of IBS suggests dysregulation at multiple levels of the brain-gut axis. Dysmotility, visceral hypersensitivity, abnormal modulation of the central nervous system (CNS), and infection have all been implicated. In addition, psychosocial factors play an important modifying role. Abnormal intestinal motility has long been considered a factor in the pathogenesis of IBS. Transit time through the small intestine after a meal has been shown to be shorter in patients with diarrhea-predominant IBS than in patients who have the constipation-predominant or pain-predominant subtype (Cann et al., 1983).

In studies of the small intestine during fasting, the presence of both discrete, clustered contractions and prolonged, propagated contractions has been reported in patients with IBS (Kellow & Phillips, 1987). They also experience pain with irregular contractions more often than healthy persons (Kellow & Phillips, 1987; Horwitz & Fisher, 2001)

These motility findings do not account for the entire symptom complex in patients with IBS; in fact, most of these patients do not have demonstrable abnormalities (Rothstein, 2000). Patients with IBS have increased sensitivity to visceral pain. Studies involving balloon distention of the rectosigmoid colon have shown that patients with IBS experience pain and bloating at pressures and volumes much lower than control subjects (Whitehead et al., 1990). These patients maintain normal perception of somatic stimuli.

Multiple theories have been proposed to explain this phenomenon. For example, receptors in the viscera may have increased sensitivity in response to distention or intraluminal contents. Neurons in the dorsal horn of the spinal cord may have increased excitability. In addition, alteration in CNS processing of sensations may be involved (Drossman et al., 1997). Functional magnetic resonance imaging studies have recently shown that compared with control subjects, patients with IBS have increased activation of the anterior cingulate cortex, an important pain center, in response to a painful rectal stimulus (Mertz et al., 2000).

Increasingly, evidence suggests a relationship between infectious enteritis and subsequent development of IBS. Inflammatory cytokines may play a role. In a survey of patients with a history of confirmed bacterial gastroenteritis (Neal et al., 1997), 25% reported persistent alteration of bowel habits. Persistence of symptoms may be due to psychologic stress at the time of acute infection (Gwee et al., 1999).

Recent data suggest that bacterial overgrowth in the small intestine may have a role in IBS symptoms. In one study (Pimentel et al., 2000), 157 (78%) of 202 IBS patients referred for hydrogen breath testing had test findings that were positive for bacterial overgrowth. Of the 47 subjects who had follow-up testing, 25 (53%) reported improvement in symptoms (i.e., abdominal pain and diarrhea) with antibiotic treatment.

IBS may present with a range of symptoms. However, abdominal pain and altered bowel habits remain the primary features. Abdominal discomfort is often described as crampy in nature and located in the left lower quadrant, although the severity and location can differ greatly. Patients may report diarrhea, constipation, or alternating episodes of diarrhea and constipation. Diarrheal symptoms are typically described as small-volume, loose stools, and stool is sometimes accompanied by mucus discharge. Patients also may report bloating, fecal urgency, incomplete evacuation, and abdominal distention. Upper gastrointestinal symptoms, such as gastroesophageal reflux, dyspepsia, or nausea, may also be present (Lynn & Friedman, 1993).

Persistence of symptoms is not an indication for further testing; it is a characteristic of IBS and is itself an expected symptom of the syndrome. More extensive diagnostic evaluation is indicated in patients whose symptoms are worsening or changing. Indications for further testing also include presence of alarm symptoms, onset of symptoms after age 50, and a family history of colon cancer. Tests may include colonoscopy, computed tomography of the abdomen and pelvis, and barium studies of the small or large intestine.

Early Arthritis. The clinical presentation of different inflammatory arthropathies is similar early in the course of disease. As a result, it is often difficult to distinguish patients who are at risk of developing the severe and persistent synovitis that leads to erosive joint damage from those whose arthritis is more self-limited. Such distinction is critical in order to target therapy appropriately, treating aggressively those with erosive disease and avoiding unnecessary toxicity in patients with more self-limited disease. Current clinical criteria for diagnosing erosive arthropathies such as rheumatoid arthritis (RA) are less effective in early disease and traditional markers of disease activity such as joint counts and acute phase response do not adequately identify patients likely to have poor outcomes (Harrison & Symmons et al., 1998). Parameters reflective of the pathologic events occurring in the synovium are most likely to be of significant prognostic value.

Recent efforts to identify predictors of poor outcome in early inflammatory arthritis have identified the presence of RA specific autoantibodies, in particular antibodies towards citrullinated peptides, to be associated with erosive and persistent disease in early inflammatory arthritis cohorts. On the basis of this, a cyclical citrullinated peptide (CCP) has been developed to assist in the identification of anti-CCP antibodies in patient sera. Using this approach, the presence of anti-CCP antibodies has been shown to be specific and sensitive for RA, can distinguish RA from other arthropathies, and can potentially predict persistent, erosive synovitis before these outcomes become clinically manifest (Schellekens et al., 2000). Importantly, anti-CCP antibodies are often detectable in sera many years prior to clinical symptoms suggesting that they may be reflective of subclinical immune events ((Nielen et al., 2004; Rantapaa-Dahlqvist et al., 2003).

The clinical presentation of different inflammatory arthropathies is similar early in the course of disease. As a result, it is often difficult to distinguish patients who are at risk of developing the severe and persistent synovitis that leads to erosive joint damage from those whose arthritis is more self-limited. Such distinction is critical in order to target therapy appropriately, treating aggressively those with erosive disease and avoiding unnecessary toxicity in patients with more self-limited disease. Current clinical criteria for diagnosing erosive arthropathies such as rheumatoid arthritis (RA) are less effective in early disease and traditional markers of disease activity such as joint counts and acute phase response do not adequately identify patients likely to have poor outcomes (Harrison et al., 1998). Parameters reflective of the pathologic events occurring in the synovium are most likely to be of significant prognostic value.

Recent efforts to identify predictors of poor outcome in early inflammatory arthritis have identified the presence of RA specific autoantibodies, in particular antibodies towards citrullinated peptides, to be associated with erosive and persistent disease in early inflammatory arthritis cohorts. On the basis of this, a cyclical citrullinated peptide (CCP) has been developed to assist in the identification of anti-CCP antibodies in patient sera. Using this approach, the presence of anti-CCP antibodies has been shown to be specific and sensitive for RA, can distinguish RA from other arthropathies, and can potentially predict persistent, erosive synovitis before these outcomes become clinically manifest. Importantly, anti-CCP antibodies are often detectable in sera many years prior to clinical symptoms suggesting that they may be reflective of subclinical immune events (Nielen et al., 2004; Rantapaa-Dahlqvist et al., 2003).

Neuroinflammation. Neuroinflammation encapsulates the idea that microglial and astrocytic responses and actions in the central nervous system have a fundamentally inflammation-like character, and that these responses are central to the pathogenesis and progression of a wide variety of neurological disorders. This idea originated in the field of Alzheimer's disease (Griffin et al., 1989; Rogers et al., 1988), where it has revolutionized our understanding of this disease (Akiyama et al., 2000). These ideas have been extended to other neurodegenerative diseases (Eikelenboom et al., 2002; Orr et al., 2002; Ishizawa & Dickson, 2001), to ischemic/toxic diseases (Gehrmann et al., 1995; Touzani et al., 1999), to tumor biology (Graeber et al., 2002) and even to normal brain development.

Neuroinflammation incorporates a wide spectrum of complex cellular responses that include activation of microglia and astrocytes and induction of cytokines, chemokines, complement proteins, acute phase proteins, oxidative injury, and related molecular processes. These events may have detrimental effects on neuronal function, leading to neuronal injury, further glial activation, and ultimately neurodegeneration.

Neuroinflammation is a new and rapidly expanding field that has revolutionized our understanding of chronic neurological diseases. This field encompasses research ranging from population studies to signal transduction pathways, and investigators with backgrounds in fields as diverse as pathology, biochemistry, molecular biology, genetics, clinical medicine, and epidemiology. Important contributions to this field have come from work with populations, with patients, with postmortem tissues, with animal models, and with in vitro systems.

B. Infections

A variety of infectious agents can induce immune responses in a subject. Many times, the immune response is helpful to protect the host and clear the diseases. In a smaller percentage, the immune response may itself be more dangerous than the infection. In both contexts, the agonists and antagonists of the present invention may be used to modulate the immune response to advantage. For example, in an infection where the immune system needs to be augmented, one would employ the ERp5 antagonists described above to down-regulate the immunosuppressive functions of ERp5, optionally including a second therapy targeting the infectious agent. Administration of such a "double-agent" therapy would follow the general outline provided above for double-agent anti-cancer therapy. In contrast, where the immune response to an infectious agent actually becomes destructive to the host, the immunosuppressive function of ERp5 may be intentionally induced or augmented to protect the host, and optionally a second agent, such as an antibiotic, anti-viral, anti-parasitic or anti-fungal agent may be used to directly attack the infectious agent. Again, administration of such a "double-agent" therapy would follow the general outline provided above for double-agent anti-cancer therapy.

Fungal Diseases. There is reason to believe that compounds from ethnobotanical sources will be useful for the treatment of fungal infections; for example, extracts from certain Hawaiian medicinal plants have inhibited the growth of fungi in vitro (Locher et al., 1995). Fungal diseases are caused by fungal and other mycotic pathogens (some of which are described in Human Mycoses (Beneke, 1979); Opportunistic Mycoses of Man and Other Animals (Smith, 1989); and Scripp's Antifungal Report, 1992); fungal diseases range from mycoses involving skin, hair, or mucous membranes, such as, but not limited to, Aspergillosis, Black piedra, Candidiasis, Chromomycosis, Cryptococcosis, Onychomycosis, or Otitis externa (otomycosis), Phaeohyphomycosis, Phycomycosis, Pityriasis versicolor, ringworm, Tinea barbae, Tinea capitis, Tinea corporis, Tinea cruris, Tinea favosa, Tinea imbricata, Tinea manuum, Tinea nigra (palmaris), Tinea pedis, Tinea unguium, Torulopsosis, Trichomycosis axillaris, White piedra, and their synonyms, to severe systemic or opportunistic infections, such as, but not limited to, Actinomycosis, Aspergillosis, Candidiasis, Chromomycosis, Coccidioidomycosis, Cryptococcosis, Entomophthoramycosis, Geotrichosis, Histoplasmosis, Mucormycosis, Mycetoma, Nocardiosis, North American Blastomycosis, Paracoccidioidomycosis, Phaeohyphomycosis, Phycomycosis, pneumocystic pneumonia, Pythiosis, Sporotrichosis, and Torulopsosis, and their synonyms, some of which may be fatal.

Known fungal and mycotic pathogens include, but are not limited to, *Absidia* spp., *Actinomadura madurae*, *Actinomyces* spp., *Alleschería boydii*, *Alternaria* spp., *Anthopsis deltoidea*, *Apophysomyces elegans*, *Amium leoporinum*, *Aspergillus* spp., *Aureobasidium pullulans*, *Basidiobolus ranarum*, *Bipolaris* spp., *Blastomyces dermatitidis*, *Candida* spp., *Cephalosporium* spp., *Chaetoconidium* spp., *Chaetomium* spp., *Cladosporium* spp., *Coccidioides immitis*, *Conidiobolus* spp., *Corynebacterium tenuis*, *Cryptococcus* spp., *Cunninghamella bertholletiae*, *Curvularia* spp., *Dactylaria* spp., *Epidermophyton* spp., *Epidermophyton floccosum*, *Exserophilum* spp., *Exophiala* spp., *Fonsecaea* spp., *Fusarium* spp., *Geotrichum* spp., *Helminthosporium* spp., *Histoplasma* spp., *Lecythophora* spp., *Madurella* spp., *Malassezia furfur*, *Microsporum* spp., *Mucor* spp., *Mycocentrospora acerina*, *Nocardia* spp., *Paracoccidioides brasiliensis*, *Penicillium* spp., *Phaeosclera dematioides*, *Phaeoannellomyces* spp., *Phialemonium obovatum*, *Phialophora* spp., *Phoma* spp., *Piedraia hortai*, *Pneumocystis carinii*, *Pythium insidiosum*, *Rhinocladiella aquaspersa*, *Rhizomucor pusillus*, *Rhizopus* spp., *Saksenaea vasiformis*, *Sarcinomyces phaeomuriformis*, *Sporothrix schenckii*, *Syncephalastrum racemosum*, *Taeniolella boppii*, *Torulopsosis* spp., *Trichophyton* spp., *Trichosporon* spp., *Ulocladium chartarum*, *Wangiella dermatitidis*, *Xylohypha* spp., *Zygomyetes* spp. and their synonyms. Other fungi that have pathogenic potential include, but are not limited to, *Thermomucor indicae-seudaticae*, *Radiomyces* spp., and other species of known pathogenic genera. These fungal organisms are ubiquitous in air, soil, food, decaying food, etc. Histoplasmoses, *Blastomyces*, and *Coccidioides*, for example, cause lower respiratory infections. *Trichophyton rubrum* causes difficult to eradicate nail infections. In some of the patients suffering with these diseases, the infection can become systemic causing fungal septicemia, or brain/meningeal infection, leading to seizures and even death.

Viral Diseases. Viral diseases include, but are not limited to influenza A, B and C, parainfluenza (including types 1, 2, 3, and 4), paramyxoviruses, Newcastle disease virus, measles, mumps, adenoviruses, adenoassociated viruses, parvoviruses, Epstein-Barr virus, rhinoviruses, coxsackieviruses, echoviruses, reoviruses, rhabdoviruses, lymphocytic choriomeningitis, noroviruses, coronavirus, polioviruses, herpes simplex, human immunodeficiency viruses, cytomegaloviruses, papillomaviruses, virus B, varicella-zoster, poxviruses, rubella, rabies, picornaviruses, rotavirus, Kaposi associated herpes virus, herpes viruses type 1 and 2, hepatitis (including types A, B, and C), and respiratory syncytial virus (including types A and B).

Bacterial Diseases. Bacterial diseases include, but are not limited to, infection by the 83 or more distinct serotypes of pneumococci, streptococci such as *S. pyogenes, S. agalactiae, S. equi, S. canis, S. bovis, S equinus, S. anginosus, S. sanguis, S. salivarius, S mitis, S. mutans*, other viridans streptococci, peptostreptococci, other related species of streptococci, enterococci such as *Enterococcus faecalis, Enterococcus faecium*, Staphylococci, such as *Staphylococcus epidermidis, Staphylococcus aureus*, particularly in the nasopharynx, *Hemophilus influenzae*, pseudomonas species such as *Pseudomonas aeruginosa, Pseudomonas pseudomallei, Pseudomonas mallei*, brucellas such as *Brucella melitensis, Brucella suis, Brucella abortus, Bordetella pertussis, Neisseria meningitidis, Neisseria gonorrhoeae, Moraxella catarrhalis, Corynebacterium diphtheriae, Corynebacterium ulcerans, Corynebacterium pseudotuberculosis, Corynebacterium pseudodiphtheriticum, Corynebacterium urealyticum, Corynebacterium hemolyticum, Corynebacterium equi*, etc. *Listeria monocytogenes, Nocordia asteroides, Bacteroides* species, *Actinomycetes* species, *Treponema pallidum, Leptospirosa* species and related organisms. The invention may also be useful against gram negative bacteria such as *Klebsiella pneumoniae, Escherichia coli, Proteus, Serratia* species, *Acinetobacter, Yersinia pestis, Francisella tularensis, Enterobacter* species, *Bacteriodes* and *Legionella* species and the like.

Protozoan Diseases. Protozoan or macroscopic diseases include infection by organisms such as *Cryptosporidium, Isospora belli, Toxoplasma gondii, Trichomonas vaginalis, Cyclospora* species, for example, and for *Chlamydia trachomatis* and other *Chlamydia* infections such as *Chlamydia psittaci*, or *Chlamydia pneumoniae*, for example.

VII. PHARMACEUTICALS

Pharmaceutically acceptable carriers that may be used with the agonist and antagonist compounds described above include compositions comprising, but not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. For localized disorders such as RA, the compositions will often be administered topically, e.g., in inflamed joints.

Sterile injectable forms of the compositions of this invention may be aqueous or an oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols. Such compositions are prepared according to techniques well-known in the art of pharmaceutical formulation.

The compositions of this invention may be administered topically, especially when the target of treatment includes areas or organs readily accessible by topical application, including diseases of the eye, the skin, the joints, or the lower intestinal tract. Suitable topical formulations are readily prepared for each of these areas or organs. Topical application for the lower intestinal tract can be effected in a rectal suppository formulation (see above) or in a suitable enema formulation. Topically-transdermal patches may also be used.

For topical applications, the compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the compositions may be formulated in an ointment such as petrolatum.

The compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In one embodiment, the antibodies or therapeutic compounds of this invention may be incorporated into liposomes ("immunoliposomes" in the case of antibodies), alone or together with another substance for targeted delivery to a patient or an animal. Such other substances can include nucleic acids for the delivery of genes for gene therapy or for the delivery of antisense RNA, RNAi or siRNA for suppressing a gene in a T cell, or toxins or drugs for the activation of T cells through other means, or any other agent described herein that may be useful for activation of T cells.

In particular, applicants contemplate the use of lipid transport technologies described in U.S. Patent Publications 2001/0007666 and 2005/0136102, the contents of which are hereby incorporated by reference. Those documents disclose compositions and methods for transport or release of therapeutic and diagnostic agents or metabolites or other analytes from cells, compartments within cells, or through cell layers or barriers are described. The compositions include a membrane barrier transport enhancing agent and are usually administered in combination with an enhancer and/or exposure to stimuli to effect disruption or altered permeability, transport or release. In a particular embodiment, the compositions include compounds which disrupt endosomal membranes in response to the low pH in the endosomes but which are relatively inactive toward cell membranes, coupled directly or indirectly to a therapeutic or diagnostic agent. Other disruptive agents can also be used, responsive to stimuli and/or enhancers other than pH, such as light, electrical stimuli, electromagnetic stimuli, ultrasound, temperature, or combinations thereof. The compounds can be coupled by ionic, covalent or H bonds to an agent to be delivered or to a ligand which forms a complex with the agent to be delivered. Agents to be delivered can be therapeutic and/or diagnostic agents. Treatments which enhance delivery such as ultrasound, iontophoresis, and/or electrophereis can also be used with the disrupting agents.

In another embodiment, the antibodies or other compounds of the invention can be modified to improve its bioavailability, half-life in vivo, etc. For example, antibodies and other compounds can be pegylated, using any of the number of forms of polyethylene glycol and methods of attachment known in the art (see, e.g., Lee et al., 2003; Harris et al., 2003; Deckert et al., 2000).

For non-antibody compounds, the dose administered to a patient should be sufficient to effect a beneficial response in the subject over time. The dose will be determined by the efficacy of the particular modulators employed and the condition of the subject, as well as the body weight or surface area of the area to be treated. The size of the dose also will be determined by the existence, nature, and extent of any adverse side-effects that accompany the administration of a particular compound or vector in a particular subject. In determining the effective amount of the compound to be administered, a physician may evaluate circulating plasma levels of the compound, compound toxicities, and the production of anti-compound antibodies. In general, the dose equivalent of a compound is from about 1 ng/kg to 10 mg/kg for a typical subject. Administration can be accomplished via single or divided doses.

According to another important embodiment of the present invention, the primary compounds may be administered in conjunction with one or more additional therapeutic agents, including agents normally utilized for the particular therapeutic purpose for which the antibody or compound is being administered, e.g. for treatment of autoimmune disease (anti-inflammatories, immunosuppressive agents) or cancer (chemotherapy, radiation, surgery, hormonal therapy). The other agents can either be administered together with the present antibody or compound, i.e., in the same pharmaceutical composition, or may be administered separately, including temporally. The additional therapeutic agent will generally be administered at a dose typically used for that agent in a monotherapy for the particular disease or condition being treated.

Further aspects and advantages of this invention are disclosed in the following experimental section, which should be regarded as illustrative and not limiting the scope of this application.

VIII. EXAMPLES

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

NKG2D-Dependent Immunosuppression and Mechanism of MICA Shedding

Epithelial tumor shedding of soluble MIC ligands causes NKG2D receptor endocytosis and degradation and thus systemic downmodulation on NK cells and CD8 T cells. As a consequence, NK and T cell responsiveness is impaired. Most CD4$^+$ T cells are normally negative for NKG2D. In cancer patients with tumor-associated MIC, however, variable proportions of CD4+ T cells, ranging from about 8 up to 77% (mean 25% among 28 individuals) express low to very high levels of NKG2D. In vitro activation results in a rapid induction of NKG2D on about 8 to 12% of normal CD4 T cells, which proliferate in the additional presence of solid-phase anti-NKG2D mAb or soluble MICA providing costimulation. Over an extended culture period, these T cells expand substantially, and cause growth arrest of NKG2D⁻ CD4⁺ T cells by secretion of soluble mediators. These preliminary results reveal an additional immunosuppressive effect of MIC-NKG2D in tumor settings.

The shedding of soluble MIC is thought to be mediated by metalloproteinases. However, recent evidence has unraveled more complex molecular events. On the surface of tumor cell lines and freshly isolated tumor cells, MICA specifically associates with ERp5, an endoplasmic reticulum protein of the protein disulphide isomerase (PDI) family. Pharmacological inhibition of thioreductase catalytic activities and siRNA-mediated silencing of ERp5 expression profoundly reduced shedding of soluble MICA and interfered with its physical interaction with ERp5. Reduction of an intradomain disulphide bond of MICA causes a conformational destabilization that is a necessary prerequisite for proteolytic cleavage within the peptide sequence that connects the proximal α3 and transmembrane domains.

Example 2

Disulfide Isomerase-Enabled Shedding Of Tumor-Associated NKG2D Ligands

A. Materials & Methods

Tumor samples and cell lines, antibodies, tetramers, pharmacological inhibitors, and ELISA for sMICA. The source of tumor cell suspensions has been reported[7]. Cell lines were from the American Type Culture Collection. Anti-NKG2D (mAb 1D11) and anti-MICA (mAb 2C10) have been described (Bauer et al., 1999; Groh et al., 1996). Rabbit polyclonal anti-ERp5 and -GRP78 were from Affinity BioReagents and Stressgen, respectively. Recombinant MICA*001 (residues 1-276) and ULBP2 (residues 1-202) were produced in transfected 293T cells and purified from culture supernatant using Invitrogen methodology. Tetramers were prepared by BirA enzymatic biotinylation and conjugation with phycoerythrin (PE)-streptavidin. Cells were stained with saturating tetramer concentrations for 1 h at 4° C. and examined by flow cytometry. Non-glycosylated MICA was expressed in bacteria and purified as described$_{22}$. Cells were exposed to DTNB or PAO (Sigma) for 24 h at the indicated concentrations. For inhibition of tetramer binding, cells were grown for 24 h in the presence of 0.5 μM PAO. Metalloproteinase inhibitors GM 6001 and MMP Inhibitor III were from Calbiochem. The ELISA for sMICA has been described (Groh et al., 2002).

Identification of MICA binding surface proteins. U266 and U937 cells (each 5×10⁹) were dounce-homogenized in 10 mM Tris-HCl (pH7.6), 0.5 mM MgCl$_2$, 1 mM PMSF, 1 μg/ml leupeptin, and 1 μg/ml pepstatin. Membrane fractions were isolated from cleared supernatants by dextran-PEG partitioning, washed [8% sucrose, 5 mM Tris-HCl (pH 7.4)], and dissociated in lysis buffer [50 mM Tris-Cl (pH 7.4), 1% Triton X-114, 150 mM NaCl, 5 mM EDTA, 5 mM iodoacetamide, protease inhibitors]. Cleared supernatants were warmed to 37° C. and proteins partitioned during Triton X-114 phase separation. Proteins in aqueous fractions were affinity-purified using MICA conjugated to cyanogen bromide-activated sepharose beads, visualized by SDS-PAGE and silver staining, and analysed by MALDI-TOF at the FHCRC Mass Spectrometry Facility. For immunoblotting, MICA-binding proteins were prepared after cell surface biotinylation with EZ-Link Sulfo-NHS-LC-Biotin (Pierce).

Immunoprecipitations and sMICA cleavage. Denatured and reduced RNase A (dRNase) was prepared as described. Hela cells were exposed to dRNase for 16 h, washed and surface biotinylated, incubated in 10% (w/v) TCA in PBS for 30 min on ice, washed, and lysed with immediate pH neutralization in standard NP-40 lysis buffer containing protease inhibitors and N-ethylmaleimide. Immunoprecipitated protein complexes were treated with N-glycanase and subjected to SDS-PAGE and membrane transfer. C-terminal truncation analysis of sMICA was performed by mass Spectrometry at the Harvard University Microchemistry Facility.

siRNA expression and real-time RT-PCR. Oligonucleotide pairs for siRNA-17 and siRNA-19 targeting ERp5 (disulfide isomerase-related protein P5; GenBank accession number D49489) mRNA at positions 316-338 and 556-567 were GATCTTGTTGTCAAAGTTGGTGCAGT-TGTCTTCTTCTCAACTGCACCAACTTTGACAA CATTTTTG (SEQ ID NO:5) and AATTCAAAAATGTTGT-CAAAGTTGGTGCAGTTGAGAAGAAGA-CAACTGCACCAACT TTGACAACAA (SEQ ID NO:6), and GATCTTGATAGTTCAAGTAAGAAG GATGTCT-TCTTCTCATCCTTCTTACTTGAACTATCATTTTTG (SEQ ID NO:7) and AATTCAAAAATGATAGTTCAAG-TAAGAAGGATGAGAAGAAGACATCCTTCTTACTT GAACTATAA (SEQ ID NO:8) respectively (all 5'-3'; internal hairpin sequence, 3'-end termination signal, and Bgl II and Eco RI overhangs are underlined). An irrelevant oligonucleotide pair with no homology to any human gene was GATCT-TATGTCAAGTTGTATAGTTATTCAA-GAGATAACTATACAACTTGACATATTTT TG (SEQ ID NO:19) and AATTCAAAAATATGTCAAGTTGTATAGT-TATCTCTTGAATAACTATACAACTTGACA TAA (SEQ ID NO:20). Annealed primers were ligated into retroviral vector pBABEGFP and constructs sequenced. Virus was produced in Phoenix amphotropic packaging cells and culture supernatant used for infection of A375 cells, which were sorted for GFP expression. Real-time RT-PCR was performed as described (Groh et al., 2006), using primer sets TGCGGCACGCTGCAGGGCT (SEQ ID NO:9) and TTGA-CAGTGACCACACCATGGAGCATA (SEQ ID NO:10) for ERp5 cDNA, and GGAACGGAAAGGACCTCAGGATG (SEQ ID NO:11) and CTGGGAGCTCCTGGTGCTGTTG (SEQ ID NO:12) for MICA cDNA, and SYBR Green reagents (Molecular Probes).

Preparation of dRNase and capturing of ERp5-MICA complexes. RNase A was denatured and reduced in 0.1 M Tris-OH (pH 8.6), 6 M guanidine hydrochloride, and 0.15 M dithiothreitol for 24 h at room temperature (RT), and desalted using D-Salt Dextran columns (Pierce) equilibrated with phosphate-buffered saline (PBS). 2×10⁶ semi-confluent Hela cells were exposed to the indicated concentrations of dRNase or native RNase for 16 h, washed, and surface biotinylated with EZ-Link Sulfo-NHS-LC Biotin (Pierce). Labeled cells were incubated in 0.5 ml 10% (w/v) TCA in PBS for 30 min on ice, washed sequentially in 10% and 5% TCA in PBS, and lysed in 50 mM Tris (pH 7.4), 1% Surfact-Amps NP-40 (Pierce), 150 mM NaCl, 5 mM EDTA, 40 mM N-ethylmaleimide (Sigma), 1 mM PMSF, leupeptin (1 μg/ml), and pepstatin (1 μg/ml). Lysate pH was adjusted to 7.0 with 1 M Tris-OH (pH 9.5). Protein complexes were precipitated with mAb 2C10 (anti-MICA) or ERp5 polyclonal antibody, treated with N-glycanase, and processed for SDS-PAGE. For sequential precipitation, mAb 2C10 immunocomplexes were dissociated in 150 mM Tris (pH 7.4), 0.5% SDS, and 10 mM DTT, diluted 10-fold with lysis buffer containing 25 mM iodoacetamide, incubated for 1 h at RT for DTT neutralization and sulfhydryl alkylation, and reprecipitated with anti-MICA mAb BAMO-1 (Axxora) or anti-ERp5. For determination of sMICA C-terminal cleavage, supernatant from C1R-MICA transfectants grown in Opti-MEM (Gibco) was concentrated using Amicon Ultra-15 centrifugal filters (Millipore). Immunoprecipitated sMICA was treated with N-glycanase, isolated by SDS-PAGE, and subjected to peptide fragmentation analysis by MALDI mass spectrometry at the Harvard University Microchemistry Facility.

ERp5 activity assays. Ectodomain-only MICA, Siderocalin, and CD94-NKG2A were expressed in bacteria and purified as described (Li et al., 2001). The inventors similarly produced ERp5 (residues 1-421 of the mature protein), the ERp5 fragments 1-118 and 135-421, the C36S and C39S mutants (made by Stratagene Quick Change methodology) of ERp5$_{1-118}$, and the isolated MICA α1α2 platform (residues 1-180) and α3 domains (residues 187-274) (Li et al., 1999). All ERp5 sequences were fused to N-terminal hexahistidine tracts and included a C-terminal stop codon to prevent expression of the adjacent hexahistidine in pET22(b). Recombinant proteins were purified by metal affinity (BD Talon, Clontech) and size exclusion chromatography (Superdex 200, Pharmacia). For testing of functional activity, ERp5 or derivative proteins (2 µg) were incubated at RT with MICA substrates or control proteins (1.5 µg) in PNEA [25 mM PIPES (pH 7), 150 mM NaCl, 1 mM EDTA, and 0.02% sodium azide] in a total volume of 5 µl per time point sample, mixed with 2×SDS-PAGE sample buffer (5 µl) with or without β-ME, and resolved in 15% Tris-glycine or 12% Bis-Tris NuPAGE (Invitrogen) gels.

B. Results

Early studies of NKG2D interactions with its ligands utilized randomly oligomerized recombinant MICA (rMICA) or ULBP family ligands produced as immunoglobulin fusion proteins, all of which bound exclusively to NKG2D expressing lymphocytes (Bauer et al., 1999; Cosman et al., 2001). Testing MICA and ULBP2 tetramers, the inventors confirmed that these high avidity reagents stained the NKL NK cell line and that binding was entirely accounted for by NKG2D (FIG. 1A). However, in the course of screening ~40 cell lines by flow cytometry, the inventors observed that MICA, but not ULBP2, tetramers stained cell types lacking NKG2D. The highest fluorescence intensities were recorded with U266 myeloma cells and all of 10 epithelial tumor lines tested and correlated with relatively large amounts of cell surface MICA. Only monocytic U937 cells were identified as negative for tetramer binding (FIG. 1A). The MICA tetramers were prepared using glycosylated protein secreted by transfected 293T cells. However, tetramer binding was not reduced after cleavage of cell surface polypeptide-linked carbohydrates but was inhibited in the presence of unglycosylated rMICA (FIG. 1A). Thus, these results revealed an interaction involving MICA, but not NKG2D ligands in general, and an unidentified surface protein.

Figure 1B:
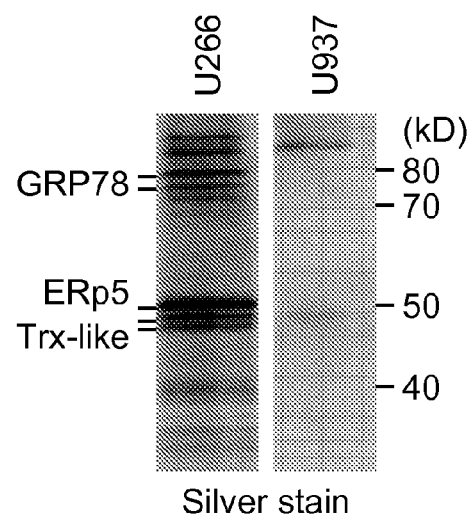
Figure 1C:
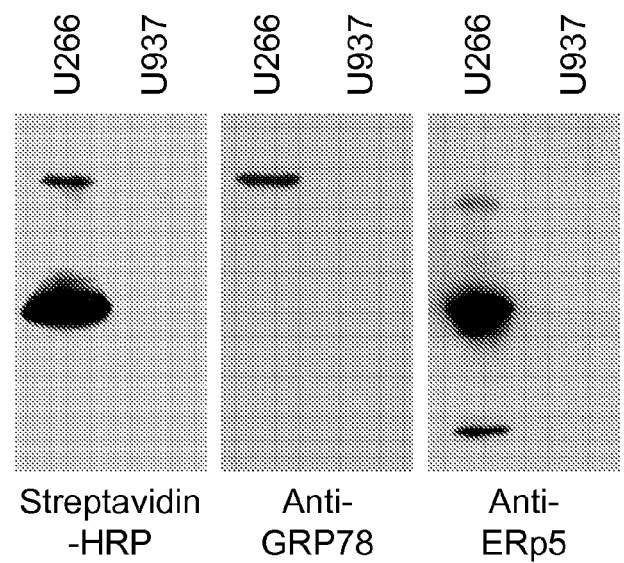
Figure 1D:
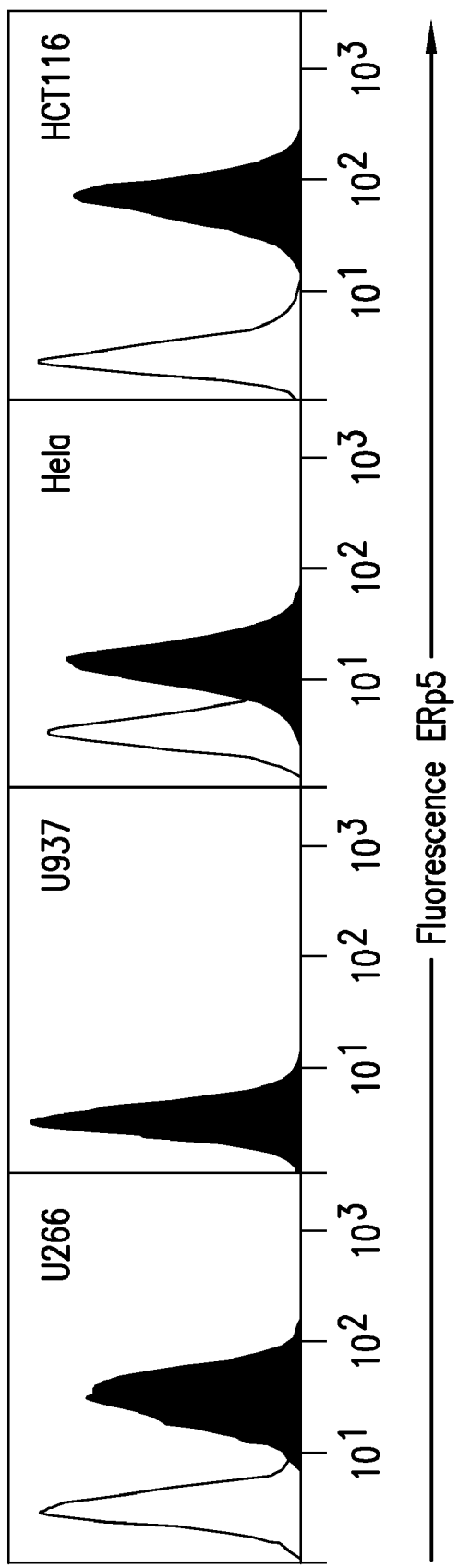

Candidate MICA binding proteins were purified from U266 and negative control U937 outer cell membranes using MICA-coupled sepharose beads. SDS-polyacrylamide gel electrophoresis (SDS-PAGE) and silver staining revealed two sets of protein bands that were detected with U266 but not U937 cells (FIG. 1B). By mass spectrometry, two protein bands in the 76-78 kilodalton (kD) molecular mass range corresponded to glucose-regulated protein 78 (GRP78, also known as BiP). A major protein band of 50 kD was identified as ERp5 (also known as P5) (Ellgard and Ruddock, 2005), and two additional proteins of about 47 and 48 kD shared similarities with thioredoxin family members. Because all of these proteins are typically intracellular, the inventors scrutinized their outer cell membrane localization. Employing the same purification protocol and surface-biotinylated cells, immunoblots probed with streptavidin-horse radish peroxidase (HRP) or polyclonal antibodies demonstrated the presence of GRP78 and more prominently of ERp5 on the surface of U266 but not U937 cells, which was confirmed by staining for ERp5 (FIGS. 1C-1D). ERp5 is related to protein disulfide isomerase (PDI). Both proteins contain two thioredoxin-like domains, each with a pair of active site cysteines in CXXC motifs, and mediate the intracellular formation of nascent polypeptide disulfide bonds; however, they have also been implicated in extracellular disulfide exchange (Ellgaard and Ruddock, 2005; Kikuchi et al., 2002; Turano et al., 2002; Jordan and Gibbins, 2006).

Figure 2A:
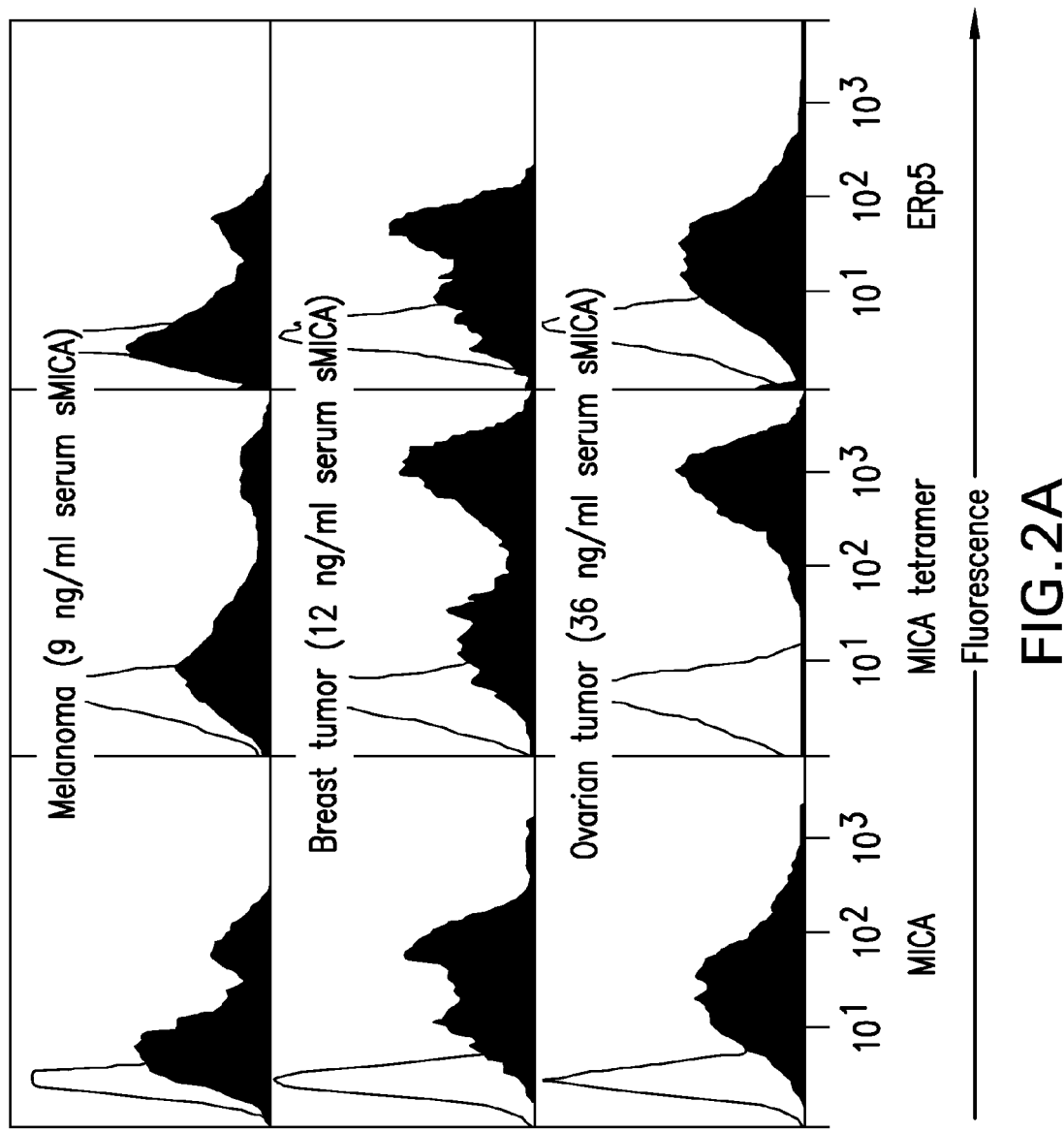
FIGS. 2A-2C—Tumor-associated ERp5 surface expression and pharmacological inhibition of sMICA shedding.
Figure 2B:
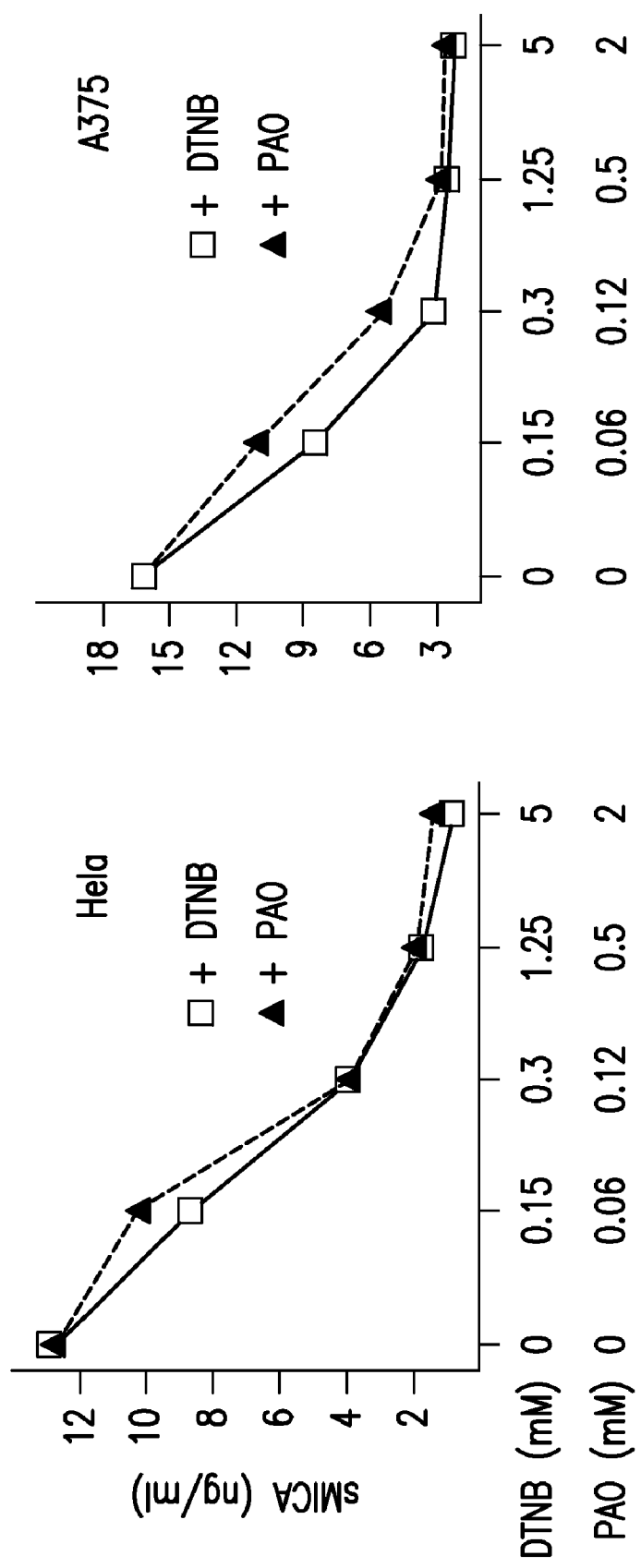
Figure 2C:
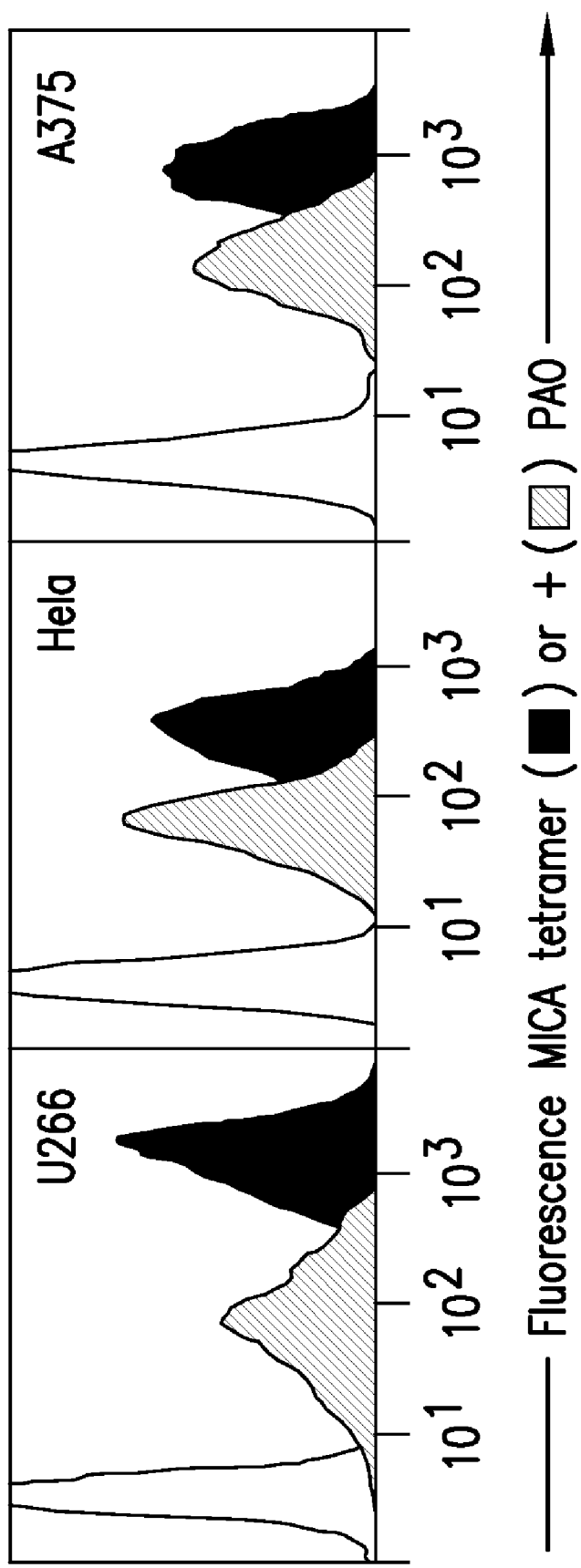
Figure 3C:
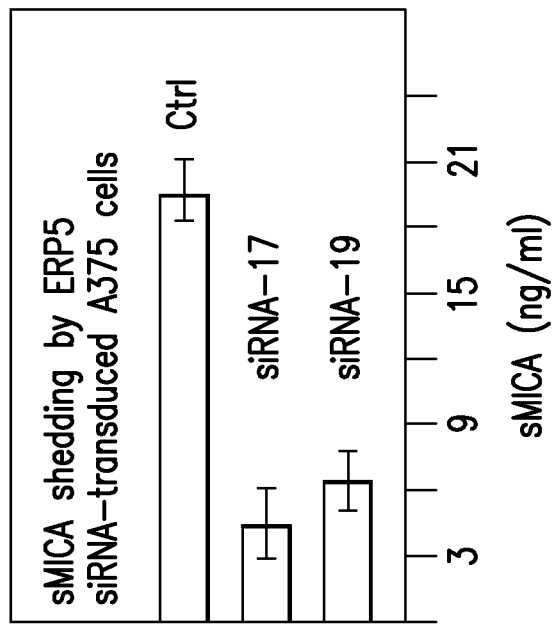
FIGS. 3A-3C—ERp5 is required for sMICA shedding.
Figure 3A:
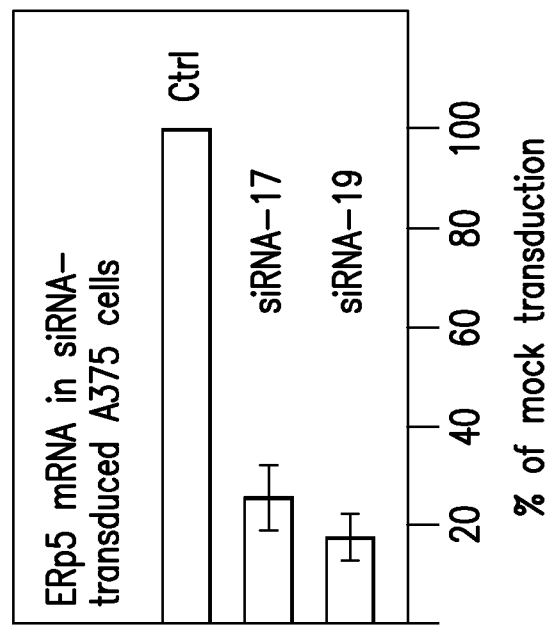
Figure 3B:
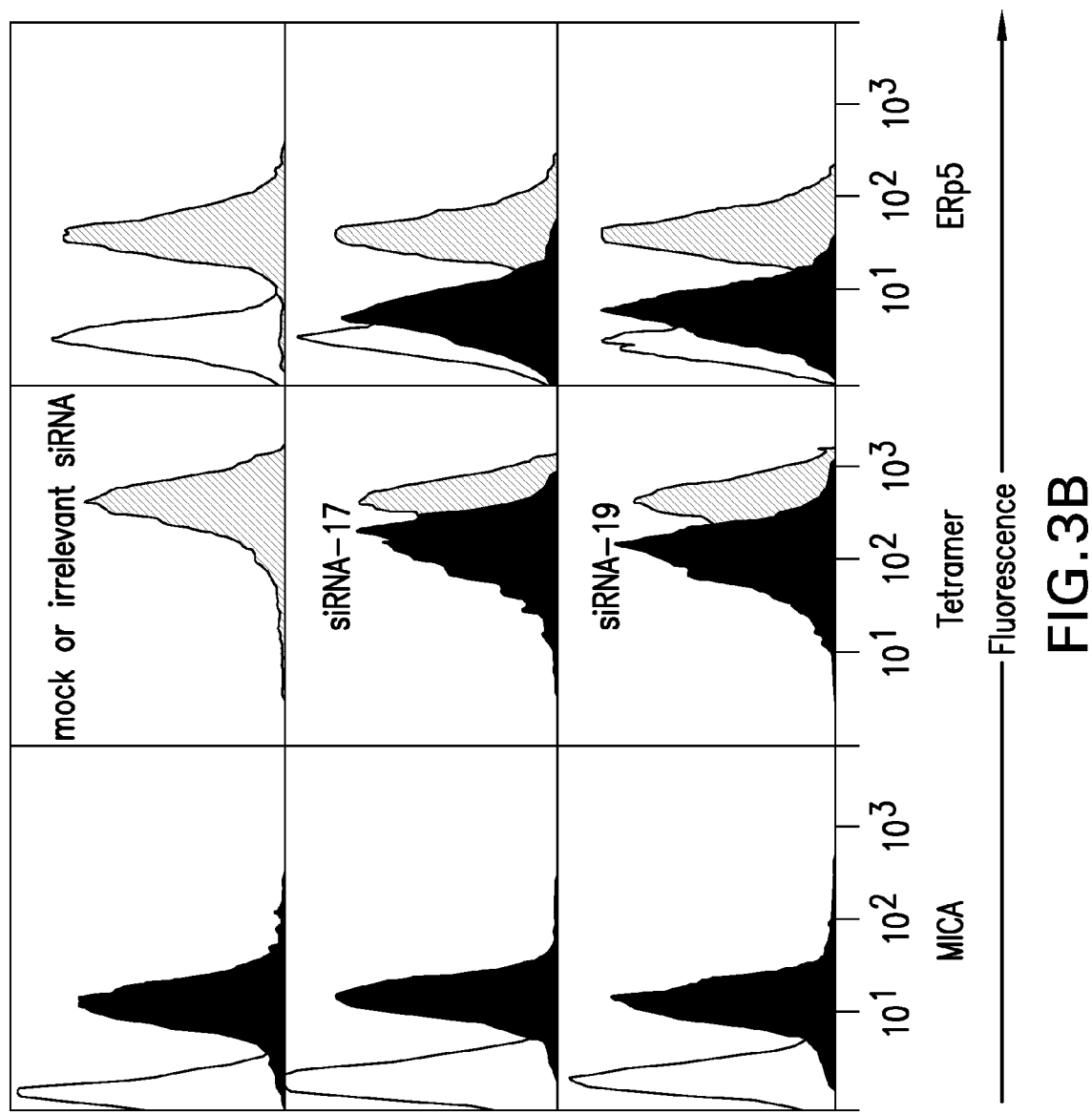

In exploring a functional relationship between MICA and ERp5, the inventors were guided by the epithelial tumor-associated expression that is characteristic of MICA but not of the ULBP family of NKG2D ligands (Gonzales et al., 2006; Groh et al., 2006). This idea was encouraged when freshly isolated tumor cells displayed similar patterns of tetramer and anti-ERp5 and -MICA antibody binding, and matched serum samples were positive for sMICA (FIG. 2A). The inventors thus tested a role of ERp5 in MICA shedding by exposing U266 cells and tumor lines Hela, A375 melanoma, and HCT116 and Lovo colon carcinoma to DTNB [5,5-dithiobis-(2-nitrobenzoic acid)] or PAO (phenylarsine oxide), which impair PDI function by forming disulfide and coordination bonds, respectively, with thiol groups in its catalytic sites$_{18}$. Both inhibitors reduced the production of sMICA at titered non-toxic concentrations without affecting surface expression of MICA (FIG. 2B; data not shown). Treatment with PAO also diminished tetramer binding, suggesting that MICA interacts directly with an ERp5 catalytic site (FIG. 2C). However, these inhibitors are relatively non-specific and may have pleiotropic effects. Therefore, and to preclude an involvement of thiol isomerases other than ERp5, the inventors expressed siRNA constructs targeting two regions of ERp5 mRNA in A375 cells. As measured by real-time reverse transcription PCR (RT-PCR), ERp5 mRNA was reduced by ~70-80% (FIG. 3A). As a consequence, ERp5 surface expression, MICA tetramer binding, and sMICA shedding decreased, although the amounts of MICA surface protein were not noticeably changed (FIGS. 3B-C). Thus, the cumulative evidence indicated that surface ERp5 function is required for MICA shedding.

The functional association between ERp5 and MICA was biochemically analysed. Initial failure to co-immunoprecipitate these proteins from lysates of surface-biotinylated Hela cells implied that ERp5 and MICA maintain no stable complexes after solubilization. However, ERp5 coimmunoprecipitated with MICA when Hela cells were treated with trichloroacetic acid (TCA), which traps mixed disulfide polypeptides and quenches thiol interchange (FIG. 4A, lane 1) (Frand and Kaiser, 1999).

Figure 4A:
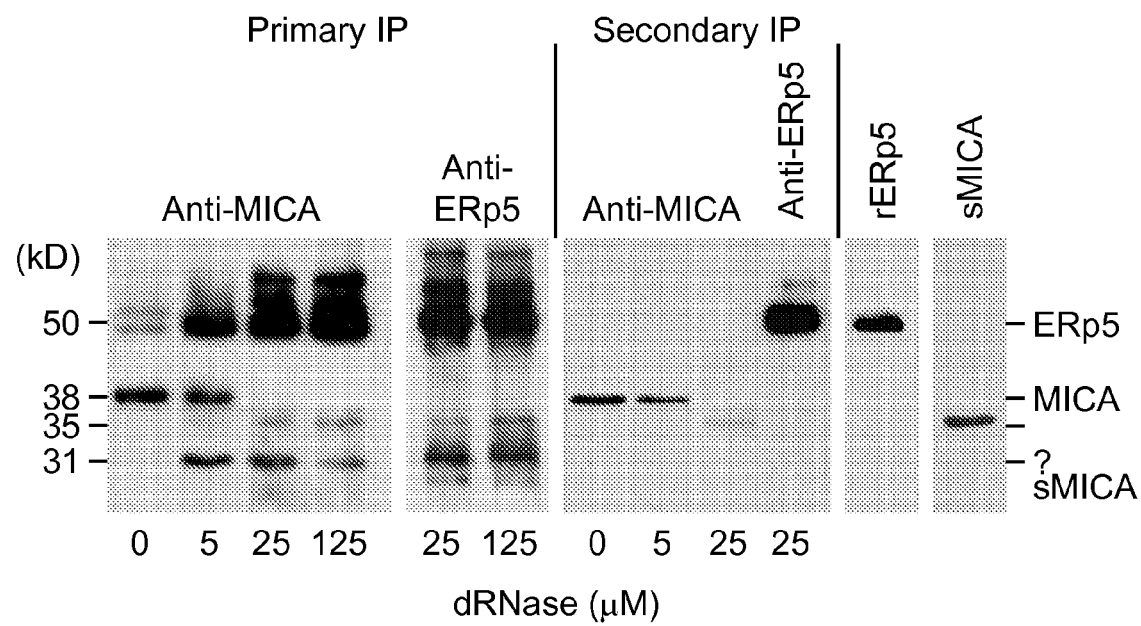
FIGS. 4A-4C—ERp5-MICA disulfide exchange enables MICA cleavage.
Figure 4B:
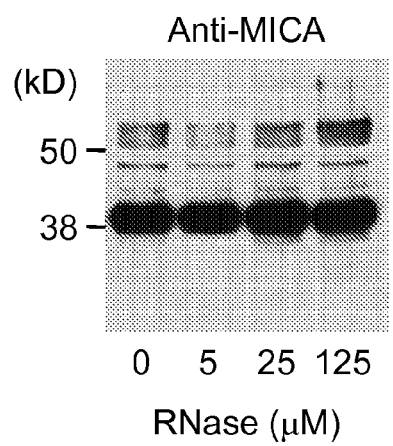
Figure 4C:
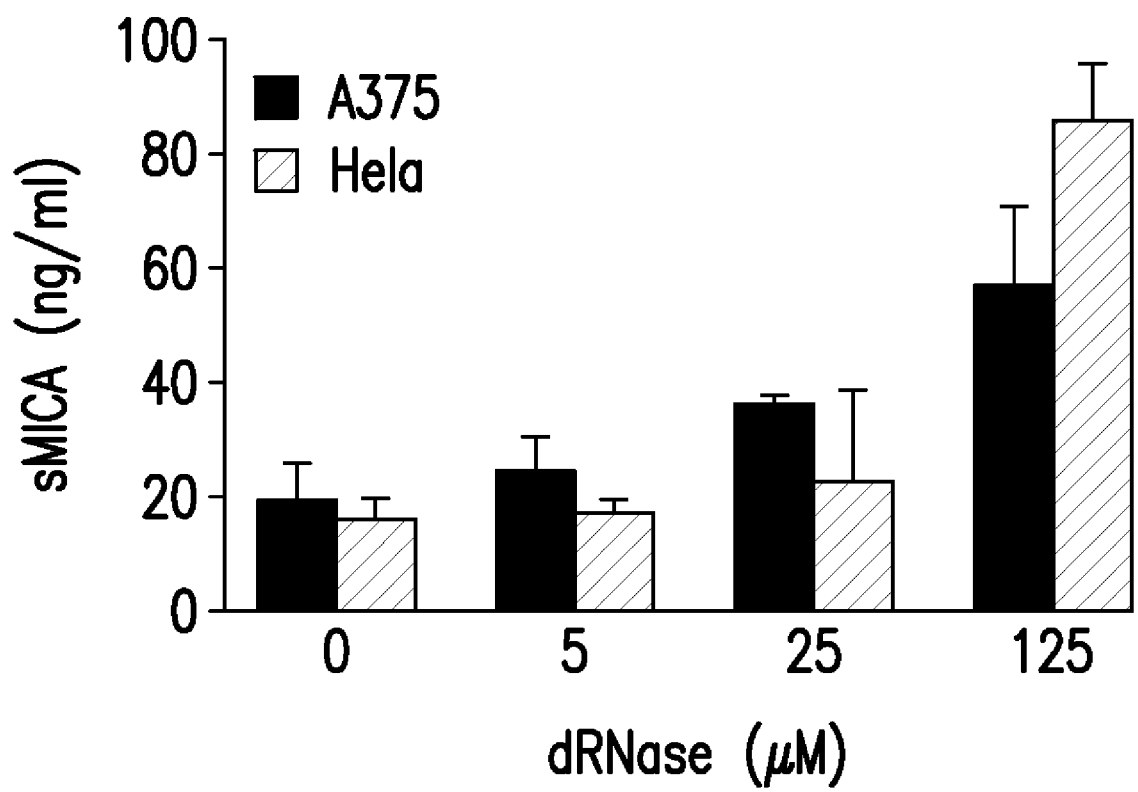

Sulfhydryl groups in subsequent cell lysates were alkylated and immunocomplexes deglycosylated with N-glycanase. This procedure was modified by using Hela cells grown in the presence of denatured and reduced RNase (dRNase), which served as excess substrate shifting ERp5 equilibrium towards the reduced state (Essex et al., 1995), thereby favoring disulfide exchange with MICA. Analysis by SDS-PAGE and immunoblotting showed that increasing concentrations of dRNase resulted in larger amounts of ERp5 co-immunoprecipitating with MICA (FIG. 4A, lanes 1-4). Concomitantly, the MICA polypeptide of 38 kD (shortened in Hela cells due to homozygous cytoplasmic tail deletion) disappeared, and proteins with molecular masses of 31 and 34 kD emerged. The 34 kD protein corresponded to truncated sMICA as determined by secondary precipitation from dissociated immunocomplexes and comparison to sMICA isolated from Hela cell culture media (FIG. 4A, lanes 3, 4, 9 and 12). The 31 kD protein may represent another substrate or co-factor that was recruited into ERp5-MICA complexes. Similar data were obtained using anti-ERp5 for immunoprecipitations (FIG. 4A, lanes 5 and 6). None of those biochemical changes were observed when cells were grown in the presence of native RNase (FIG. 4B). Thus, these results demonstrated dynamic interactions between ERp5 and MICA that were closely tied to the production of sMICA, which was corroborated by large increases of sMICA in dRNase-treated Hela and A375 cell cultures (FIG. 4C). To demonstrate ERp5-mediated MICA disulfide bond reduction and explore substrate and domain specificities, bacterially produced recombinant proteins were mixed and incubated in the absence of reducing agents and thus under oxidizing conditions. Non-reducing gel electrophoresis and comparison to β-mercaptoethanol (β-ME)-treated samples showed gradual reduction of MICA (FIG. 6). This was remarkable as ERp5 affected an intact, properly folded, substrate protein isoenergetically and in the absence of any other factor in solution. A similar result was obtained with the closely related MICB (data not shown). In contrast, ERp5 did not affect unrelated proteins with relatively accessible intrachain (Siderocalin) or intrachain and interchain (CD94-NKG2A) disulfide bonds (FIG. 6). No synergistic effect was observed when MICA was exposed to ERp5 together with GRP78.

Figure 5A:
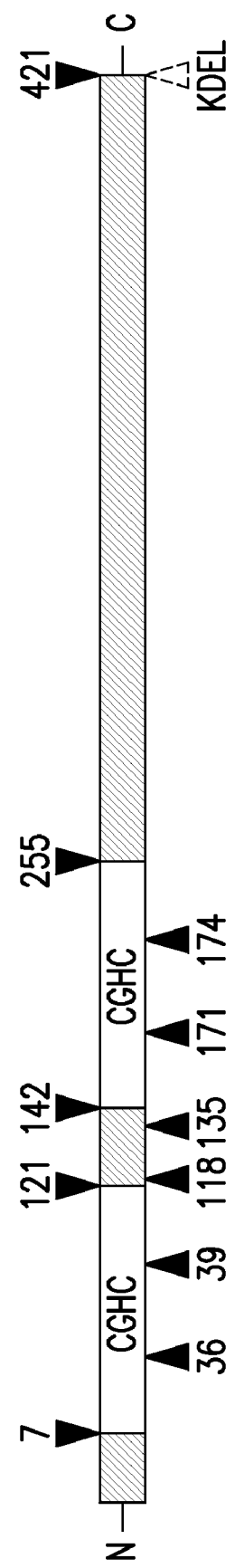

Of the two ERp5 thioredoxin-like domains, which were expressed as two separate polypeptides (amino acid residues 1-118 and 135-421; FIG. 5A), only the N-terminal domain displayed functional activity (FIG. 5B; data not shown). As with PDI, ERp5 employs a catalytic mechanism whereby one active site cysteine invades the target disulfide, transiently forming a disulfide linked heterodimer which is resolved by disulfide exchange with the second active site cysteine (Ellgaard and Ruddock, 2005; Kikuchi et al., 2002). Of two $ERp5_{1-118}$ mutant fragments, C36S showed no activity on MICA substrate whereas C39S formed a trapped disulfide-linked intermediate, thus confirming the role of C36 as the invading and C39 as the resolving cysteine in this reaction (FIG. 5C). By size exclusion chromatography, intact ERp5 was a trimer in solution whereas the two individual domains behaved as monomers (data not shown). Thus, ERp5 multimerization was not required for MICA reduction.

Figures 5D, 5E:
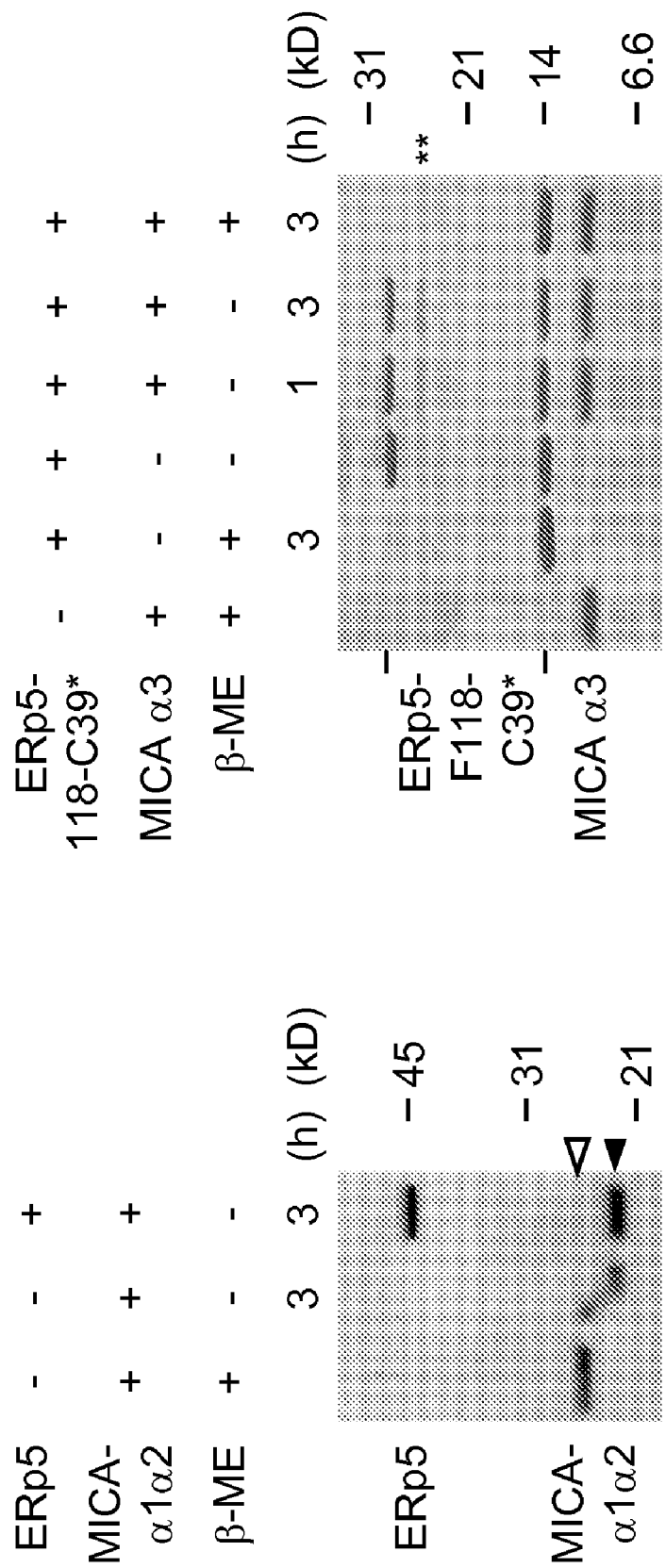

Similar to conventional MHC class I molecules, MICA contains three intrachain disulfide bonds located between amino acid residues 36 and 41, 96 and 164, and 202 and 259 in the α1, α2, and the C-type immunoglobulin-like α3 domain, respectively (Li et al., 1999). To identify the target disulfide, the α1α2 platform and α3 membrane-proximal domains were expressed and tested separately. ERp5 displayed no activity with the α1α2 domain (FIG. 5D). Because the inventors were unable to electrophoretically resolve reduced and non-reduced forms of the relatively small α3 domain, the inventors used the $ERp5_{1-118}$ polypeptide fragment with the C39S mutation for analysis.

Gel electrophoresis revealed a large protein band shift corresponding to a mixed disulfide heterodimer (FIG. 5E). Thus, the disulfide bond targeted by ERp5 was in the MICA α3 domain. Proteolytic cleavage of MICA is thought to be mediated by metalloproteinases (Salih et al., 2002). However, with Hela and A375 cells, the inventors observed no reduction in sMICA shedding by metalloproteinase inhibitors, suggesting that diverse proteases may have the ability to cleave MICA. To determine the MICA cleavage site, the inventors purified sMICA from cultures of transfectant C1R-MICA cells, which express modest amounts of ERp5 but proliferate vigorously in serum-free media. C-terminal sequencing by mass spectroscopy analysis of tryptic peptide fragments revealed ragged MICA C-termini defined by several neighboring amino acid residues at or near the transmembrane boundary.

In conclusion, these results suggest that MICA cleavage occurs in complex with ERp5 before mixed disulfide resolution, which in all likelihood results in immediate 'snap-back' oxidization of the MICA disulfide bond. ERp5 escape from intracellular retention is probably independent of MICA as intracellular interactions have not been observed[27]. Precedent for biological functions of surface thiol isomerases includes alteration of integrin affinity states, CD4 homodimer formation by interchain disulfide exchange, which enables HIV-1 T cell infection, and switching of cell surface tissue factor functional states between activation of coagulation and G protein coupled signaling (Turano et al., 2002; Jordan and Gibbins, 2006; Matthias et al., 2002; Ahamed et al., 2006; Maekawa et al., 2006). The function of ERp5 demonstrated here enables tumor immune evasion and may influence autoimmune diseases through sMICA-mediated T cell modulation.

Example 3

ERp5 Immunomodulatory Effects on T Cells and Dendritic Cells

A. Materials and Methods

Monocytes were enriched from normal peripheral blood mononuclear cells (PBMC) by plastic adherence and cultured under standard conditions in the presence of IL-4 and GM-CSF. Cells were harvested at 6 hour-intervals and stained with fluorescein isothiocyanate (FITC)-anti-CD83 or FITC-HLA-DR followed by saturating phycoerythrin (PE)-MICA tetramer concentrations or polyclonal rabbit anti-ERp5 and PE-goat anti-rabbit Ig. On day 6 of culture with IL-4/GM-CSF, mDC were matured (IL-1β, IL-6, TNFα, and PGE2) and MICA tetramer staining and Erp5 expression monitored for an additional 3 days. MICA tetramer was produced by ectodomain MICA protein expression in transfected 293T cells, protein purification from culture supernatant using Invitrogen technology, and BirA enzymatic biotinylation and conjugation with PE-streptavidin.

mDC were matured using standard cytokine cocktail (Il-1β, IL-6, TNFα, and PGE2) in the additional presence or absence of soluble MICA (10 ng/ml). Mature mDC were harvested after 24 to 48 hours and processed for standard flow cytometry of CD80 and CD83 expression. For IL-6 secretion assays, 24 hour cytokine-matured mDC were washed, mixed with irradiated C1R-Neo (control), C1R-MICA or C1R-ULBP1 cells at a ratio of 2:1 and plated at 50,000 (experiment 1 and 2) or 200,000 mDC (experiment 3 and 4) per round-bottom 96-well in 200 μl AIM-V media with LPS (10 μg/ml). IL-6 contents in culture supernatants were measured by standard ELISA. The ability of mature mDC to present alloantigen in the presence or absence of soluble MICA was studied using standard mixed-lymphocyte reaction (MLR). Irradiated (3000 Rad) cytokine-matured mDC and allogeneic T cells were plated at various ratios (X-axis of bottom bar graph) with or without soluble MICA (10 ng/ml AIM-V) in round-bottom 96-well plates. After 72 hours, cells in wells were labeled with [$^3$H]thymidine for 24 hours and harvested for counting of incorporated radioactivity.

Total PBMC from healthy donors were cultured for 48 hours with PHA (1 μg/ml) or on solid-phase anti-CD3 (25 ng/ml) and stained for standard three-color flow cytometry using combinations of directly conjugated anti-CD3, -CD4 and -CD8 mAbs followed by anti-ERp5 and PE-goat anti-rabbit Ig. For cytokine analyses, bulk NKG2D$^+$ and NKG2D$^-$ T cell populations purified by magnetic sorting were plated on solid-phase monoclonal antibodies with or without soluble MICA (10 ng/ml). 24 hour culture supernatants were screened by 17 multiplex cytokine analysis.

B. Results

Figure 8A:
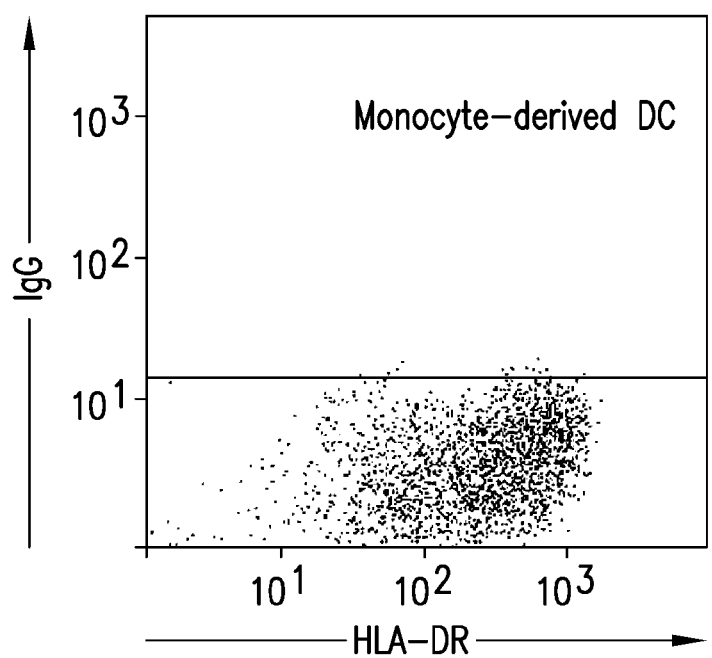
FIGS. 8A-8C—ERp5 expression by monocyte-derived dendritic cells. Erp5 expression (FIG. 8B) by monocyte derived dendritic cells (mDC) is shown.
Figure 8B:
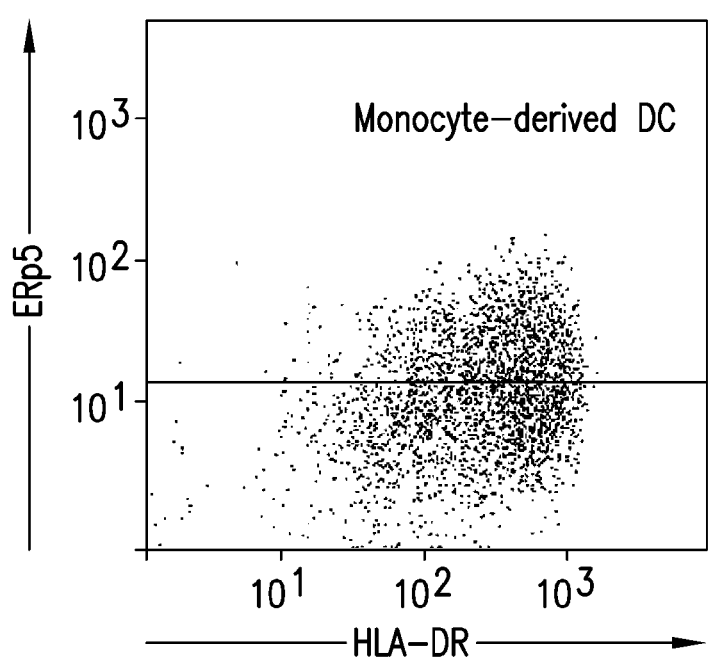
Figure 8C:
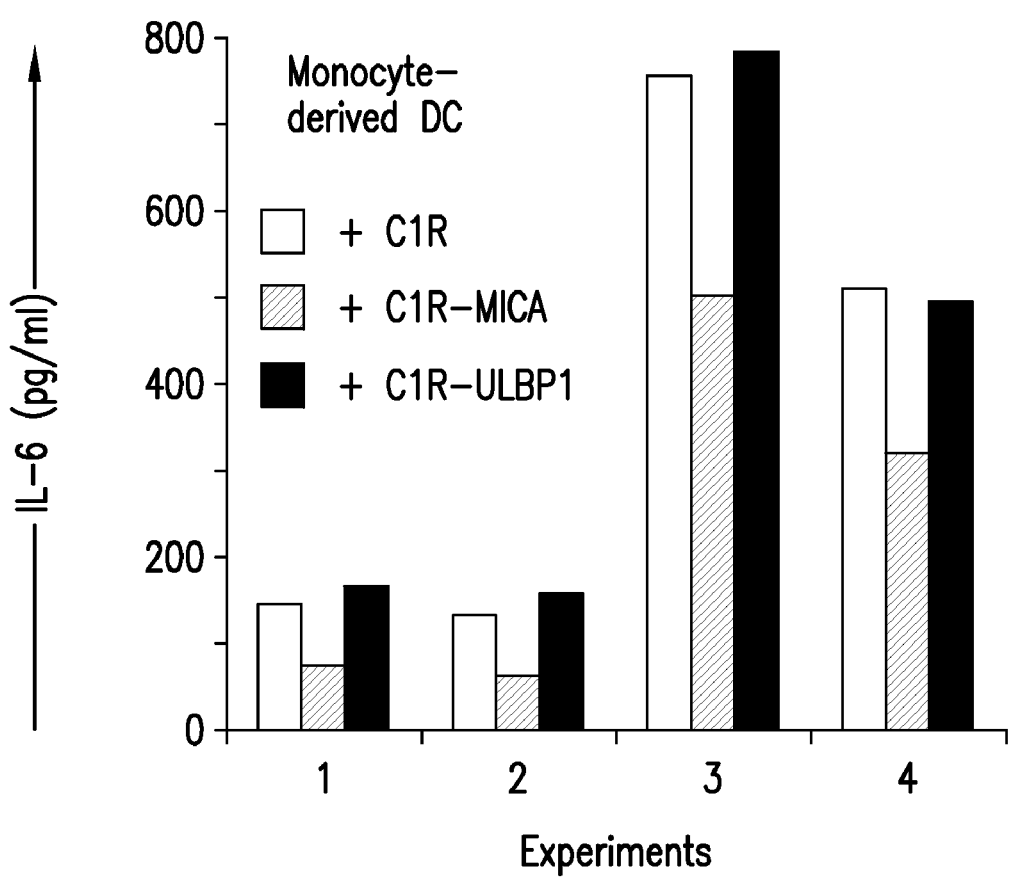

The inventors observed that Erp5 expression becomes first visible after 12 hours of mDC culture and reaches plateau at 48 hours. FIG. 8. Cytokine (IL-1β, IL-6, TNFα, and prostaglandin E2 (PGE2)) mediated maturation had no effect on Erp5 expression.

Expression of DC maturation markers (CD83; CD80) was diminished on mDC matured in the presence of soluble MICA. (not shown). In addition, IL-6 secretion by LPS stimulated mDC was impaired by the additional presence of MICA on irradiated C1R-MICA cell transfectants, but not by C1R-ULBP1 transfectants. FIG. 8. Furthermore, mDC exhibited reduced ability to present alloantigen and stimulate T cells in the presence of soluble MICA.

Figure 7A:
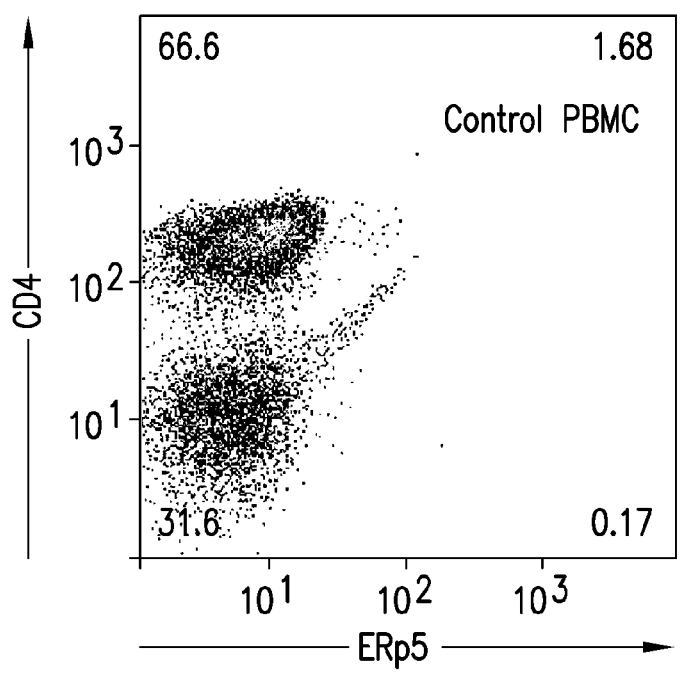
FIGS. 7A-7D—ERp5 expression on activated CD4 T cells and alteration of T cell cytokine profile by soluble MICA. Dot plots (FIGS. 7A-7B): Among PHA (or anti-CD3)-activated PBMC, a majority of CD4 T cells (y-axis) express ERp5 (x-axis) (FIG. 7B), whereas non-activated controls are mostly negative for ERp5 (FIG. 7A). T cells were gated based on CD3 expression (not shown).
Figure 7B:
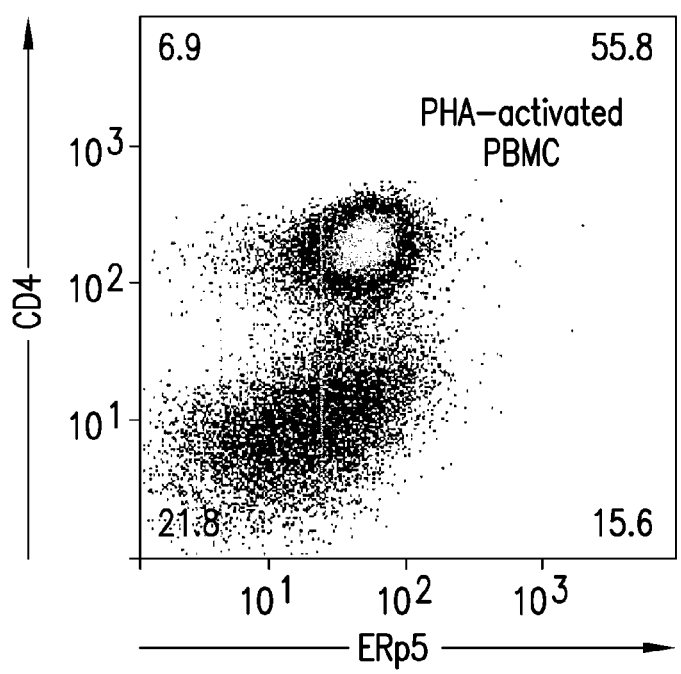
Figure 7C:
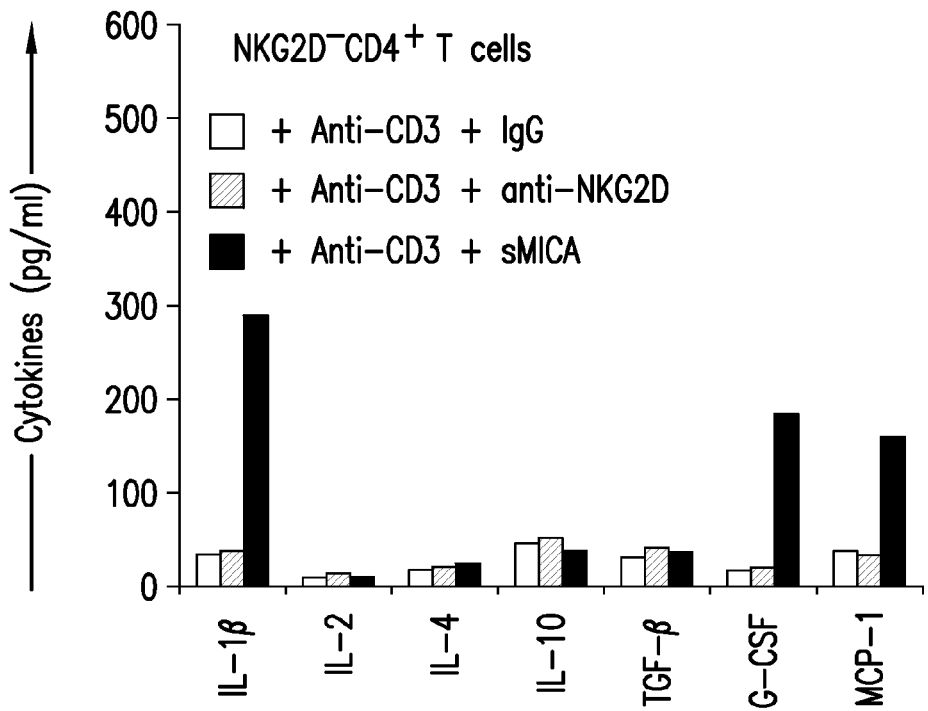
Figure 7D:
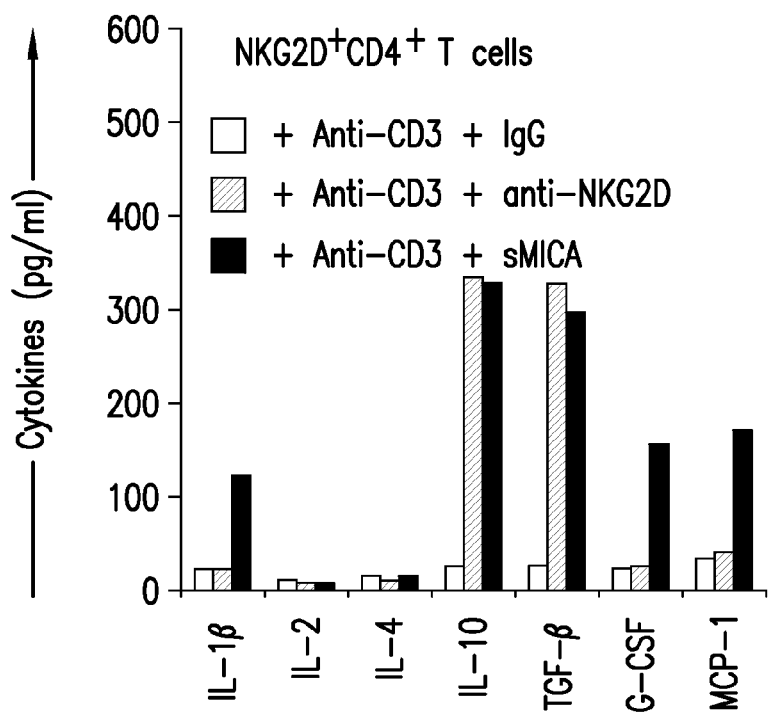

A majority of PHA (or anti-CD3)-activated CD4 T cells (γ-axis) express ERp5 (x-axis) (compare FIG. 7A and FIG. 7B). PHA (or anti-CD3)-activated NKG2D$^+$CD4$^+$ T cells stimulated by anti-NKG2D and soluble MICA produced similar quantities of IL-10 and TGFβ. However, the amounts of IL-1β, IL-17, granulocyte colony-stimulating factor (G-CSF) and monocyte chemoattractant protein 1 (MCP1) were vastly increased in the presence of soluble MICA independent of NKG2D. Similarly, increased amounts of IL-1β, IL-17, G-CSF, and MCP1 were also produced by NKG2D$^-$CD4$^+$ T cells, thus precluding an effect of NKG2D, in the presence of soluble MICA. (compare FIGS. 7C and D). This suggests that the effect of soluble MICA is mediated by ERp5.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 5,229,275
U.S. Pat. No. 5,567,610
U.S. Publn. 2001/0007666
U.S. Publn. 2005/0136102
U.S. Ser. No. 60/913,467
Ahamed et al., *Proc. Natl. Acad. Sci. USA*, 103:13932-13937, 2006.
Akiyama et al., *Alzheimer Dis. Assoc. Disord.*, 14 (1):S47-53, 2000.
Autenrieth et al., *Infect. Immun.*, 62:2590-2599, 1994.
Bahram and Spies, *Immunogenetics*, 43 (4):230-233, 1996.
Bahram et al., *Proc. Natl. Acad. Sci. USA*, 91 (14):6259-6263, 1994.
Bauer et al., *Science*, 285 (5428):727-729, 1999.
Bendzen et al., *Scand. J. Rheumatol.*, 28:599-606, 1988.
Blumberg et al., *Arthritis Rheum.*, 7:93-97, 1964.
Brandt et al., *Arthritis Rheum.*, 43:1346-1352, 2000.
Braun et al., *Arthritis Rheum.*, 42:2039-2044, 1999.
Cann et al., *Gut.*, 24 (12):1135-1140, 1983.
Capaldi et al., *Biochem. Biophys. Res. Comm.*, 74 (2):425-433, 1977.
Chomarat et al., *Arthritis Rheum.*, 38:1046-1054, 1995.
Cosman et al., *Immunity*, 14:123-133, 2001.
Das et al., *Immunity*, 15 (1):83-93, 2001.
de Waal et al., *J. Exp. Med.*, 174:1209-1220, 1991.
Deckert et al., *Int. J. Cancer*, 87 (3):382-90, 2000.
Drossman et al., *Dig. Dis. Sci.*, 38 (9):1569-1580, 1993.
Drossman et al., *Gastroenterol.*, 112 (6):2120-2137, 1997.
Eikelenboom et al., *Glia*, 40 (2):232-239, 2002.
Ellgaard and Ruddock, *EMBO Rep.*, 6:28-32, 2005.
Essex et al., *Blood*, 86:2168-2173, 1995.
Ettehadi et al., *Clin. Exp. Immunol.*, 96 (1):146-151, 1994.
Everhart et al., *Gastroenterol.*, 100 (4):998-1005, 1991.
Frand and Kaiser, *Mol. Cell*, 4:469-477, 1999.
Gehrmann et al., *Neuropathol. Appl. Neurobiol.*, 21:277-289, 1995.
Gladman et al., *J. Rheumatol.*, 22:675-679, 1995.
Gladman et al., *Q. J. Med.*, 62:127-141, 1987.
Gladman, *Rheum. Dis. Clin. North Am.*, 18:247-256, 1992.
Gonzales et al., *Curr. Topics Microbiol. Immunol.*, 298:121-138, 2006.
Graeber et al., *Glia*, 40 (2):252-259, 2002.
Green et al., *Nature Genet.*, 7:13, 1994.
Griffin et al., *Proc. Natl. Acad. Sci. USA*, 86 (19):7611-7615, 1989.
Groh et al, *Proc. Natl. Acad. Sci. USA*, 98:6879, 1998.
Groh et al., *Nat. Immun.*, 2 (3): 255-260, 2001.
Groh et al., *Nature*, 419 (6908):734-738, 2002.
Groh et al., *Nat. Immunol.*, 7:755-762, 2006.
Groh et al., *Proc. Natl. Acad. Sci. USA*, 100 (16):9452-9457, 2003.
Groh et al., *Proc. Natl. Acad. Sci. USA*, 93:12445-12450, 1996.
Groh et al., *Proc. Natl. Acad. Sci. USA*, 96 (12):6879-6884, 1999.
Grossberger and Parham, *Immunogenetics*, 36 (3):166-174, 1992.
Gulbis and Galand, *Hum. Pathol.*, 24 (12):1271-1285, 1993.
Gwee et al., *Gut.*, 44 (3):400-406, 1999.
Haridas et al., *The Journal of Immunology*, 161: 1-6, 1998.
Harris et al., *Nat Rev Drug Discov.*, 2 (3):214-21, 2003.
Harrison and Symmons et al., *Ann. Rheum. Dis.*, 57 (6):375-377, 1998.
Harrison et al., *J. Rheumatol.*, 25 (12):2324-2330, 1998.
Hart et al., *Immunology*, 84:536-542, 1995.
Hohler et al., *Arthritis Rheum.*, 41:1489-1492, 1998.
Hohler et al., *J. Invest. Dermatol.*, 109:562-565, 1997.
Horwitz and Fisher, *N. Engl. J. Med.*, 344 (24):1846-1850, 2001.
Ishizawa and Dickson, *J. Neuropathol. Exp. Neurol.*, 60:647-657, 2001.
Jacob et al., *Proc. Natl. Acad. Sci. USA*, 87:1233-1237, 1990.
Jailwala et al., *Ann. Intern. Med.*, 133 (2):136-147, 2000.
Jones et al., *Br. J. Rheumatol.*, 33:834-839, 1994.
Jordan et al., *Blood*, 105 (4):1500-1507, 2005.
Jordan and Gibbins, *Antioxid. Redox Signal*, 8:312-324, 2006.
Kellow and Phillips, *Gastroenterol.*, 92 (6):1885-1893, 1987.
Kikuchi et al., *J. Biochem.*, 132:451-455, 2002.
Kotake et al., *Infect. Immun.*, 67:2682-2686, 1999.
Lahesmaa et al., *J. Immunol.*, 148:3079-3085, 1992.
Lee et al., *Bioconjug Chem.*, 14 (3):546-53, 2003.
Li et al., *Immunity*, 10: 577-584, 1999.
Li et al., *Nat. Immunol.*, 2: 443-451, 2001.
Locher et al., *J. Ethnopharmacol.*, 49 (1):23-32, 1995.
Lonberg et al., *Nature*, 368:856, 1994.
Lynn and Friedman, *N. Engl. J. Med.*, 329 (26):1940-1945, 1993.
Macatonia et al., *J. Immunol.*, 150:3755-3765, 1993.

Maekawa et al., *J. Immunol.*, 176:6873-6878, 2006.
Marsal et al., *Rheumatology*, 38:332-337, 1999.
Matthias et al., *Nat. Immunol.*, 3:727-732, 2002.
McCafferty et al., *Nature*, 348:552-553, 1990.
McGonagle et al., *Arthritis Rheum.*, 41:694-700, 1998.
McGonagle et al., *Curr. Opin. Rheumatol.*, 11:244-250, 1999.
Mease et al., *Lancet*, 356:385-390, 2000.
Mertz et al., *Gastroenterol.*, 118 (5):842-848, 2000.
Moll and Wright, *Ann. Rheum. Dis.*, 32:181-201, 1973.
Moll and Wright, *Semin. Arthritis Rheum.*, 3:55-78, 1973.
Neal et al., *BMJ*, 314 (7083):779-782, 1997.
Nielen et al., *Arthritis Rheum.*, 50 (2):380-386, 2004.
OMIM 602893
OMIM 604089
OMIM 604142
Opportunistic Mycoses of Man and Other Animals (Smith), 1989.
Orr et al., *Progr Neurobiol.*, 68:325-340, 2002.
Partsch et al., *Br. J. Rheumatol.*, 24:518-523, 1997.
PCT Appln. PCT/US03/12299
Pimentel et al., *Am. J. Gastroenterol.*, 95 (12):3503-3506, 2000.
Pociot et al., *Scand. J. Immunol.*, 42 (4):501-504, 1995.
Rantapaa-Dahlqvist et al., *Arthritis Rheum.*, 48 (10):2741-2749, 2003.
Remington's Pharmaceutical Sciences, 15th ed., 33:624-652, Mack Publishing Company, Easton, Pa., 1980.
Ribbens et al., *Eur. Cytokine Netw.*, 11:669-676, 2000.
Rogers et al., *Neurobiol Aging*, 9 (4):339-349, 1988.
Rothstein, *Med. Clin. North Am.*, 84 (5):1247-1257, 2000.
Salih et al., *J. Immunol.*, 169:4098-4102, 2002.
Salvarani et al., *Curr. Opin. Rheumatol.*, 10:299-305, 1998.
Sandler, *Gastroenterol.*, 99 (2):409-415, 1990.
Schellekens et al., *Arthritis Rheum.*, 43 (1):155-163, 2000.
Schlaak et al., *Clin. Exp. Rheumatol.*, 14:155-162, 1996.
Schlaak et al., *Eur. J. Immunol.*, 22:2771-2776, 1992.
Scripp's Antifungal Report, 1992
Sieper and Braun, *Arthritis Rheum.*, 38:1547-1554, 1995.
Simon et al., *Bio/Technology*, 1:784-791, 1983.
Simon et al., *Proc. Natl. Acad. Sci. USA*, 91:8562-85666, 1994.
Spies et al., *Proc. Natl. Acad. Sci. USA*, 86 (22):8955-8958, 1989.
Steinle et al., *Immunogenetics*, 53 (4):279-87, 2001.
Talley et al., *Gastroenterology*, 109 (6):1736-1741, 1995.
Taylor et al., *Int. Immun.*, 6:579, 1994.
Tieng et al., *Proc. Natl. Acad. Sci. USA*, 99 (5):2977-82, 2002.
Touzani et al., *J. Neuroimmunol.*, 100 (1-2):203-215, 1999.
Turano et al., *J. Cell Physiol.*, 193:154-163, 2002.
Whitehead et al., *Gastroenterol.*, 98 (5 Pt 1):1187-1192, 1990.
Wright, *Ann. Rheum. Dis.*, 15:348-356, 1956.
Wright, *Clin. Orthop. Related Res.*, 143:8-14, 1979.
Yin et al., *Arthritis Rheum.*, 40:1788-1797, 1997.
Yin et al., *Rheumatology*, 38:1058-1067, 1999.

What is claimed is:

1. A method of inhibiting shedding of MIC polypeptides from a MIC expressing cancer cell comprising contacting a MIC expressing cancer cell with an anti-MIC α3 domain antibody.

2. The method of claim 1, wherein said MIC is MICA.

3. The method of claim 1, wherein said MIC is MICB.

4. The method of claim 1, wherein said anti-MIC antibody is a bi-specific antibody comprising at least one binding region that is specific for surface-bound MIC.

* * * * *